United States Patent
Tsumura et al.

(10) Patent No.: US 12,249,406 B2
(45) Date of Patent: *Mar. 11, 2025

(54) FEATURE QUANTITY CALCULATING METHOD, FEATURE QUANTITY CALCULATING PROGRAM, AND FEATURE QUANTITY CALCULATING DEVICE, SCREENING METHOD, SCREENING PROGRAM, AND SCREENING DEVICE, COMPOUND CREATING METHOD, COMPOUND CREATING PROGRAM, AND COMPOUND CREATING DEVICE

(71) Applicant: FUJIFILM Corporation, Tokyo (JP)

(72) Inventors: Kyosuke Tsumura, Minami-Ashigara (JP); Shino Ohira, Minami-Ashigara (JP); Jun Nakabayashi, Minami-Ashigara (JP); Mizuki Takei, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 510 days.

This patent is subject to a terminal disclaimer.

(21) Appl. No.: 17/484,047

(22) Filed: Sep. 24, 2021

(65) Prior Publication Data

US 2022/0068441 A1 Mar. 3, 2022

Related U.S. Application Data

(63) Continuation of application No. PCT/JP2020/013333, filed on Mar. 25, 2020.

(30) Foreign Application Priority Data

Mar. 29, 2019 (JP) .................................. 2019-066981

(51) Int. Cl.
*G16C 20/40* (2019.01)
*G01N 33/15* (2006.01)
(Continued)

(52) U.S. Cl.
CPC ............. *G16C 20/40* (2019.02); *G01N 33/15* (2013.01); *G01N 33/50* (2013.01); *G16C 20/64* (2019.02)

(58) Field of Classification Search
CPC ........ G16C 20/30; G16C 20/64; G16C 20/50; G16C 20/40; G16C 20/70; G01N 33/15; G01N 33/50
See application file for complete search history.

(56) References Cited

U.S. PATENT DOCUMENTS 7,751,987 B1* 7/2010 Becker ................... G16B 15/00
702/27
9,373,059 B1 6/2016 Heifets et al.
(Continued)

FOREIGN PATENT DOCUMENTS

CN 101344902 A 1/2009
CN 102930181 A 2/2013
(Continued)

OTHER PUBLICATIONS

English translation of Ohira et al., "A Newly Developed Method Based on AI-oriented Amino Acid Interaction Mapping (AI-AAM) for Efficient Virtual Scaffold Hopping," Preprints of the 41st Symposium on Chemoinformatics, Oct. 27, 2018, 3 pages total.
(Continued)

*Primary Examiner* — An H Do
(74) *Attorney, Agent, or Firm* — Birch, Stewart, Kolasch & Birch, LLP

(57) ABSTRACT

Provided are a feature quantity calculating method, a feature quantity calculating program, and a feature quantity calculating device which enable calculation of a feature quantity accurately showing chemical properties of a target structure, a screening method, a screening program, and a screening device which enable efficient screening of a pharmaceutical candidate compound using a feature quantity, and a com- (Continued)

pound creating method, a compound creating program, and a compound creating device which enable efficient creation of a three-dimensional structure of a pharmaceutical candidate compound using a feature quantity. Since the chemical properties of target structures are exhibited as the result of an interaction between the target structure and probes in the periphery thereof, the fact that the degree of accumulation of the probes is similar between target structures indicates that the chemical properties of the target structures are similar. Therefore, the feature quantity accurately showing the chemical properties of the target structure can be calculated using the feature quantity calculating method according to one aspect of the present invention.

24 Claims, 33 Drawing Sheets

(51) Int. Cl.
    *G01N 33/50*        (2006.01)
    *G16C 20/64*        (2019.01)

(56) References Cited

U.S. PATENT DOCUMENTS

| | | | |
|---|---|---|---|
| 11,031,094 B2* | 6/2021 | Blattner | G16B 30/00 |
| 2003/0017483 A1 | 1/2003 | Ecker et al. | |
| 2003/0143628 A1 | 7/2003 | Onizuka | |
| 2005/0267687 A1* | 12/2005 | Tomii | G16B 30/10 |
| | | | 702/19 |
| 2009/0060588 A1 | 3/2009 | Tanaka | |
| 2010/0312538 A1 | 12/2010 | Umeyama et al. | |
| 2012/0232856 A1 | 9/2012 | Bendtsen | |
| 2013/0046482 A1 | 2/2013 | Andersen et al. | |
| 2015/0310162 A1 | 10/2015 | Okuno et al. | |
| 2015/0313898 A1 | 11/2015 | Tomkinson et al. | |
| 2016/0300127 A1 | 10/2016 | Heifets et al. | |
| 2019/0018924 A1 | 1/2019 | Mackinnon et al. | |
| 2020/0243166 A1 | 7/2020 | Tsumura et al. | |

FOREIGN PATENT DOCUMENTS

| | | |
|---|---|---|
| EP | 1010681 A1 | 6/2000 |
| EP | 1 083 980 B1 | 3/2007 |
| JP | 7-13959 A | 1/1995 |
| JP | 2002-228656 A | 8/2002 |
| JP | 2003-520940 A | 7/2003 |
| JP | 2004-220571 A | 8/2004 |
| JP | 2004-287812 A | 10/2004 |
| JP | 2005-49188 A | 2/2005 |
| JP | 2007-213290 A | 8/2007 |
| JP | 2007-299125 A | 11/2007 |
| JP | 2009-84015 A | 3/2009 |
| JP | 4564097 B2 | 10/2010 |
| JP | 5946045 B2 | 7/2016 |
| JP | 2017-520868 A | 7/2017 |
| JP | 2019-28879 A | 2/2019 |
| JP | 2019-508821 A | 3/2019 |
| WO | WO 97/24301 A1 | 7/1997 |
| WO | WO 2005/103994 A1 | 11/2005 |
| WO | WO 2009/064015 A1 | 5/2009 |
| WO | WO 2014/034577 A1 | 3/2014 |
| WO | WO 2015/168774 A1 | 11/2015 |
| WO | WO 2019/078006 A1 | 4/2019 |

OTHER PUBLICATIONS

Extended European Search Report for corresponding European Application No. 20783157.9, dated May 16, 2022.
Extended European Search Report for European Application No. 20792167.7, dated Sep. 12, 2022.
Kirsch et al., "Concepts and Core Principles of Fragment-Based Drug Design," Molecules, vol. 24, Nov. 26, 2019, p. 4309 (22 pages total).
Raschka et al., "Machine learning and AI-based approaches for bioactive ligand discovery and GPCR-ligand recognition," Methods, vol. 180, 2020 (Available online Jul. 6, 2020), pp. 89-110.
Wójcikowski et al., "Development of a protein-ligand extended connectivity (PLEC) fingerprint and its application for binding affinity predictions," Bioinformatics, vol. 35, No. 8, Sep. 8, 2018, pp. 1334-1341.
Chinese Office Action and Search Report for Chinese Application No. 201880067748.X, dated Mar. 25, 2023, with an English translation.
Singaporean Office Action for Singaporean Application No. 11202110812Y, dated Sep. 18, 2023.
Japanese Office Action for corresponding Japanese Application No. 2021-511868, dated Dec. 26, 2022, with English translation.
Japanese Office Action for Japanese Application No. 2021-514871, dated Dec. 28, 2022, with English translation.
Extended European Search Report dated Oct. 1, 2020 for Application No. 18868536.6.
Indian Office Action for Indian Application No. 202017014616, dated Jun. 18, 2021, with English translation.
International Preliminary Report on Patentability (Form PCT/IPEA/409), dated Nov. 1, 2019, for International Application No. PCT/JP2018/037051, with an English translation.
International Preliminary Report on Patentability and Written Opinion of the International Searching Authority (Forms PCT/IB/326, PCT/IB/373, and PCT/ISA/237) for International Application No. PCT/JP2020/013333, dated Oct. 14, 2021, with English translation of the Written Opinion.
International Preliminary Report on Patentability and Written Opinion of the International Searching Authority (Forms PCT/IB/326, PCT/IB/373, and PCT/ISA/237) for International Application No. PCT/JP2020/015198, dated Oct. 28, 2021, with English translation of the Written Opinion.
International Search Report (Form PCT/ISA/210) for International Application No. PCT/JP2020/015198, dated Jul. 21, 2020, with English translation.
International Search Report (Form PCT/ISA/210), dated Oct. 30, 2018, for International Application No. PCT/JP2018/037051, with an English translation.
International Search Report (PCT/ISA/210) for International Application No. PCT/JP2020/013333, dated Jul. 14, 2020, with English translation.
Japanese Office Action dated Sep. 7, 2020 for Application No. 2019-549195 with an English translation.
Ohira et al., "A Newly Developed Method Based on AI-oriented Amino Acid Interaction Mapping (AI-AAM) for Efficient Virtual Scaffold Hopping," Preprints of the 41st Symposium on Chemoinformatics, Oct. 27, 2018, pp. 1-2 (4 pages total).
Written Opinion of the International Searching Authority (Form PCT/ISA/237), dated Oct. 30, 2018, for International Application No. PCT/JP2018/037051.
Japanese Notice of Reasons for Refusal for Japanese Application No. 2021-004840, dated Jan. 20, 2022, with an English translation.
Japanese Office Action for Japanese Application No. 2021-004840, dated Aug. 19, 2022, with English translation.
English Machine Translation of JP 2007-213290-A, dated Aug. 23, 2007.
English Machine Translation of JP 2019-28879-A, dated Feb. 21, 2019.
Invitation to Respond to Written Opinion for Singaporean Application No. 11202110812Y, dated Nov. 15, 2022.
Indian Office Action for Indian Application No. 202117046716, dated Aug. 5, 2022, with English translation.
Bender et al., "Molecular Surface Point Environments for Virtual Screening and the Elucidation of Binding Patterns (MOLPRINT 3D)," Journal of Medicinal Chemistry, vol. 47, No. 26, 2004, pp. 6569-6583.
U.S. Office Action for U.S. Appl. No. 16/850,838, dated Mar. 15, 2024.

(56) References Cited

OTHER PUBLICATIONS

U.S. Office Action for U.S. Appl. No. 16/850,838, dated Sep. 3, 2024.
Yamazaki et al., "Spatial Decomposition of Solvation Free Energy Based on the 3D Integral Equation Theory of Molecular Liquid: Application to Miniproteins," Journal of Physical Chemistry B, vol. 115, 2011, pp. 310-318.

* cited by examiner

FIG. 8
| | THREE-DIMENSIONAL AAM DESCRIPTOR (LEVEL SURFACE WITH RESPECT TO THRESHOLD) | THREE-DIMENSIONAL AAM DESCRIPTOR (LEVEL SURFACE WITH RESPECT TO THRESHOLD) AND THREE-DIMENSIONAL STRUCTURE OF COMPOUND |
|---|---|---|
| DIRECTION 1 | 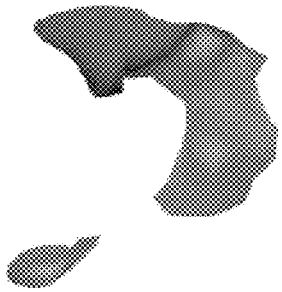 |  |
| DIRECTION 2 | 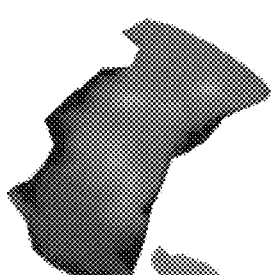 |  |
| DIRECTION 3 | 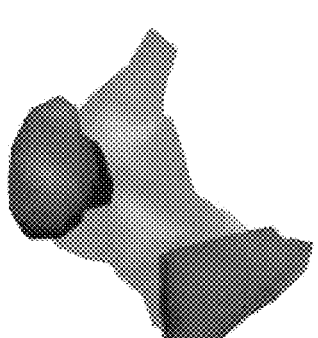 | 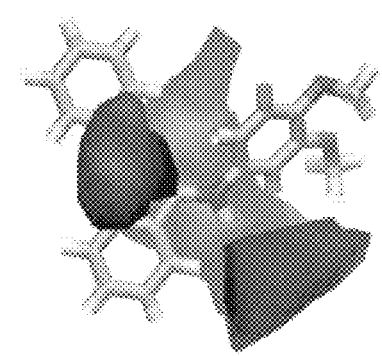 |

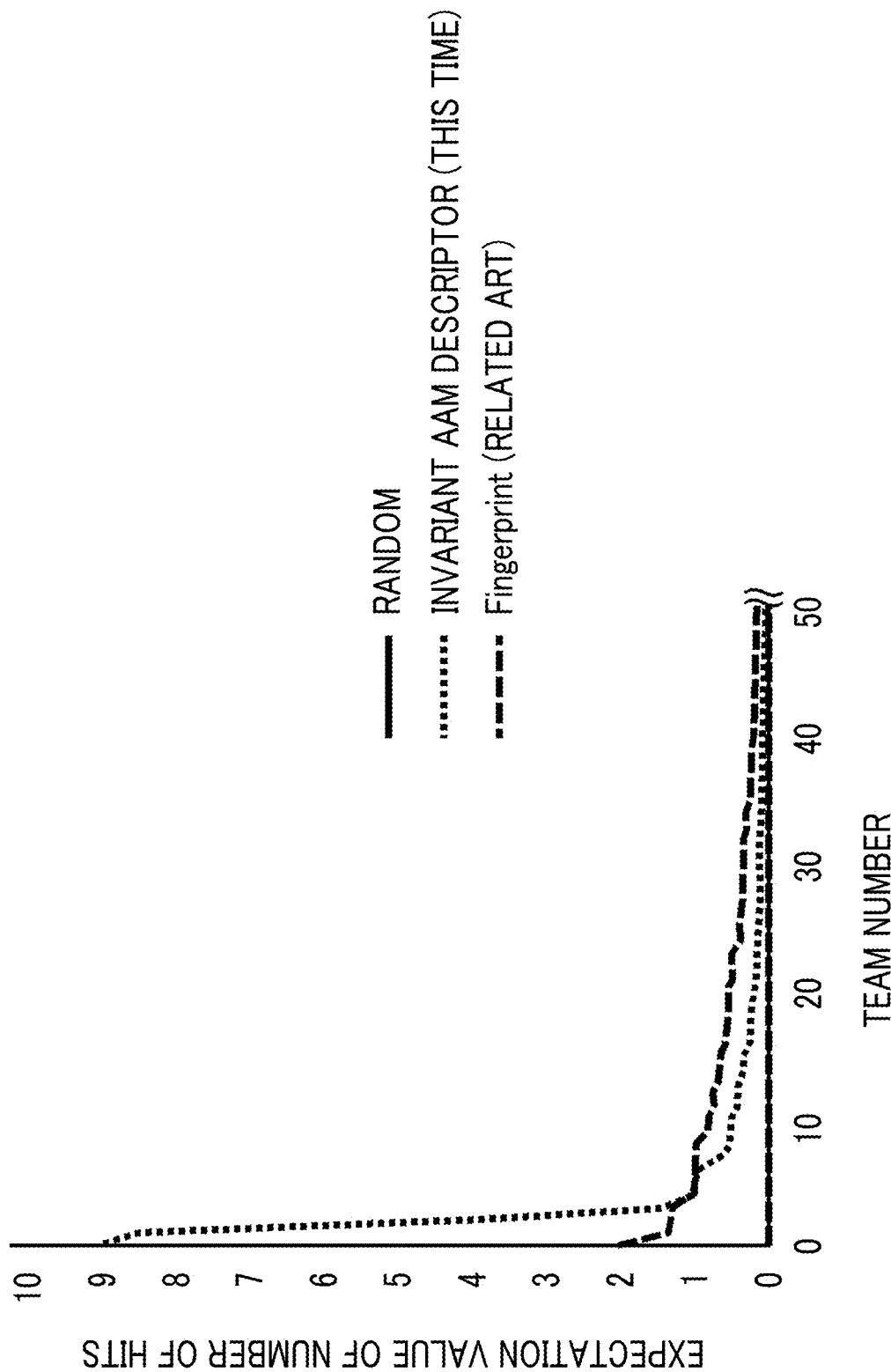

FIG. 17A

| LIGAND | | COMPOUND | | SIMILARITY | EXTRACTION RESULT |
|---|---|---|---|---|---|
| IDENTIFICATION INFORMATION | THREE-DIMENSIONAL AAM DESCRIPTOR | IDENTIFICATION INFORMATION | THREE-DIMENSIONAL AAM DESCRIPTOR | | |
| L00001 | $L00001\_g_i(r)$ | C00001 | $C00001\_g_i(r)$ | 85% | EXTRACTED |
| | | C00002 | $C00002\_g_i(r)$ | 73% | NOT EXTRACTED |
| | | ... | ... | ... | ... |
| | | C00100 | $C00100\_g_i(r)$ | 91% | EXTRACTED |
| | | ... | ... | ... | ... |
| | | C01000 | $C01000\_g_i(r)$ | 80% | EXTRACTED |
| | | ... | ... | ... | ... |

FIG. 17B

| LIGAND | | COMPOUND | | SIMILARITY | | EXTRACTION RESULT |
|---|---|---|---|---|---|---|
| IDENTIFICATION INFORMATION | INVARIANT AAM DESCRIPTOR | IDENTIFICATION INFORMATION | INVARIANT AAM DESCRIPTOR | VALUE | RANK | |
| L00001 | $L00001\_F_{12}(s)$ | C00100 | $C00100\_F_{12}(s)$ | 91% | 1 | EXTRACTED |
| | | C00001 | $C00001\_F_{12}(s)$ | 85% | 2 | EXTRACTED |
| | | ... | ... | ... | ... | ... |
| | | C01000 | $C01000\_F_{12}(s)$ | 80% | 100 | EXTRACTED |
| | | ... | ... | ... | ... | ... |
| | | C00002 | $C00002\_F_{12}(s)$ | 73% | 265 | NOT EXTRACTED |
| | | ... | ... | ... | ... | ... |

EXTRACTED

FIG. 19A

| POCKET STRUCTURE | | COMPOUND | | SIMILARITY | EXTRACTION RESULT |
|---|---|---|---|---|---|
| IDENTIFICATION INFORMATION | THREE-DIMENSIONAL AAM DESCRIPTOR | IDENTIFICATION INFORMATION | THREE-DIMENSIONAL AAM DESCRIPTOR | | |
| P00001 | P00001_$g_1(r)$ | C00001 | C00001_$g_1(r)$ | 85% | EXTRACTED |
| | | C00002 | C00002_$g_1(r)$ | 73% | NOT EXTRACTED |
| | | ... | ... | ... | ... |
| | | C00100 | C00100_$g_1(r)$ | 91% | EXTRACTED |
| | | ... | ... | ... | ... |
| | | C01000 | C01000_$g_1(r)$ | 80% | EXTRACTED |
| | | ... | ... | ... | ... |

FIG. 19B

| POCKET STRUCTURE | | COMPOUND | | SIMILARITY | | EXTRACTION RESULT | |
|---|---|---|---|---|---|---|---|
| IDENTIFICATION INFORMATION | INVARIANT AAM DESCRIPTOR | IDENTIFICATION INFORMATION | INVARIANT AAM DESCRIPTOR | VALUE | RANK | | |
| P00001 | P00001_$F_{12}(s)$ | C00100 | C00100_$F_{12}(s)$ | 91% | 1 | EXTRACTED | EXTRACTED |
| | | C00001 | C00001_$F_{12}(s)$ | 85% | 2 | EXTRACTED | |
| | | ... | ... | ... | ... | ... | |
| | | C01000 | C01000_$F_{12}(s)$ | 80% | 100 | EXTRACTED | |
| | | ... | ... | ... | ... | ... | |
| | | C00001 | C00001_$F_{12}(s)$ | 73% | 265 | NOT EXTRACTED | |
| | | ... | ... | ... | ... | ... | |

FIG. 24
| Step1: | CALCULATE THREE-DIMENSIONAL AAM DESCRIPTOR OF PLURALITY OF COMPOUNDS AND CREATE PAIR OF STRUCTURAL FORMULA AND THREE-DIMENSIONAL AAM DESCRIPTOR |
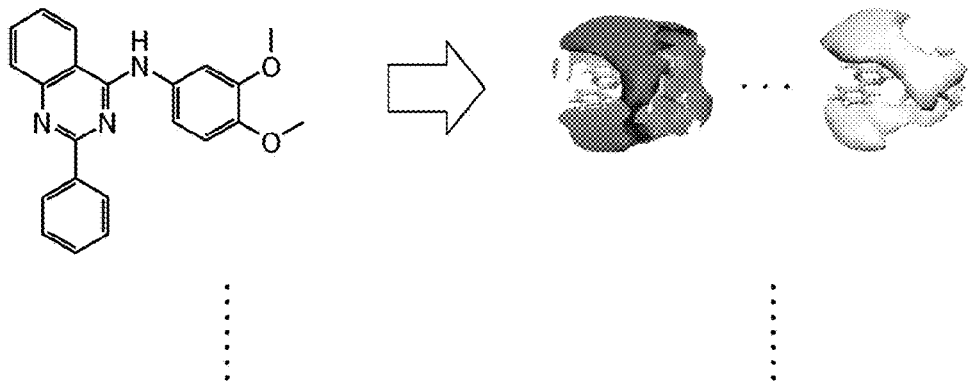
| Step2: | THREE-DIMENSIONAL DESCRIPTOR (EXPLANATORY VARIABLE)     THREE-DIMENSIONAL STRUCTURE OF COMPOUND (TEACHER DATA) |
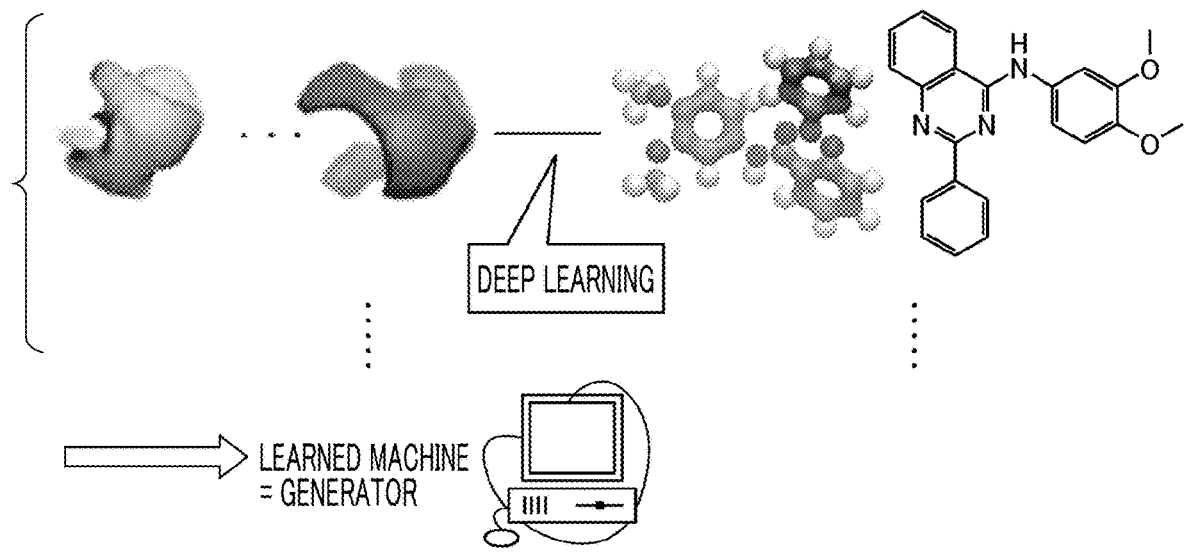
DEEP LEARNING
⇒ LEARNED MACHINE = GENERATOR FIG. 25
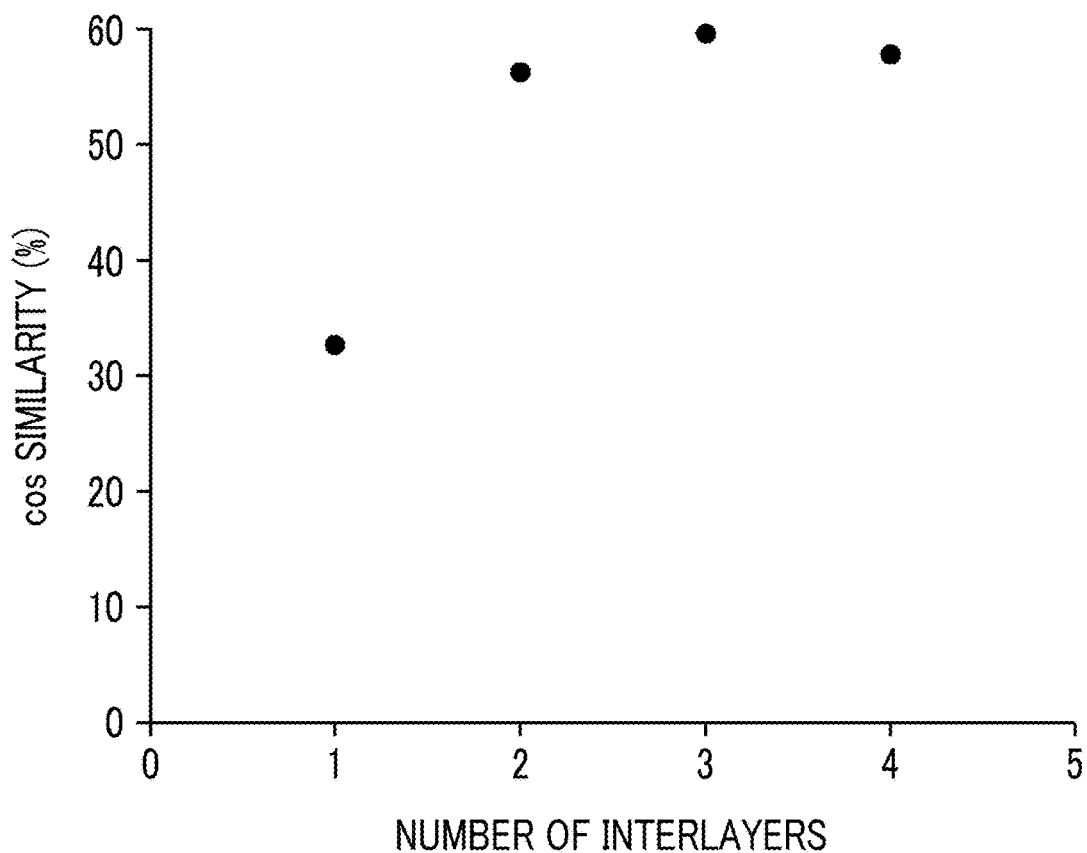
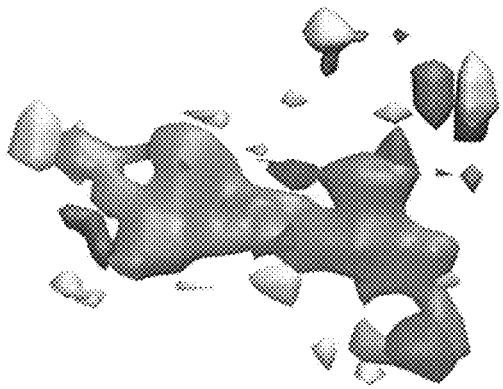
FIG. 26A
STRUCTURAL FORMULA GENERATED
FROM THREE-DIMENSIONAL
AAM DESCRIPTOR
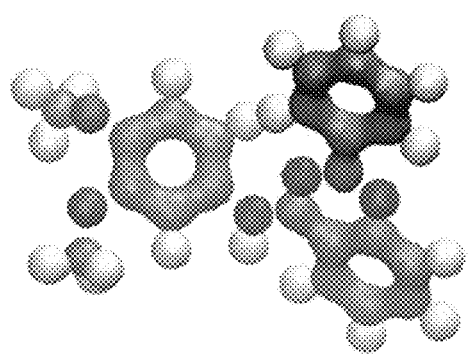
FIG. 26B
CORRECT STRUCTURAL
FORMULA

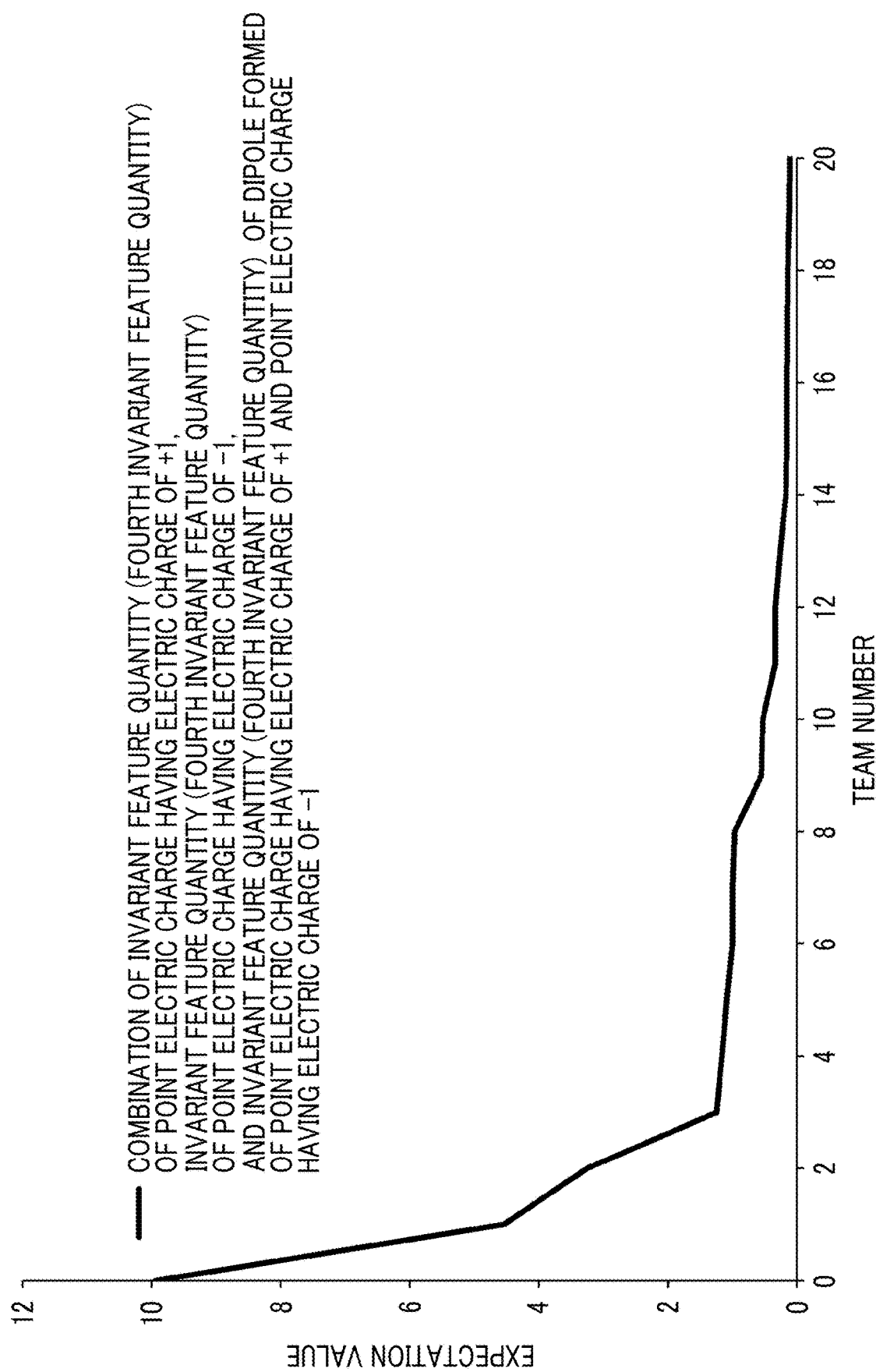

FEATURE QUANTITY CALCULATING METHOD, FEATURE QUANTITY CALCULATING PROGRAM, AND FEATURE QUANTITY CALCULATING DEVICE, SCREENING METHOD, SCREENING PROGRAM, AND SCREENING DEVICE, COMPOUND CREATING METHOD, COMPOUND CREATING PROGRAM, AND COMPOUND CREATING DEVICE

CROSS-REFERENCE TO RELATED APPLICATIONS

The present application is a Continuation of PCT International Application No. PCT/JP2020/013333 filed on Mar. 25, 2020 claiming priority under 35 U.S.C § 119(a) to Japanese Patent Application No. 2019-066981 filed on Mar. 29, 2019. Each of the above applications is hereby expressly incorporated by reference, in its entirety, into the present application.

BACKGROUND OF THE INVENTION

1. Field of the Invention

The present invention relates to a method, a program, and a device which perform calculation of a feature quantity, screening of a compound, and creation of a three-dimensional structure of a compound and particularly relates to a technique for searching for a pharmaceutical candidate compound.

2. Description of the Related Art

In the related art, in the drug discovery research using a computer, pharmaceutical candidate compounds (hereinafter, referred to as "hits") have been searched for by preparing a library having tens of thousands to hundreds of thousands of existing compounds, providing the structural formulae of the compounds, and examining the binding force with respect to one target protein. For example, U.S. Pat. No. 9,373,059B predicts a binding force by providing the structural formula of a compound. Further, JP5946045B also describes that a compound having a desired binding force is searched for gradually by repeating generation of a structural formula and prediction of a binding force (trial and error).

Further. JP4564097B describes that a search is performed using a descriptor referred to as "compound fingerprint". The "descriptor" indicates information obtained from the structural formula of a compound, and the "compound fingerprint" indicates information related to the presence or absence of various functional groups. Such a descriptor has a characteristic in that "in a case where the descriptors of compounds are similar, the skeletons of the compounds are similar".

SUMMARY OF THE INVENTION

Recently, since highly required target proteins have been complicated and difficult, it is difficult to find hits simply by screening libraries. Meanwhile, the theoretical number of compounds is (the 60th power of 10) even limiting the number to low molecules with a molecular weight of 500 or less. The number thereof is further increased in a case of widening the range to middle molecules with a molecular weight of approximately 1000, and thus there is still a possibility of finding hits, considering that the number of compounds synthesized since the dawn of history is approximately (the ninth power of 10). However, it is almost impossible to examine the binding force with respect to all the astronomical numbers of compounds by experiments or simulations. Even in a case of examination of the binding force with respect to some compounds, the efficiency is low only by repeating trial and error as described in U.S. Pat. No. 9,373,059B and JP5946045B. Further, in the case of a descriptor (feature quantity) in the related art such as the fingerprint described in JP4564097B, the feature quantities of compounds are not necessarily similar even in a case where the compounds exhibit the same drug efficacy. Further, since the feature quantities did not accurately show the chemical properties of the target structure, the efficiency of search using the feature quantities was low.

As described above, in the related art, feature quantities do not accurately show the chemical properties of the target structures, and thus the efficiency of screening using the feature quantity and creation of a three-dimensional structure is low.

The present invention has been made in consideration of the above-described circumstances, and an object thereof is to provide a feature quantity calculating method, a feature quantity calculating program, and a feature quantity calculating device which enable calculation of a feature quantity accurately showing chemical properties of a target structure. Further, another object of the present invention is to provide a screening method, a screening program, and a screening device which enable efficient screening of a pharmaceutical candidate compound using a feature quantity. Further, still another object of the present invention is to provide a compound creating method, a compound creating program, and a compound creating device which enable efficient creation of a three-dimensional structure of a pharmaceutical candidate compound using a feature quantity.

In order to achieve the above-described object, according to a first aspect of the present invention, there is provided a feature quantity calculating method comprising: a target structure designating step of designating a target structure formed of a plurality of unit structures having chemical properties; a three-dimensional structure generating step of generating a three-dimensional structure using the plurality of unit structures for the target structure; a feature quantity calculating step of calculating a feature quantity obtained by quantifying, in a three-dimensional space, a degree of accumulation of one or more kinds of probes in a periphery of the three-dimensional structure; and an invariant conversion step of converting the feature quantity into an invariant with respect to rotation and translation of the target structure to calculate an invariant feature quantity, in which the probe is a single point having a real electric charge and generating a van der Waals force.

Since the chemical properties of target structures are exhibited as the result of an interaction between the target structure and one or more kinds of probes in the periphery thereof, the fact that the degree of accumulation of the probes is similar between target structures indicates that the chemical properties of the target structures are similar. That is, target structures having similar feature quantities calculated according to the first aspect exhibit similar chemical properties. Therefore, according to the first aspect, the feature quantity accurately showing the chemical properties of a target structure can be calculated. Further, in the first aspect, since the feature quantity is converted into an invariant with respect to rotation and translation of the compound, the feature quantity is easily handled and the data capacity can be reduced. The conversion of the feature quantity into an invariant can be performed by Fourier transform, angular integration of a correlation function, or the like.

In the first aspect, the probe ("single point") is different from the mathematical "point" and thus may have a size (an actual monoatom, an actual monatomic ion, or the like). Further, a virtual point electric charge (one aspect of the "point") may be used as the probe instead of an actual monoatom or the like. The probe can be selected according to a target compound (target structure).

In the feature quantity calculating method according to a second aspect, in the first aspect, a compound is designated as the target structure in the target structure designating step, a three-dimensional structure of the compound formed of a plurality of atoms is generated in the three-dimensional structure generating step, a first feature quantity which is a feature quantity obtained by quantifying, in the three-dimensional space, the degree of accumulation of the probes in the periphery of the three-dimensional structure of the compound generated in the three-dimensional structure generating step which is the degree of accumulation using one or more kinds of monatomic ions as the probes is calculated in the feature quantity calculating step, and a first invariant feature quantity is calculated by converting the first feature quantity into an invariant with respect to rotation and translation of the compound in the invariant conversion step.

In the present invention, deoxyribonucleic acid (DNA), ribonucleic acid (RNA), cell membranes, and polysaccharides, which are biopolymers (compounds) other than proteins can be treated as the targets of drugs. The second aspect defines the method of calculating the feature quantity of these target compounds, and the probes are formed of one or more kinds of monatomic ions. Since the drug efficacy (the binding force with respect to a target such as DNA) of a compound is locally exhibited as the result of an interaction between the compound and a probe, in a case where the degree of accumulation of monatomic ions (probes) is similar between compounds, the compounds have similar binding forces with respect to the targets. That is, compounds having similar first invariant feature quantities exhibit similar drug efficacies. Therefore, according to the second aspect, the feature quantity accurately showing the chemical properties of a compound can be calculated.

In the feature quantity calculating method according to a third aspect, in the second aspect, the first feature quantity of a first probe that is formed of the one or more kinds of monatomic ions and the first feature quantity of a second probe that is formed of the one or more kinds of monatomic ions and different from the first probe are calculated in the feature quantity calculating step, and the first invariant feature quantity is calculated using the first feature quantity of the first probe and the first feature quantity of the second probe in the invariant conversion step.

According to the third aspect, since the conversion into an invariant can be performed while information related to the interaction between the probes is maintained using the first feature quantity of two different kinds of probes (the first and second probes) in the calculation of the first invariant feature quantity, the comparison of compounds (determination of the drug efficacy) can be accurately performed based on the feature quantity (first invariant feature quantity). In the third aspect, a case where at least one of the kind, the number, or the combination of constituent elements (one or more kinds of monatomic ions) of the first and second probes is different corresponds to the case where "the second probe is different from the first probe".

In the feature quantity calculating method according to a fourth aspect, in the first aspect, a compound is designated as the target structure in the target structure designating step, a three-dimensional structure of the compound formed of a plurality of atoms is generated in the three-dimensional structure generating step, a second feature quantity which is a feature quantity obtained by quantifying, in the three-dimensional space, the degree of accumulation of the probes in the periphery of the three-dimensional structure of the compound generated in the three-dimensional structure generating step which is the degree of accumulation using one or more selected from a first point electric charge having an electric charge of +1, a second point electric charge having an electric charge of −1, a third point electric charge having an electric charge of +0.1, a fourth point electric charge having an electric charge of −0.1, and a fifth point electric charge having an electric charge of 0, as the probes is calculated in the feature quantity calculating step, and a second invariant feature quantity is calculated by converting the second feature quantity into an invariant with respect to rotation and translation of the compound in the invariant conversion step. Further, the compound used as the target structure in the fourth aspect may be a biopolymer.

The fourth aspect defines the feature quantity calculating method for virtual probes, and similar to the second aspect, compounds having similar feature quantities according to the fourth aspect exhibit similar drug efficacies. Therefore, even in a case where virtual probes are used, the feature quantity accurately showing the chemical properties of the target structure can be calculated.

In the feature quantity calculating method according to a fifth aspect, in the fourth aspect, the second feature quantity of a first probe that is formed of one or more selected from the first point electric charge, the second point electric charge, the third point electric charge, the fourth point electric charge, and the fifth point electric charge and the second feature quantity of a second probe that is formed of one or more selected from the first point electric charge, the second point electric charge, the third point electric charge, the fourth point electric charge, and the fifth point electric charge and different from the first probe are calculated in the feature quantity calculating step, and the second invariant feature quantity is calculated using the second feature quantity of the first probe and the second feature quantity of the second probe in the invariant conversion step.

According to the fifth aspect, since the conversion into an invariant can be performed while information related to the interaction between the probes is maintained using the second feature quantity of two different kinds of probes (the first and second probes) in the calculation of the second invariant feature quantity, the comparison of compounds (determination of the drug efficacy) can be accurately performed based on the feature quantity (second invariant feature quantity). In the fifth aspect, a case where at least one of the kind, the number, or the combination of constituent elements (the first point electric charge and the like) of the first and second probes is different corresponds to the case where "the second probe is different from the first probe".

In the feature quantity calculating method according to a sixth aspect, in the fifth aspect, a compound is designated as the target structure in the target structure designating step, a three-dimensional structure of the compound formed of a plurality of atoms is generated in the three-dimensional structure generating step, a third feature quantity which is a feature quantity obtained by quantifying, in the three-dimensional space, the degree of accumulation of the probes in the periphery of the three-dimensional structure of the compound generated in the three-dimensional structure generating step which is the degree of accumulation using the first probe that is formed of one or more kinds of monatomic ions and the second probe that is formed of one or more selected from the first point electric charge having an electric charge of +1, the second point electric charge having an electric charge of −1, the third point electric charge having an electric charge of +0.1, the fourth point electric charge having an electric charge of −0.1, and the fifth point electric charge having an electric charge of 0, as the probes is calculated in the feature quantity calculating step, and a third invariant feature quantity is calculated using the third feature quantity of the first probe and the third feature quantity of the second probe in the invariant conversion step.

In the feature quantity calculating method according to a seventh aspect, in the sixth aspect, the third feature quantity of two kinds of the probes in which at least one of the first probe or the second probe is different is calculated in the feature quantity calculating step, and the third invariant feature quantity is calculated using the third feature quantity of the two kinds of the probes in the invariant conversion step.

According to the seventh aspect, since the conversion into an invariant can be performed while information related to the interaction between the probes is maintained using the third feature quantity of two different kinds of probes in the calculation of the third invariant feature quantity, the comparison of compounds (determination of the drug efficacy) can be accurately performed based on the feature quantity (third invariant feature quantity). In the seventh aspect, "two kinds of probes in which at least one of the first probe or the second probe is different" are probes formed of the first probe and the second probe. Among two kinds of probes in which the combination of the first probe and the second probe is different, the concept of "two kinds of probes" include a case where "the first probes are the same as each other and the second probes are different from each other", for example, a case where one set of probes are formed of sodium ions (monatomic ions; an example of the first probe) and a first point electric charge (an example of the second probe) and the other set of probes are formed of sodium ions (monatomic ions; an example of the first probe) and a second point electric charge (another example of the second probe); a case where "the first probes are different from each other and the second probes are the same as each other", for example, a case where one set of probes are formed of sodium ions (monatomic ions; an example of the first probe) and a first point electric charge (an example of the second probe) and the other set of probes are formed of calcium ions (monatomic ions; another example of the first probe) and a first point electric charge (an example of the second probe); and a case where "both the first probes and the second probes are different from each other", for example, a case where one set of probes are formed of sodium ions (monatomic ions; an example of the first probe) and a first point electric charge (an example of the second probe) and the other set of probes are formed of calcium ions (monatomic ions; another example of the first probe) and a second point electric charge (another example of the second probe). Here, a case where at least one of the kind, the number, or the combination of constituent elements of the probes is different corresponds to the case where "one probe is different from the other probe".

In order to achieve the above-described object, according to an eighth aspect of the present invention, there is provided a feature quantity calculating program which causes a computer to execute the feature quantity calculating method according to any one of the first to seventh aspects. The "computer" in the eighth aspect can be realized using one or more of various processors such as a central processing unit (CPU). Further, a non-temporary recording medium on which a computer-readable code of the feature quantity calculating program according to the eighth aspect is recorded can also be exemplified as an aspect of the present invention.

In order to achieve the above-described object, according to a ninth aspect of the present invention, there is provided a feature quantity calculating device comprising: a target structure designation unit which designates a target structure formed of a plurality of unit structures having chemical properties; a three-dimensional structure generation unit which generates a three-dimensional structure using the plurality of unit structures for the target structure; a feature quantity calculation unit which calculates a feature quantity obtained by quantifying, in a three-dimensional space, a degree of accumulation of one or more kinds of probes in a periphery of the three-dimensional structure; and an invariant conversion unit which converts the feature quantity into an invariant with respect to rotation and translation of the target structure to calculate an invariant feature quantity, in which the probe is a single point having a real electric charge and generating a van der Waals force.

In the ninth aspect, as described above for the first to eighth aspects, the first to third feature quantities and the first to third invariant feature quantities can be calculated using DNA and the like as the target compounds and the monatomic ions, the virtual electric charge, and the combination thereof as the probes.

In order to achieve the above-described object, according to a tenth aspect of the present invention, there is provided a screening method of extracting a target compound which is bound to a target biopolymer other than a protein from a plurality of compounds, the method comprising: a storing step of storing a three-dimensional structure of a compound formed of a plurality of atoms and the first invariant feature quantity of the three-dimensional structure of the compound which is calculated using the feature quantity calculating method according to the second aspect in association with each other for each of the plurality of compounds; a feature quantity calculating step of calculating the first invariant feature quantity of a binding compound that is a compound whose binding to the target biopolymer other than the protein has been confirmed; a similarity calculating step of calculating a similarity between the first invariant feature quantity of the plurality of compounds and the first invariant feature quantity of the binding compound; and a compound extracting step of extracting the target compound from the plurality of compounds based on the similarity.

As described above for the second aspect, according to the present invention, DNA or the like which is a target biopolymer other than a protein can be handled, and in a case where the target compound and the binding compound that is bound to the target biopolymer have similar first invariant feature quantities, the drug efficacies of both the target compound and the binding compound are similar. Therefore, according to the tenth aspect, a target compound having drug efficacy similar to that of the binding compound is extracted based on the first invariant feature quantity so that screening of a pharmaceutical candidate compound can be efficiently performed. Further, a compound having a similarity greater than or equal to the threshold may be extracted or a compound may be extracted in a descending order of the similarity in the compound extracting step.

In order to achieve the above-described object, according to an eleventh aspect of the present invention, there is provided a screening method of extracting a target compound which is bound to a target biopolymer from a plurality of compounds, the method comprising: a storing step of storing a three-dimensional structure of a compound formed of a plurality of atoms and the second invariant feature quantity of the three-dimensional structure of the compound which is calculated using the feature quantity calculating method according to the fourth aspect in association with each other for each of the plurality of compounds; a feature quantity calculating step of calculating the second invariant feature quantity of a binding compound that is a compound whose binding to the target biopolymer has been confirmed; a similarity calculating step of calculating a similarity between the second invariant feature quantity of the plurality of compounds and the second invariant feature quantity of the binding compound; and a compound extracting step of extracting the target compound from the plurality of compounds based on the similarity.

As described above for the fourth aspect, compounds having similar second invariant feature quantities exhibit similar drug efficacies. Therefore, according to the eleventh aspect, even in a case where a virtual probe (the point electric charge or the like) is used, a target compound having drug efficacy similar to that of the binding compound is extracted based on the second invariant feature quantity so that screening of a pharmaceutical candidate compound can be efficiently performed. Further, a compound having a similarity greater than or equal to the threshold may be extracted or a compound may be extracted in a descending order of the similarity in the compound extracting step.

In order to achieve the above-described object, according to a twelfth aspect of the present invention, there is provided a screening program which causes a computer to execute the screening method according to the tenth or eleventh aspect. The "computer" in the twelfth aspect can be realized using one or more of various processors such as a central processing unit (CPU). Further, a non-temporary recording medium on which a computer-readable code of the screening program according to the twelfth aspect is recorded can also be exemplified as an aspect of the present invention.

In order to achieve the above-described object, according to a thirteenth aspect of the present invention, there is provided a screening device which extracts a target compound bound to a target biopolymer other than a protein from a plurality of compounds, the device comprising: a storage unit which stores a three-dimensional structure of a compound formed of a plurality of atoms and the first invariant feature quantity of the three-dimensional structure of the compound which is calculated using the feature quantity calculating method according to the second aspect in association with each other for each of the plurality of compounds; a feature quantity calculation unit which calculates the first invariant feature quantity of a binding compound that is a compound whose binding to the target biopolymer other than the protein has been confirmed; a similarity calculation unit which calculates a similarity between the first invariant feature quantity of the plurality of compounds and the first invariant feature quantity of the binding compound; and a compound extraction unit which extracts the target compound from the plurality of compounds based on the similarity.

As described above for the second aspect, in a case where the target compound and the target biopolymer other than the protein have similar first invariant feature quantities, the drug efficacies of both the target compound and the target biopolymer are similar. Therefore, according to the thirteenth aspect, a target compound having drug efficacy similar to that of the target biopolymer other than the protein is extracted based on the first invariant feature quantity so that screening of a pharmaceutical candidate compound can be efficiently performed. Further, the compound extraction unit may extract a compound having a similarity greater than or equal to the threshold or a compound in a descending order of the similarity.

In order to achieve the above-described object, according to a fourteenth aspect of the present invention, there is provided a screening device which extracts a target compound bound to a target biopolymer from a plurality of compounds, the device comprising: a storage unit which stores a three-dimensional structure of a compound formed of a plurality of atoms and the second invariant feature quantity of the three-dimensional structure of the compound which is calculated using the feature quantity calculating method according to the fourth aspect in association with each other for each of the plurality of compounds; a feature quantity calculation unit which calculates the second invariant feature quantity of a binding compound that is a compound whose binding to the target biopolymer has been confirmed; a similarity calculation unit which calculates a similarity between the second invariant feature quantity of the plurality of compounds and the second invariant feature quantity of the binding compound; and a compound extraction unit which extracts the target compound from the plurality of compounds based on the similarity.

As described above for the fourth aspect, compounds having similar second invariant feature quantities exhibit similar drug efficacies. Therefore, according to the fourteenth aspect, even in a case where a virtual probe is used, a target compound having drug efficacy similar to that of the binding compound is extracted based on the second invariant feature quantity so that screening of a pharmaceutical candidate compound can be efficiently performed. Further, the compound extraction unit may extract a compound having a similarity greater than or equal to the threshold or a compound in a descending order of the similarity.

In order to achieve the above-described object, according to a fifteenth aspect of the present invention, there is provided a compound creating method of creating a three-dimensional structure of a target compound that is bound to a target biopolymer other than a protein from a plurality of compounds, the method comprising: a storing step of storing a three-dimensional structure of a compound formed of a plurality of atoms and a first invariant feature quantity in association with each other for each of the plurality of compounds; a feature quantity calculating step of calculating the first invariant feature quantity of a binding compound that is a compound whose binding to the target biopolymer other than the protein has been confirmed using the feature quantity calculating method according to the second aspect; a generator constructing step of constructing a generator through machine learning using the three-dimensional structure of the plurality of compounds as teacher data and the first invariant feature quantity as an explanatory variable; and a compound three-dimensional structure generating step of generating a three-dimensional structure of the target compound from the first invariant feature quantity of the binding compound using the generator.

In the screening methods according to the tenth and eleventh aspects described above, a compound that is compatible with a target biopolymer other than a protein is found among a plurality of compounds whose structural formulae have already been determined (written down). Accordingly, after the feature quantity of the compound is calculated, a method of extracting the compound based on the similarity with the feature quantity of the separately calculated target biopolymer, that is, a search method is employed. Therefore, in a case where the correspondence between the structural formula of the compound and the feature quantity thereof is recorded, a structural formula having a high similarity (greater than or equal to the threshold) can be found. Meanwhile, in the fifteenth aspect, a structural formula of a compound having a feature quantity similar to the feature quantity (the first invariant feature quantity) of the target biopolymer (accordingly, the drug efficacies are similar) is generated without performing search.

The generation of the structural formula in a case where the feature quantity has been provided can be performed using a generator constructed through machine learning. Specifically, in the fifteenth aspect, a generator is constructed through machine learning (the learning method is not particularly limited) using the three-dimensional structure of the compound as teacher data and the first invariant feature quantity as an explanatory variable, and a three-dimensional structure of the target compound is generated from the first invariant feature quantity of the target biopolymer using the generator. In the fifteenth aspect, since search is not performed, the three-dimensional structure of the compound can be generated even in a case of "no solution was found as the result of screening search", and thus the three-dimensional structure of the pharmaceutical candidate compound can be efficiently created.

Further, the three-dimensional structure to be generated in the fifteenth aspect is affected by the features of the compound provided as teacher data. Therefore, by selecting the features of the compound to be provided as teacher data, a compound having a three-dimensional structure with different features can be generated. For example, a compound having a three-dimensional structure that is easily synthesized can be generated by providing a compound that is easily synthesized as teacher data.

In order to achieve the object described above, according to a sixteenth aspect of the present invention, there is provided a compound creating method of creating a three-dimensional structure of a target compound that is bound to a target biopolymer from a plurality of compounds, the method comprising: a storing step of storing a three-dimensional structure of a compound formed of a plurality of atoms and a second invariant feature quantity in association with each other for each of the plurality of compounds; a feature quantity calculating step of calculating the second invariant feature quantity of a binding compound that is a compound whose binding to the target biopolymer has been confirmed using the feature quantity calculating method according to the fourth aspect; a generator constructing step of constructing a generator through machine learning using the three-dimensional structure of the plurality of compounds as teacher data and the second invariant feature quantity as an explanatory variable; and a compound three-dimensional structure generating step of generating a three-dimensional structure of the target compound from the second invariant feature quantity of the binding compound using the generator.

According to the sixteenth aspect, similar to the fifteenth aspect, a structural formula of a compound having a feature quantity similar to the feature quantity (the second invariant feature quantity) of the binding compound (accordingly, the drug efficacies are similar) is generated without performing search, and thus the three-dimensional structure of the pharmaceutical candidate compound can be efficiently created. Further, similar to the fifteenth aspect, by selecting the features of the compound to be provided as teacher data, a compound having a three-dimensional structure with different features can be generated.

In order to achieve the above-described object, according to a seventeenth aspect of the present invention, there is provided a compound creating program which causes a computer to execute the compound creating method according to the fifteenth or sixteenth aspect. The "computer" in the seventeenth aspect can be realized using one or more of various processors such as a central processing unit (CPU). Further, a non-temporary recording medium on which a computer-readable code of the compound creating program according to the seventeenth aspect is recorded can also be exemplified as an aspect of the present invention.

In order to achieve the object described above, according to an eighteenth aspect of the present invention, there is provided a compound creating device which creates a three-dimensional structure of a target compound that is bound to a target biopolymer other than a protein from a plurality of compounds, the device comprising: a storage unit which stores a three-dimensional structure of a compound formed of a plurality of atoms and a first invariant feature quantity in association with each other for each of the plurality of compounds; a feature quantity calculation unit which calculates the first invariant feature quantity of a binding compound that is a compound whose binding to the target biopolymer other than the protein has been confirmed using the feature quantity calculating method according to the second aspect; a generator construction unit which constructs a generator through machine learning using the three-dimensional structure of the plurality of compounds as teacher data and the first invariant feature quantity as an explanatory variable; and a compound three-dimensional structure generation unit which generates a three-dimensional structure of the target compound from the first invariant feature quantity of the binding compound using the generator.

According to the eighteenth aspect, similar to the fifteenth or sixteenth aspect, a structural formula of a compound having a feature quantity similar to the feature quantity (the first invariant feature quantity) of the binding compound (accordingly, the drug efficacies are similar) is generated without performing search, and thus the three-dimensional structure of the pharmaceutical candidate compound can be efficiently created. Further, similar to the fifteenth or sixteenth aspect, by selecting the features of the compound to be provided as teacher data, a compound having a three-dimensional structure with different features can be generated.

In order to achieve the above-described object, according to a nineteenth aspect of the present invention, there is provided a compound creating device which creates a three-dimensional structure of a target compound that is bound to a target biopolymer from a plurality of compounds, the device comprising: a storage unit which stores a three-dimensional structure of a compound formed of a plurality of atoms and a second invariant feature quantity in association with each other for each of the plurality of compounds; a feature quantity calculation unit which calculates the second invariant feature quantity of a binding compound that is a compound whose binding to the target biopolymer has been confirmed using the feature quantity calculating method according to the fourth aspect; a generator construction unit which constructs a generator through machine learning using the three-dimensional structure of the plurality of compounds as teacher data and the second invariant feature quantity as an explanatory variable; and a compound three-dimensional structure generation unit which generates a three-dimensional structure of the target compound from the second invariant feature quantity of the binding compound using the generator.

According to the nineteenth aspect, similar to the fifteenth or sixteenth aspect, a structural formula of a compound having a feature quantity similar to the feature quantity (the second invariant feature quantity) of the binding compound (accordingly, the drug efficacies are similar) is generated without performing search, and thus the three-dimensional structure of the pharmaceutical candidate compound can be efficiently created. Further, similar to the fifteenth or sixteenth aspect, by selecting the features of the compound to be provided as teacher data, a compound having a three-dimensional structure with different features can be generated.

As described above, according to the feature quantity calculating method, the feature quantity calculating program, and the feature quantity calculating device of the present invention, it is possible to calculate a feature quantity that accurately shows chemical properties of a target structure. Further, according to the screening method, the screening program, and the screening device of the present invention, screening of a pharmaceutical candidate compound can be efficiently performed. Further, according to the compound creating method, compound creating program, and compound creating device of the present invention, it is possible to efficiently create a three-dimensional structure of a pharmaceutical candidate compound.

BRIEF DESCRIPTION OF THE DRAWINGS

FIG. 8 is a table showing an example of a three-dimensional AAM feature quantity.

FIG. 13 is a graph showing easiness of finding a hit in a case where an invariant AAM descriptor is used.

FIGS. 17A and 17B are tables showing an example of a result of extracting a target compound based on the similarity of descriptors.

FIGS. 19A and 19B are other tables showing an example of a result of extracting a target compound based on the similarity of the descriptor.

FIG. 24 is a diagram showing a state of generating a three-dimensional structure using a result of machine learning.

FIG. 25 is a graph showing a relationship between the number of interlayers and the cos similarity.

FIGS. 26A and 26B are diagrams showing an example of generating a three-dimensional structure.

FIG. 33 is a still another diagram showing a comparison result of easiness of finding a hit.

DESCRIPTION OF THE PREFERRED EMBODIMENTS

Hereinafter, embodiments of a feature quantity calculating method, a screening device, and a compound creating device of the present invention will be described in detail with reference to the accompanying drawings.

First Embodiment

Figure 1:
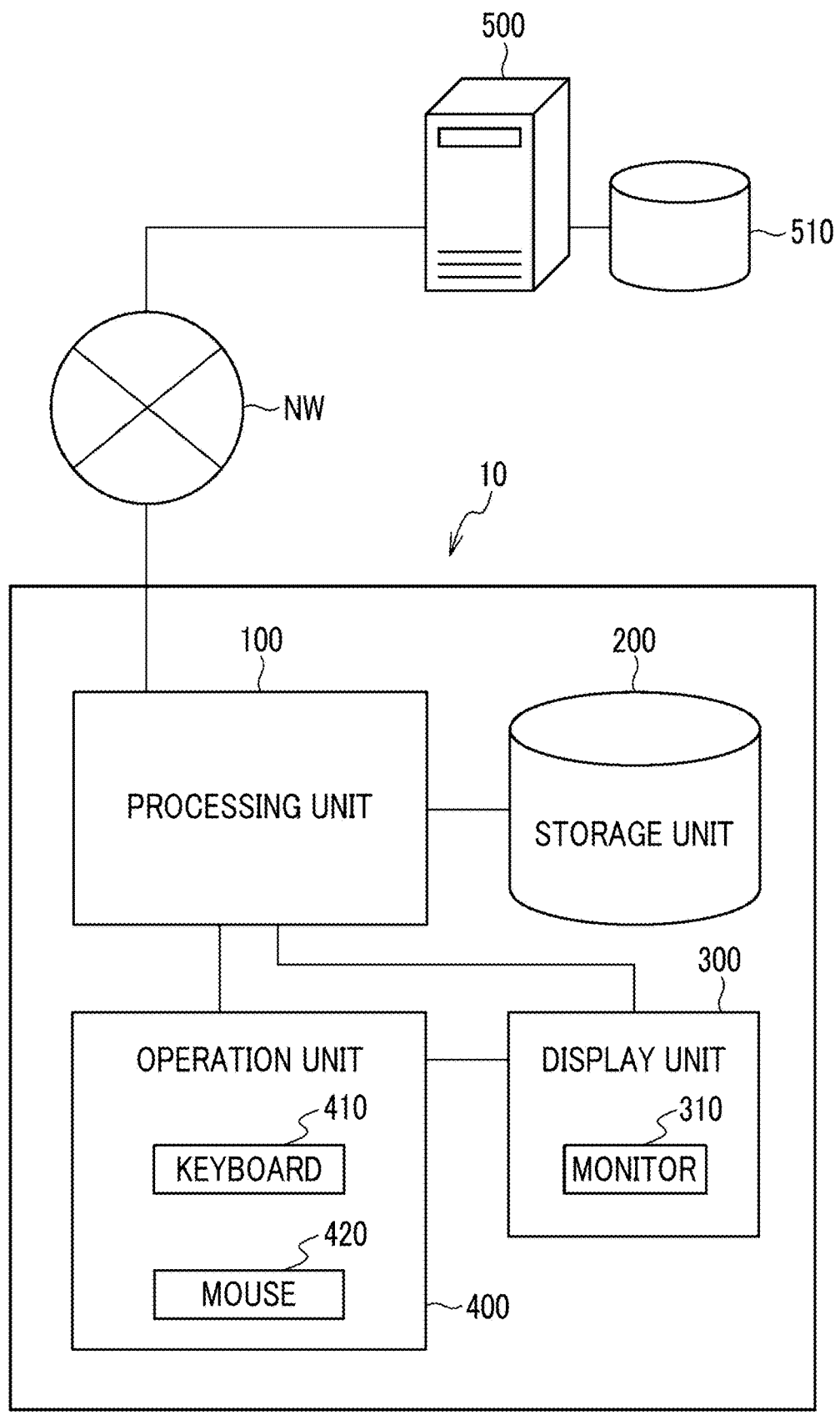
FIG. 1 is a block diagram showing a configuration of a screening device according to a first embodiment.

FIG. 1 is a block diagram showing a configuration of a screening device 10 (a feature quantity calculating device or a screening device) according to a first embodiment. The screening device 10 is a device that calculates a feature quantity of a compound (target structure) and/or a pocket structure (target structure) and extracts (screens) a target compound, and can be realized using a computer. As shown in FIG. 1, the screening device 10 includes a processing unit 100, a storage unit 200, a display unit 300, and an operation unit 400, and these units are connected to one another to transmit and receive necessary information. These constituent elements may be installed by employing various installation forms. Respective constituent elements may be installed in one site (in one housing, one room, or the like) or may be installed in places separated from each other and connected via a network. Further, the screening device 10 is connected to an external server 500 and an external database 510 such as a Protein Data Bank (PDB) via a network NW such as the Internet, and information related to structural formulae of compounds and crystal structures of proteins can be obtained as necessary.

<Configuration of Processing Unit>

Figure 2:
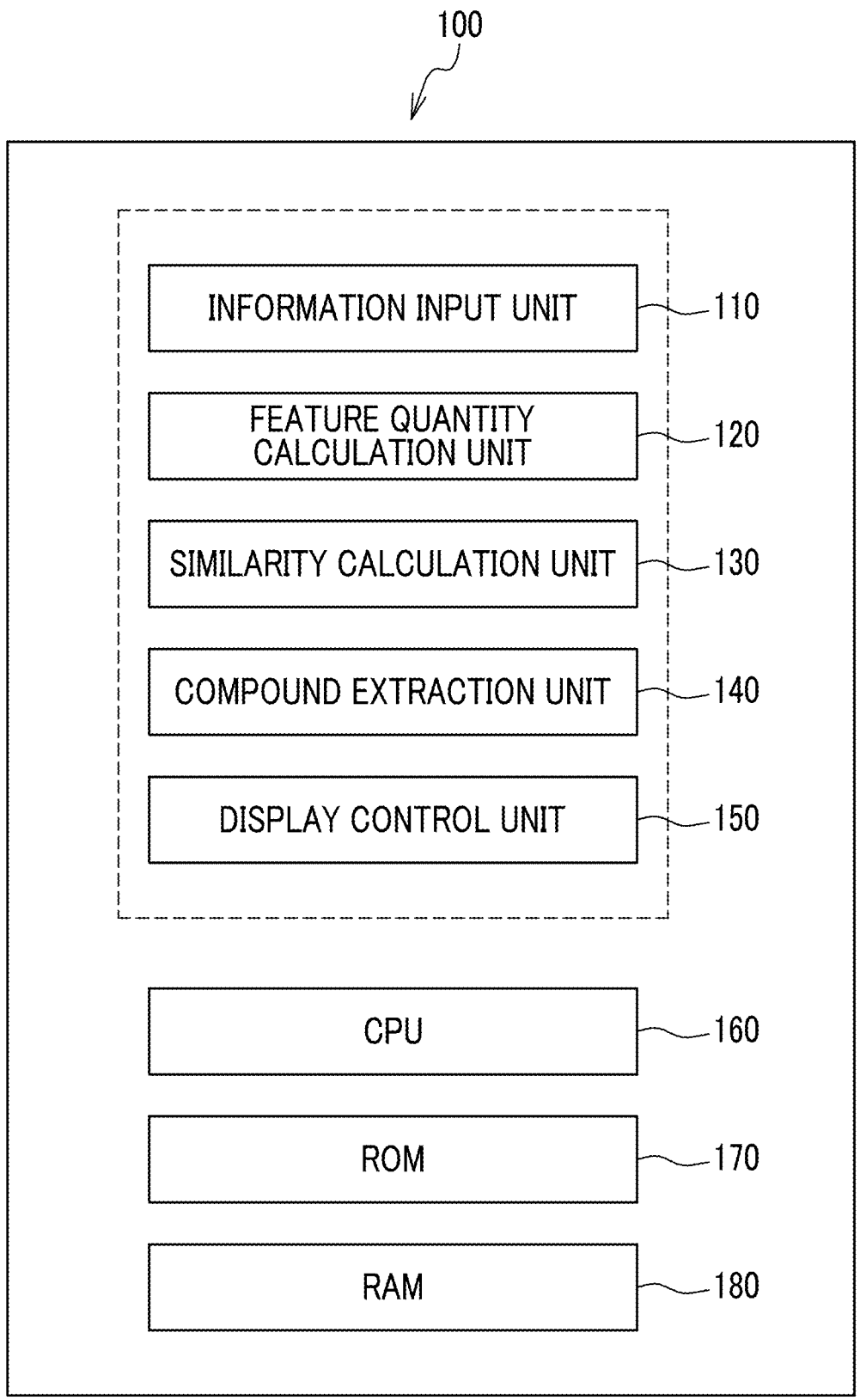
FIG. 2 is a block diagram showing a configuration of a processing unit.

FIG. 2 is a diagram showing a configuration of the processing unit 100. The processing unit 100 includes an information input unit 110, a feature quantity calculation unit 120, a similarity calculation unit 130, a compound extraction unit 140, a display control unit 150, a CPU 160 (CPU: Central Processing Unit), a ROM 170 (ROM: Read Only Memory), and a RAM 180 (Random Access Memory).

The information input unit 110 inputs information related to a structural formula of a compound, an X crystal structure of a target protein, and a pocket position via a recording medium interface such as a DVD drive (not shown) or a semiconductor memory terminal and/or a network NW. The feature quantity calculation unit 120 (the target structure designation unit, the three-dimensional structure generation unit, the feature quantity calculation unit, and the invariant conversion unit) calculates feature quantities (a first feature quantity, a first invariant feature quantity, a second feature quantity, a second invariant feature quantity, a third feature quantity, and a third invariant feature quantity) according to the present invention. The similarity calculation unit 130 (the similarity calculation unit) calculates the similarity between the calculated feature quantities. The compound extraction unit 140 (the compound extraction unit) extracts a target compound from a plurality of compounds based on the similarity. The display control unit 150 controls input information and display of the process result on the monitor 310. The process of calculation of the feature quantity and screening of the target compound using these functions of the processing unit 100 will be described below in detail. Further, the process using these functions is performed under the control of the CPU 160.

The function of each unit of the processing unit 100 described above can be realized using various processors. Various processors include a CPU that is a general-purpose processor that executes software (program) to realize various functions. Further, the various processors described above include a graphics processing unit (GPU) serving as a processor specialized in image processing and a programmable logic device (PLD) serving as a processor that can change the circuit configuration after manufacture of a field programmable gate array (FPGA). Further, the above-described various processors include an exclusive electric circuit serving as a processor having a circuit configuration designed exclusively for executing a specific process such as an application specific integrated circuit (ASIC).

The functions of each unit may be realized by one processor, or may be realized by a plurality of same or different processors (for example, a plurality of FPGAs, a combination of a CPU and an FPGA, or a combination of a CPU and a GPU). Further, a plurality of functions may be realized by one processor. As an example in which a plurality of functions are configured by one processor, first, as represented by a computer such as a client or a server, a form of one processor which is configured by a combination of one or more CPUs and software and can be realized as a plurality of functions is exemplified. Second, as represented by a system-on-chip (SoC) or the like, there is a form in which a processor that realizes the functions of the entire system by one integrated circuit (IC) chip is used. As described above, various functions are configured using one or more of the above-described various processors as a hardware structure. Further, the hardware structure of these various processors is more specifically an electric circuit (circuitry) in which circuit elements such as semiconductor elements are combined.

In a case where the above-described processor or electric circuit executes software (program), a code that can be read by the computer (for example, various processors or electric circuits constituting the processing unit 100, and/or a combination thereof) to execute the software is stored in a non-temporary recording medium such as a ROM 170 (see FIG. 2), and the processor refers to the software. The software stored in the non-temporary recording medium includes the feature quantity calculating method and a program (a feature quantity calculating program and a screening program) for executing a target compound extraction process according to the present invention. The code may be recorded on non-temporary recording media such as various magneto-optical recording devices and semiconductor memories instead of the ROM 170. During the process using software, for example, the RAM 180 is used as a temporary storage area, and the data stored in, for example, an electronically erasable and programmable read only memory (EEPROM) (not shown) can also be referred to.

<Configuration of Storage Unit>

Figure 3:
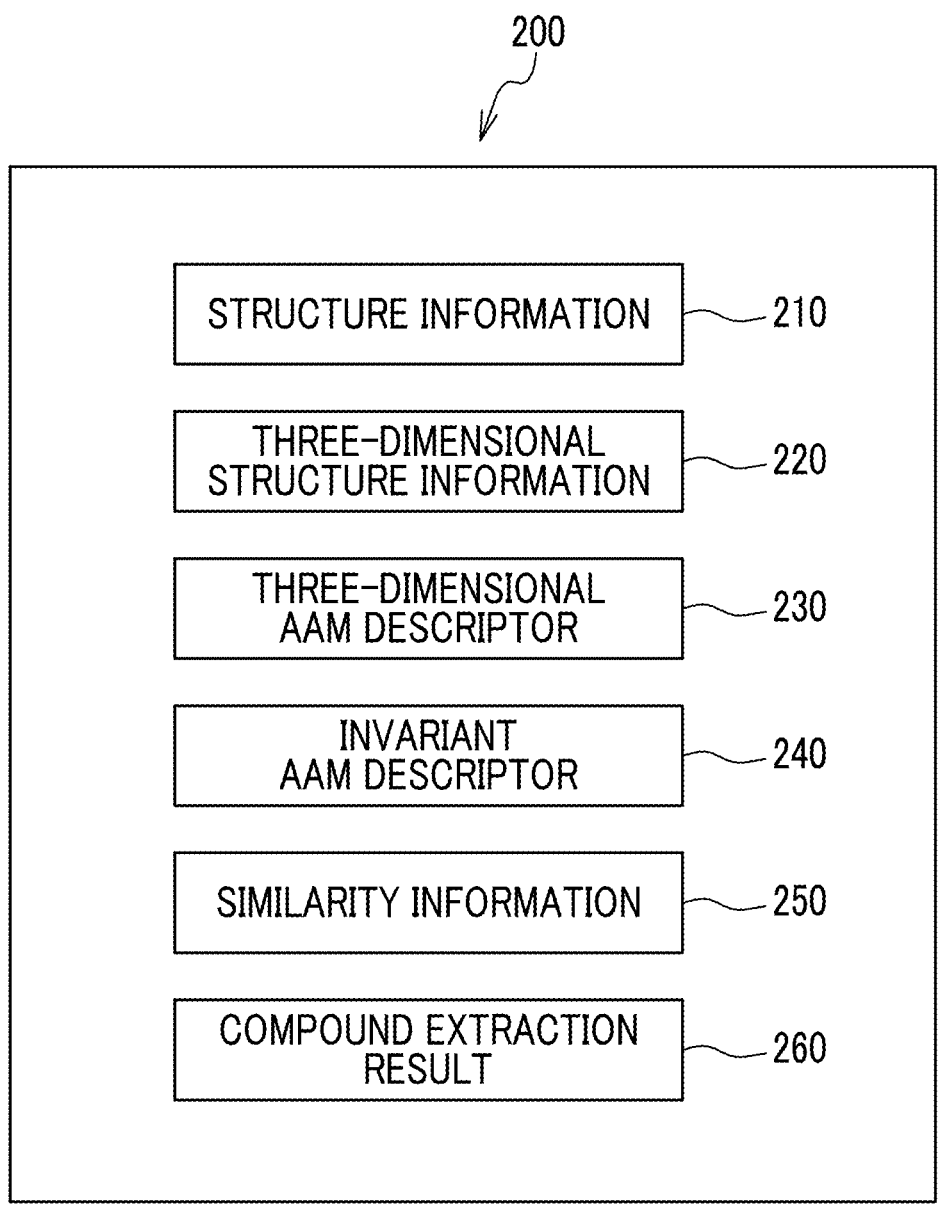
FIG. 3 is a diagram showing information stored in a storage unit.

The storage unit 200 is formed of non-temporary recording media such as a digital versatile disk (DVD), a hard disk, and various semiconductor memories and control units thereof and stores images and information shown in FIG. 3. Structure information 210 includes the structural formula of the compound, the three-dimensional structure of the target protein, and the position of the pocket. Three-dimensional structure information 220 is information related to the three-dimensional structure of the compound and/or the pocket structure generated from the structure information 210. A three-dimensional AAM descriptor 230 is a feature quantity obtained by quantifying, in a three-dimensional space, the degree of accumulation of one or more kinds of amino acids in the periphery of the three-dimensional structure of the compound or the pocket structure, and is calculated according to the feature quantity calculating method described below. Further, "AAM" stands for "Amino Acid Mapping". An invariant AAM descriptor 240 is a feature quantity obtained by converting the three-dimensional AAM descriptor 230 into an invariant with respect to rotation and translation of the compound or the pocket structure. Similarity information 250 is information related to the similarity between the feature quantities, and a compound extraction result 260 is information related to the target compound extracted based on the similarity.

Figure 4:
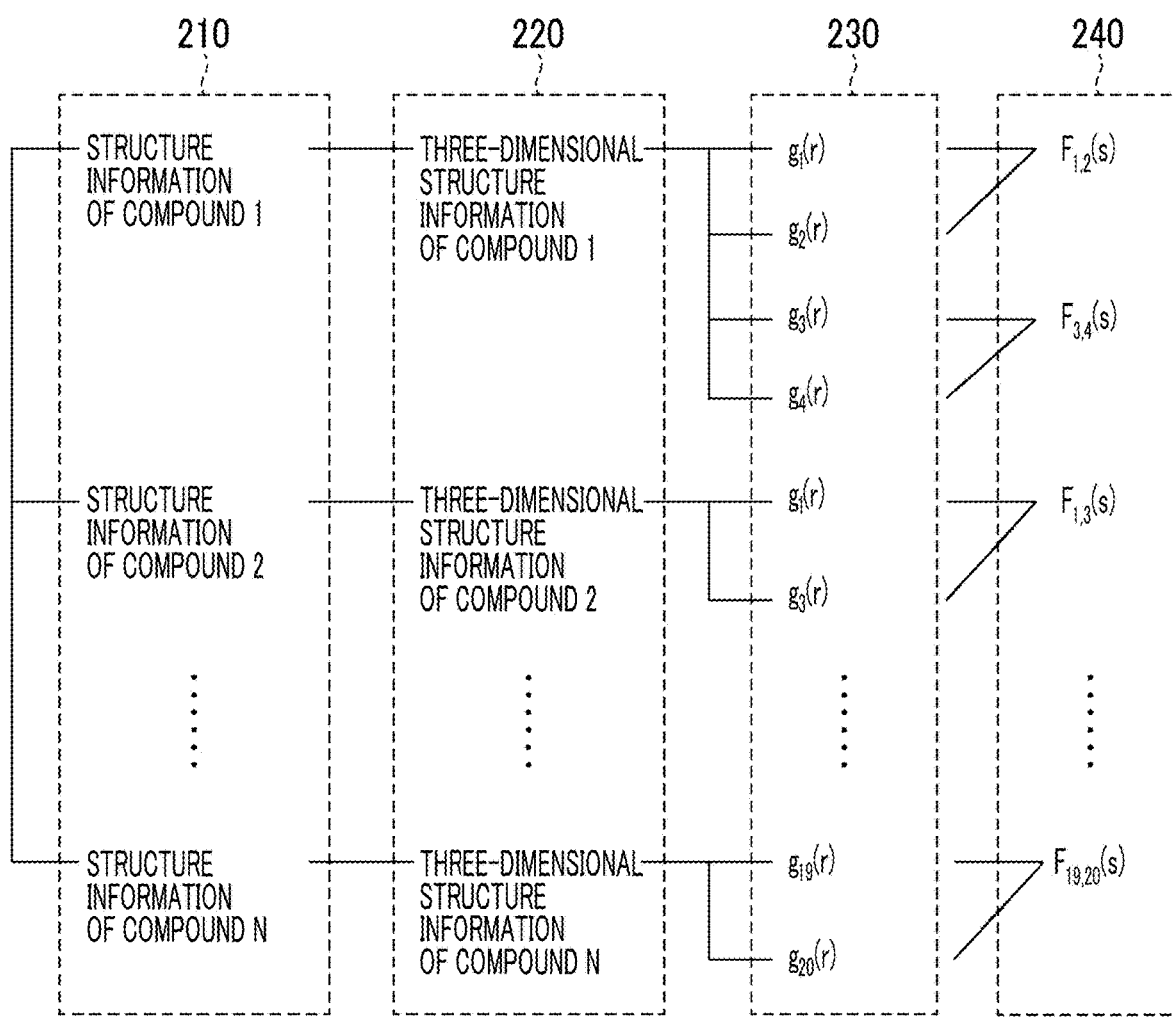
FIG. 4 is a diagram showing a state in which structure information of a compound and a feature quantity thereof are stored in association with each other.

FIG. 4 shows a state in which the structure information 210, the three-dimensional structure information 220, the three-dimensional AAM descriptor 230, and the invariant AAM descriptor 240 are associated with one another and stored in the storage unit 200 for N compounds (N represents an integer of 2 or greater). In FIG. 4, for example, a structural formula can be used as the structure information 210, and a three-dimensional structural formula (described below) can be used as the three-dimensional structure information 220. In FIG. 4, the three-dimensional AAM descriptor 230 (described as "$g_a(r)$"; a is a subscript indicating the kind of amino acid) and the invariant AAM descriptor 240 (described as "$F_{ab}(s)$"; a and b are subscripts indicating the kinds of amino acids) corresponding to the three-dimensional AAM descriptor 230 for each of twenty kinds of amino acids for each compound are stored in association with each other. The three-dimensional AAM descriptor 230 and the invariant AAM descriptor 240 may be stored not for all twenty kinds of amino acids but for some amino acids according to the number of descriptors used for screening.

A plurality of sets (libraries) of information as shown in FIG. 4 may be stored in the storage unit 200. FIG. 4 shows a state in which information related to compounds is stored, and information related to target proteins can be stored with the same configuration. Further, a method for calculating a three-dimensional AAM descriptor and/or an invariant AAM descriptor using such structure information and three-dimensional structure information will be described below.

<Configuration of Display Unit and Operation Unit>

The display unit 300 includes the monitor 310 (display device) and can display input images, images and information stored in the storage unit 200, results of the process carried out by the processing unit 100, and the like. The operation unit 400 includes a keyboard 410 and a mouse 420 as an input device and/or a pointing device, and execution of the feature quantity calculating method according to the present invention and the operation required for extraction of the target compounds can be performed by a user through these devices and the screen of the monitor 310 (described later). The operations that can be performed by the user include, for example, a processing mode, the kind of descriptor to be calculated, a descriptor used for screening, and designation of a threshold with respect to the similarity, <Process in Screening Device>

In the screening device 10 with the above-described configuration, calculation of a feature quantity (descriptor) and/or extraction of a target compound can be performed according to the user's instruction via the operation unit 400. Hereinafter, the details of each process will be described.

<Calculation of Feature Quantity>

The screening device 10 is capable of calculating a three-dimensional AAM descriptor and/or an invariant AAM descriptor according to the user's instruction via the operation unit 400.

<Calculation of Three-Dimensional AAM Descriptor for Compound>

Figure 5:
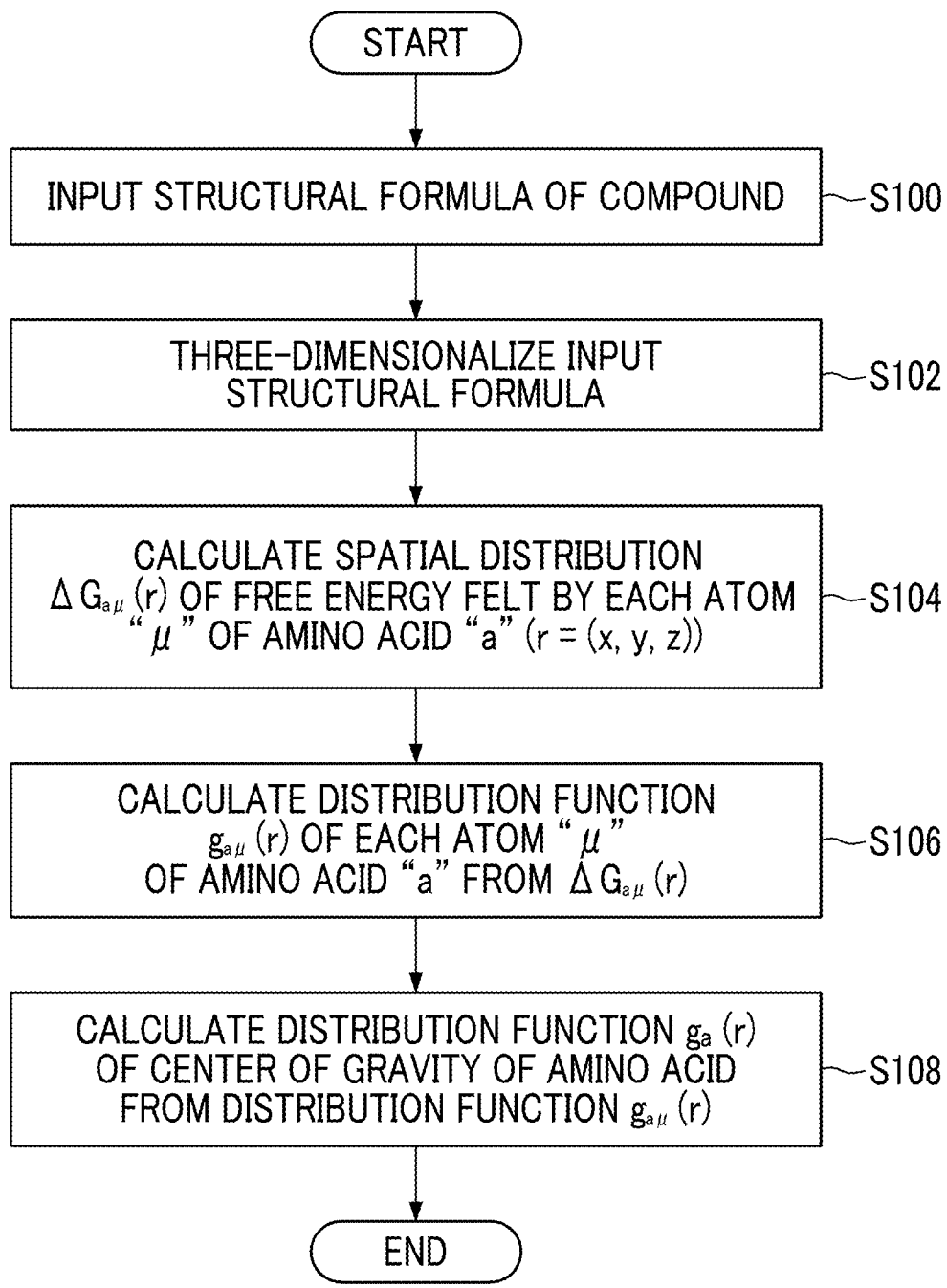
FIG. 5 is a flowchart showing a procedure for calculating a three-dimensional AAM feature quantity of a compound.

FIG. 5 is a flowchart showing a procedure for calculating a three-dimensional AAM descriptor for a compound (target structure). The ligand is a compound whose binding to the target protein has been confirmed, and the three-dimensional AAM descriptor can be calculated according to the procedure of FIG. 5. In Step S100, the information input unit 110 inputs a structural formula of a compound according to an operation by the user. In this manner, the compound represented by the input chemical formula is designated as the target structure (target structure designating step).

Figure 6A:
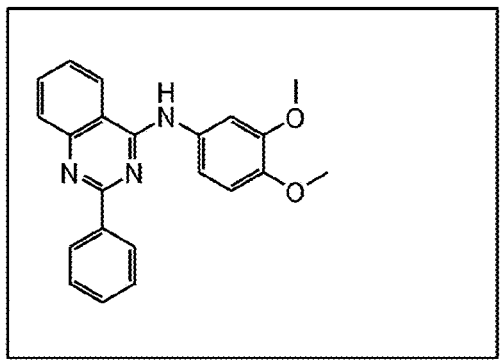
FIGS. 6A and 6B are diagrams showing an example of three-dimensionalization of a structural formula.
Figure 6B:
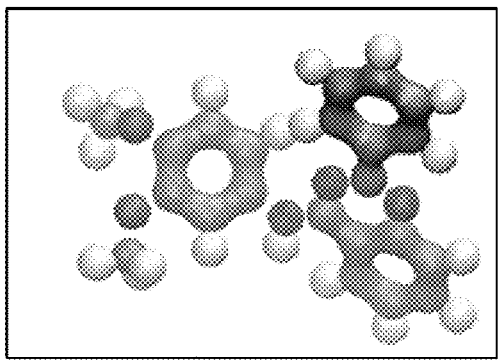

The feature quantity calculation unit 120 three-dimensionalizes the input structural formula to generate a three-dimensional structure of a compound formed of a plurality of atoms (a plurality of unit structures having chemical properties) (Step S102: a three-dimensional structure generating step). Various methods are known for three-dimensionalization of a structural formula, and the present invention is not particularly limited to the method used in Step S102. FIGS. 6A and 6B show an example of a three-dimensional structural formula. FIG. 6A shows an input structural formula and FIG. 6B shows a three-dimensionalized structural formula.

The feature quantity calculation unit 120 calculates a spatial distribution $\Delta G_{a\mu}(r)$ of free energy felt by each atom "$\mu$" of an amino acid "a" (a represents a number representing the kind of amino acid; 1 to 20) (Step S104; feature quantity calculating step). As a method of calculating $\Delta G_{a\mu}(r)$, a molecular dynamics (MD) method can be employed, but the present invention is not limited thereto. The amino acid for calculating the feature quantity may be a predetermined kind of amino acid or may be determined according to the user's instruction (one or more kinds of amino acids may be used, and a plurality of kinds of amino acids may also be used).

The feature quantity calculation unit 120 calculates a distribution function $g_{a\mu}(r)$ of each atom "$\mu$" of the amino acid "a" from $\Delta G_{a\mu}(r)$ (Step S106: feature quantity calculating step). $g_{a\mu}(r)$ is represented by Equation (1) in a case where T is set as room temperature and $K_B$ is set as a Boltzmann constant.

$$g_{a\mu}(r) = \exp(-\Delta G_{a\mu}(r)/K_B T) \quad (1)$$

The feature quantity calculation unit 120 calculates a distribution function $g_{a\mu}(r)$ of the center of gravity of an amino acid from the distribution function $g_{a\mu}(r)$ (Step S108: feature quantity calculating step). For the calculation, $g_{a\mu}(r)$ is geometrically averaged for each atom "$\mu$". This distribution function $g_a(r)$ is a three-dimensional AAM descriptor obtained by quantifying, in a three-dimensional space, the degree of accumulation of one or more kinds of amino acids "a" in the periphery of the three-dimensional structure of the compound. The feature quantity calculation unit 120 stores the calculated three-dimensional AAM descriptor in the storage unit 200 as the three-dimensional AAM descriptor 230 in association with the structure information (structure information 210) and the three-dimensional structure information (three-dimensional structure information 220) of the compound. (See FIG. 4).

Figure 7A:
FIGS. 7A and 7B are diagrams showing an example of a three-dimensional AAM feature quantity.
Figure 7B:
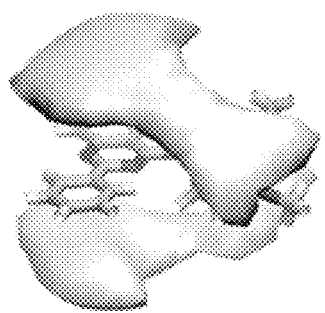

FIGS. 7A and 7B are an example of a three-dimensional AAM descriptor of the compound shown in FIGS. 6A and 6B. FIG. 7A shows a three-dimensional AAM descriptor of alanine, and FIG. 7B shows a three-dimensional AAM descriptor of valine. In FIGS. 7A and 7B, the dark region is a region where the degree of accumulation of amino acids (existence probability) is high. FIG. 8 is a table showing another example of the three-dimensional AAM descriptor of the compound shown in FIGS. 6A and 6B, and the three-dimensional AAM descriptor is shown in a direction 1, a direction 2, and a direction 3 (the first, second, and third rows of the table, respectively) which are different from one another. The left columns of the table show the three-dimensional AAM descriptor (the level surface with respect to the threshold), and the right columns of the table show the three-dimensional AAM descriptor (the level surface with respect to the threshold) and the three-dimensional structure of the compound.

<Calculation of Three-Dimensional AAM Descriptor for Pocket Structure>

Figure 9:
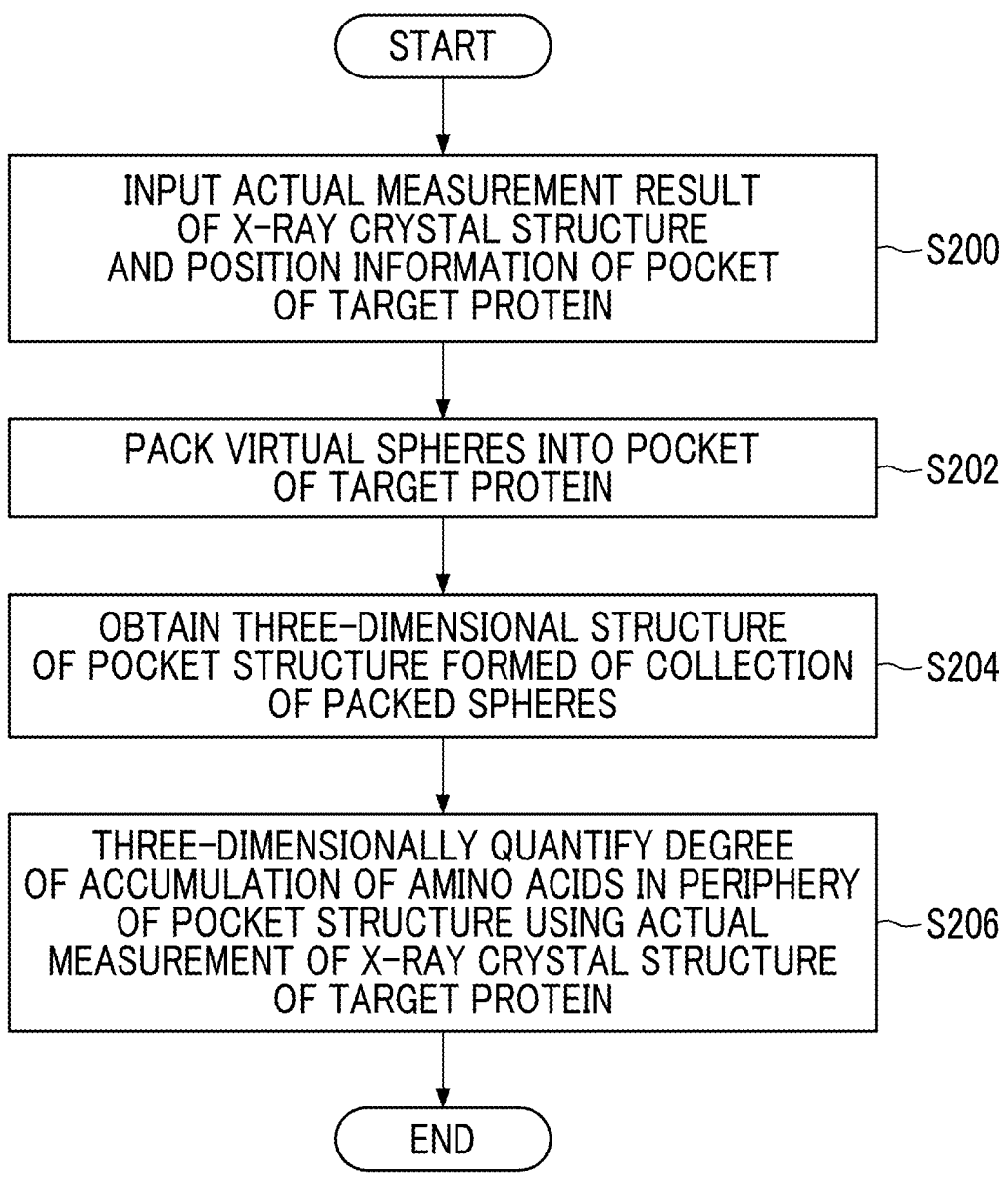
FIG. 9 is a flowchart showing a procedure for a three-dimensional AAM descriptor for a pocket structure.
Figure 10A:
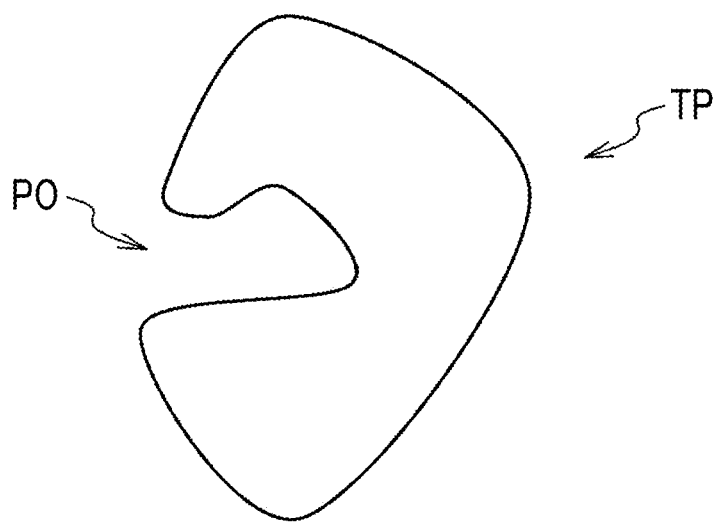
FIGS. 10A to 10C are conceptual views showing a state of a three-dimensional AAM descriptor for a pocket structure.
Figure 10B:
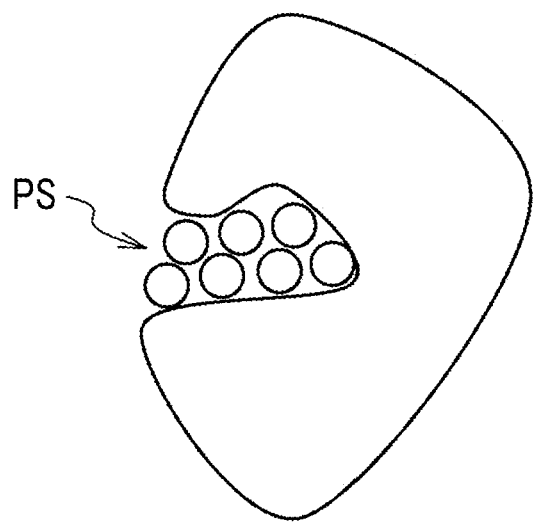
Figure 10C:
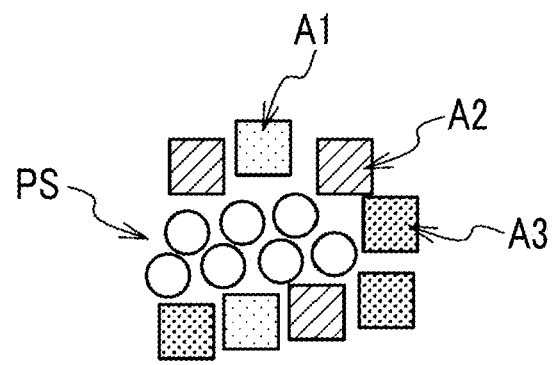

In the screening device 10, a pocket structure that is bound to a target protein instead of a compound is designated as a target structure, and the feature quantity (the three-dimensional AAM descriptor) of this pocket structure can be calculated. The pocket structure is a target structure that is bound to a pocket, which is an active site of the target protein, and the "active site" indicates a site where the activity of the target protein is promoted or suppressed by the binding of the pocket structure. FIG. 9 is a flowchart showing a procedure for calculating the three-dimensional AAM descriptor for the pocket structure. FIGS. 10A to 10C are conceptual views showing a state of the three-dimensional AAM descriptor for the pocket structure.

In the flowchart of FIG. 9, the information input unit 110 inputs the actual measurement result of the three-dimensional structure of the target protein and the position information of the pocket (Step S200: target structure designating step). FIG. 10A shows a pocket PO in a target protein TP. The pocket structure is designated as the target structure by the process of Step S200.

The feature quantity calculation unit 120 packs a plurality of virtual spheres (a plurality of unit structures having chemical properties) into the pocket of the target protein (Step S202: the target structure designating step or the three-dimensional structure generating step). The "virtual sphere" can be considered to have chemical properties such as a van der Waals radius and an electric charge, and "packing the virtual spheres" can be performed by simulation (for example, a molecular dynamics method). A collection of the packed virtual spheres (three-dimensional structure) can be obtained as a three-dimensional structure of the pocket structure (target structure) in Step S202 (Step S204: three-dimensional structure generating step). FIG. 10B shows an example of a pocket structure PS of the target protein TP.

The feature quantity calculation unit 120 three-dimensionally quantifies the degree of accumulation of one or more kinds of amino acids in the periphery of the pocket structure using actual measurement of the three-dimensional structure of the target protein (Step S206: feature quantity calculating step). Practically, it is possible to read out what kinds of amino acids are accumulated in the periphery of the pocket structure. FIG. 10C shows that three kinds of amino acids A1, A2, and A3 are accumulated in the periphery of the pocket structure PS. Further, the number of amino acids for quantifying the degree of accumulation may he one or more (a plurality of kinds of amino acids may be used). In addition, a predetermined kind of amino acid may be quantified or an amino acid which has been set according to the operation of the user may be quantified. The feature quantity calculation unit 120 stores the calculated three-dimensional AAM descriptor in the storage unit 200 as the three-dimensional AAM descriptor 230 in association with the structure information (structure information 210) and the three-dimensional structure information (three-dimensional structure information 220) of the compound (see FIGS. 3 and 4; the storing step). In a case where the invariant AAM descriptor described below has been calculated, the feature quantity calculation unit 120 associates the three-dimensional AAM descriptor with the invariant AAM descriptor.

<Conversion of Three-Dimensional AAM Descriptor into Invariant>

The above-described three-dimensional AAM descriptor indicates the degree of three-dimensional accumulation of amino acids. However, in a case where shift or rotation of the center of gravity occurs even though the compounds are the same as each other, the value changes and the data capacity is large because the information is three-dimensional information. Therefore, in the screening device 10 according to the first embodiment, "an invariant AAM descriptor obtained by converting the three-dimensional AAM descriptor into an invariant with respect to rotation and translation of the compound" (the invariant feature quantity) can be calculated in addition to or instead of the three-dimensional AAM descriptor. Further, conversion into an invariant can be performed according to the same procedures in both cases of a compound and a pocket structure. In a case where a three-dimensional AAM descriptor of a compound is used, an invariant AAM descriptor of the compound is obtained. Further, in a case where a three-dimensional AAM descriptor of the pocket structure is used, an invariant AAM descriptor of the pocket structure is obtained.

The feature quantity calculation unit 120 (invariant conversion unit) calculates $f_a(k)$ using Fourier transform as shown in Equation (2) (invariant conversion step). As described above, "a" is a subscript (1 to 20) indicating the kind of amino acid. Further, "i" is an imaginary unit.

$$f_a(k)=\int d^3r(g_n(r)-1)e^{ikr} \quad (2)$$

The feature quantity calculation unit 120 is capable of calculating $F_{ab}(s)$ (invariant feature quantity) that is an invariant AAM descriptor using the $f_a(k)$ according to Equation (3) (invariant conversion step). In Equation (3), an invariant AAM descriptor is calculated by angular integration of a correlation function using three-dimensional AAM descriptors ($g_a(r)$ and $g_b(r)$) of two different kinds of amino acids (denoted by "a" and "b"). Further, the combination of the two kinds of amino acids used for calculation of the invariant AAM descriptors among twenty kinds of amino acids is not particularly limited.

$$F_{ab}(s)=\int d^3k f_a(-k)f_b(+k)\delta(k^2-s) \quad (3)$$

In Equation (3), a delta function is used for conversion into an invariant. However, as shown in Equation (4), conversion into an invariant can be performed using an optional function ($h(k^2-s)$).

$$F_{ab}(s)=\int d^3k f_a(-k)f_b(+k)h(k^2-s) \quad (4)$$

Figure 11A:
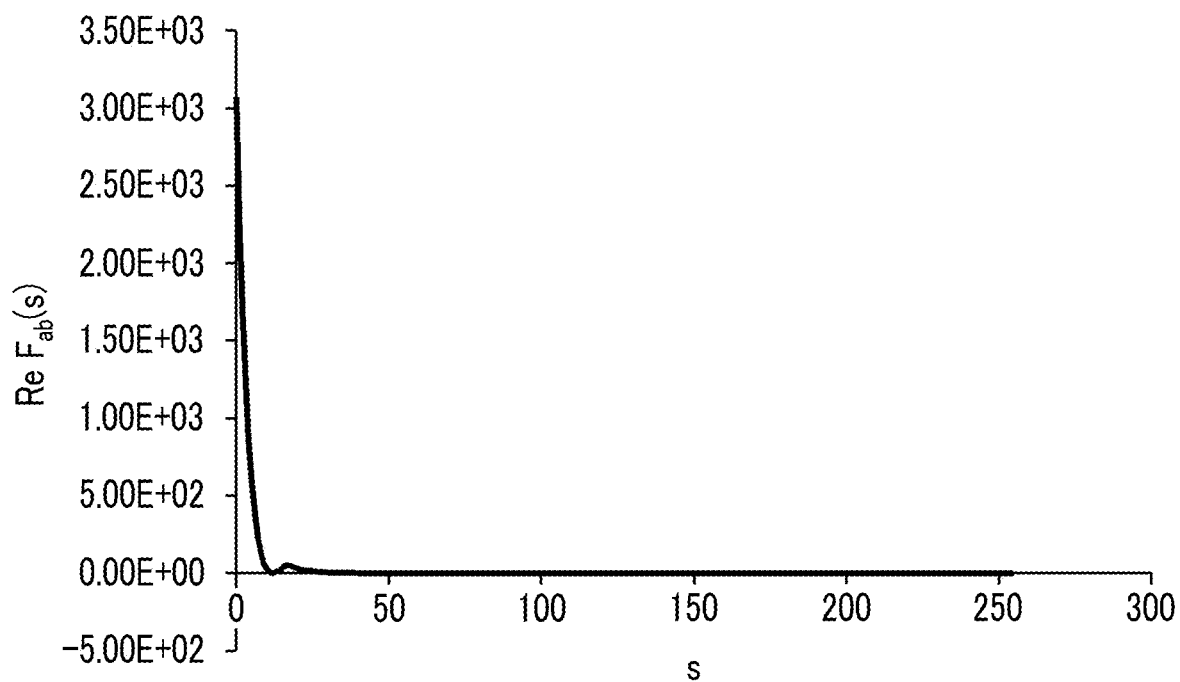
FIGS. 11A and 11B are graphs showing an example of an invariant AAM descriptor.
Figure 11B:
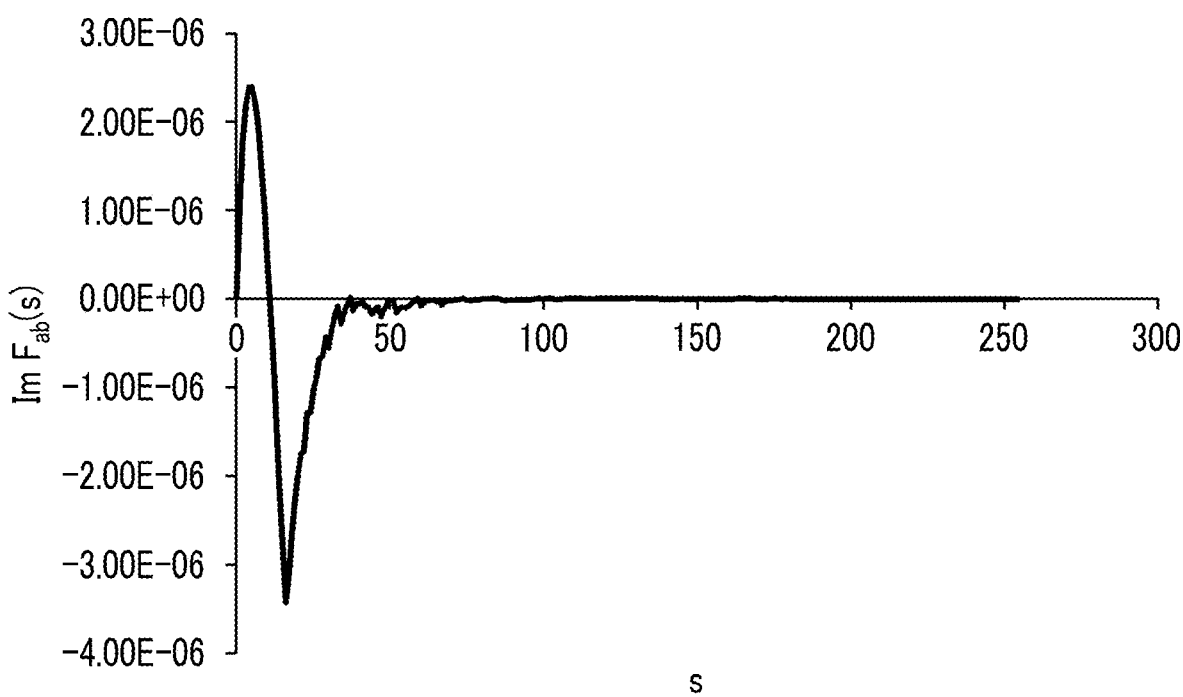

FIGS. 11A and 11B show an example of the invariant AAM descriptor calculated in the above-described manner. FIG. 11A shows a real part of $F_{12}(s)$ (an invariant AAM descriptor of amino acids 1 and 2), which is an invariant AAM descriptor, and FIG. 11B shows an imaginary part. In this manner, the conversion into an invariant can be performed while information related to the interaction between amino acids is maintained by performing conversion into an invariant using a three-dimensional AAM descriptor of two different kinds of amino acids so that compound comparison (drug efficacy determination) based on the feature quantities (the invariant feature quantities) can be accurately performed.

The feature quantity calculation unit 120 stores the calculated invariant AAM descriptor in the storage unit 200 as the invariant AAM descriptor 240 in association with the structure information (structure information 210), the three-dimensional structure information (three-dimensional structure information 220), and the original three-dimensional AAM descriptor 230 of the compound (see FIGS. 3 and 4; the storing step). In the first embodiment, since the invariant AAM descriptor is calculated using the three-dimensional AAM descriptor of two different kinds of amino acids, a plurality of associations between the three-dimensional AAM descriptor and the invariant AAM descriptor may be present.

<Evaluation of Effectiveness of Invariant AAM Descriptor>

The effectiveness of the invariant AAM descriptor calculated by the above-described process will be described.

<Example of Activity of Compound Having Similar Invariant AAM Descriptor>

Figure 12A:
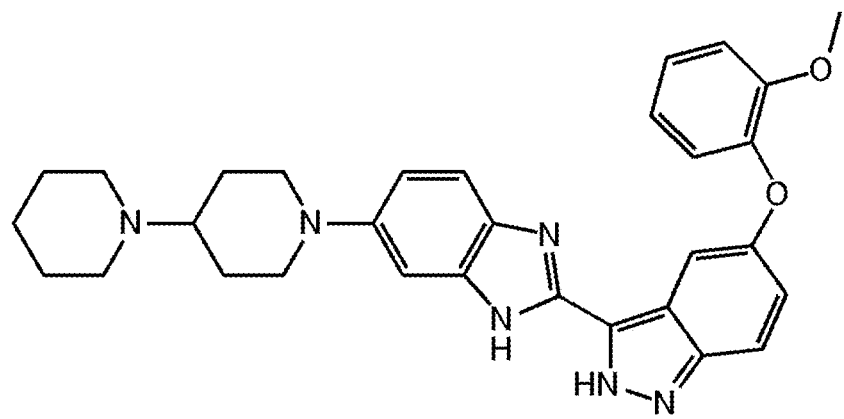
FIGS. 12A and 12B show an example of compounds with similar invariant AAM descriptors.
Figure 12B:
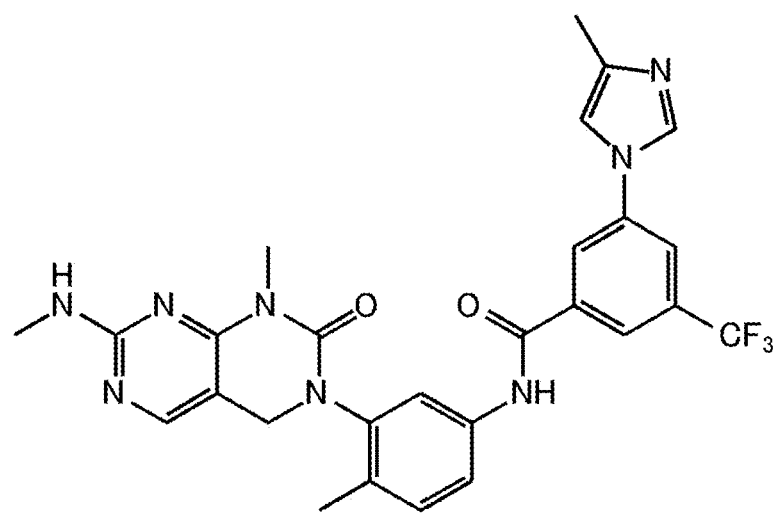

FIG. 12A shows a structural formula of a ligand for a protein ABL1 (an example of a target protein). The binding force of this ligand is at a level of 1 μM with an IC50 (50% inhibitory concentration). Meanwhile, FIG. 12B shows a structural formula of a compound having almost the same invariant AAM descriptor as that of the ligand. In a case where the activity of this compound is actually measured, the activity is at the same level as that of the ligand. That is, FIGS. 11A and 11B are an example showing that compounds having similar invariant AAM descriptors have similar drug efficacies. As described above, according to the first embodiment, a feature quantity (invariant AAM descriptor) accurately showing the chemical properties of the target structure can be obtained.

<Easiness of Finding Hits>

The easiness of finding hits using invariant AAM descriptors is evaluated according to the following procedures 1 to 5.

(Procedure 1) X hit compounds and Y non-hit compounds are mixed with a certain protein (target protein).
(Procedure 2) Invariant AAM descriptors of all (X+Y) compounds are calculated.
(Procedure 3) The similarity of each descriptor is calculated.
(Procedure 4) The (X+Y) compounds are divided into teams based on the similarities of the invariant AAM descriptors.
(Procedure 5) It is checked whether the teams in which hits are collected are mechanically generated.

As a result of division of 10,933 compounds having 183 hits (a hit content of 1.6%) for the protein ABL1 (kinase) into teams by according to the above-described procedures, the number of teams is 221. A certain team contains 16 hits and 14 other compounds, and the hit content is 53.3%. Further, this team also contains the compound shown in FIG. 12A and the compound shown in FIG. 12B. In a case where the fingerprint, which is a descriptor of the related art, is used, the similarity of these compounds is 25%. It is recognized as not being a hit even though it is a hit originally. As described above, in a case where the invariant AAM descriptor according to the first embodiment of the present invention is used in the above-described team, it was found that hits which are not collected in a case of using the fingerprint belong to the same team.

FIG. 13 shows the results of acquiring the easiness of finding hits (=expectation value; number of hits×hit content) for each of the 221 teams described above. For comparison, the result obtained in a case where the teams are randomly divided and the result obtained in a case where teams are divided using the fingerprint are shown. Based on these results, it was found that in a case where the invariant AAM descriptor is used for the above-described compound group, teams having hits more than the hits of the randomly divided teams or the teams divided using the fingerprint are generated. In FIG. 13, the team numbers vary depending on the team division method (random, the invariant AAM descriptor, the fingerprint), and thus the superiority of the team division is determined not by comparing the expectation values with the same team number but by verifying "whether teams with high expectation values (having more hits) are included or not".

<Hit Search Time (Part 1)>

Figure 14:
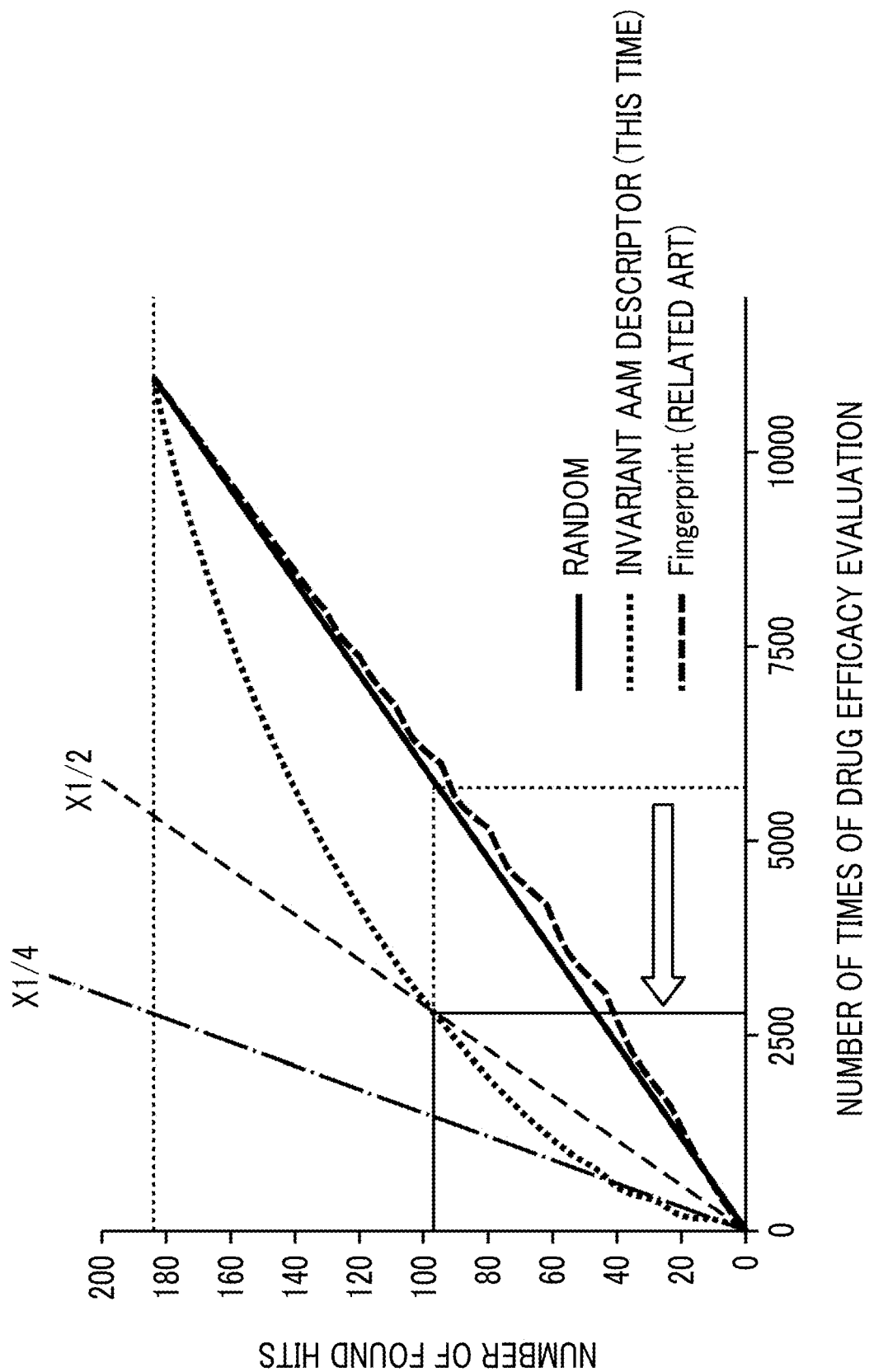
FIG. 14 is a graph showing the time of search for a hit in a case where an invariant AA descriptor is used.

FIG. 14 is a graph showing simulation results of importance Sampling for the above-described compound group. In a case where the invariant AAM descriptor according to the first embodiment is used, the hit search time (the number of times of drug efficacy evaluations for finding the number of same hit) compared with a case of the random team division is reduced to approximately one-half in a case of 50% search and reduced to one-fourth in a case of 25% search. Meanwhile, in a case of the team division using the fingerprint, the hit search time is not shortened. Further, the simulation of the Importance Sampling here indicates a method of providing variables showing the priority for each team and collecting more hits with a smaller number of times of measurements while updating the variables such that the priority of the team from which hits have found is raised and the priority of the team that does not have hits is lowered for each measurement. FIG. 14 shows an example in which an NB method (NB: Naive Bayes), which is a kind of machine learning method is used for controlling the priority, but the present invention is not limited thereto.

<Hit Search Time (Part 2)>

Figure 15:
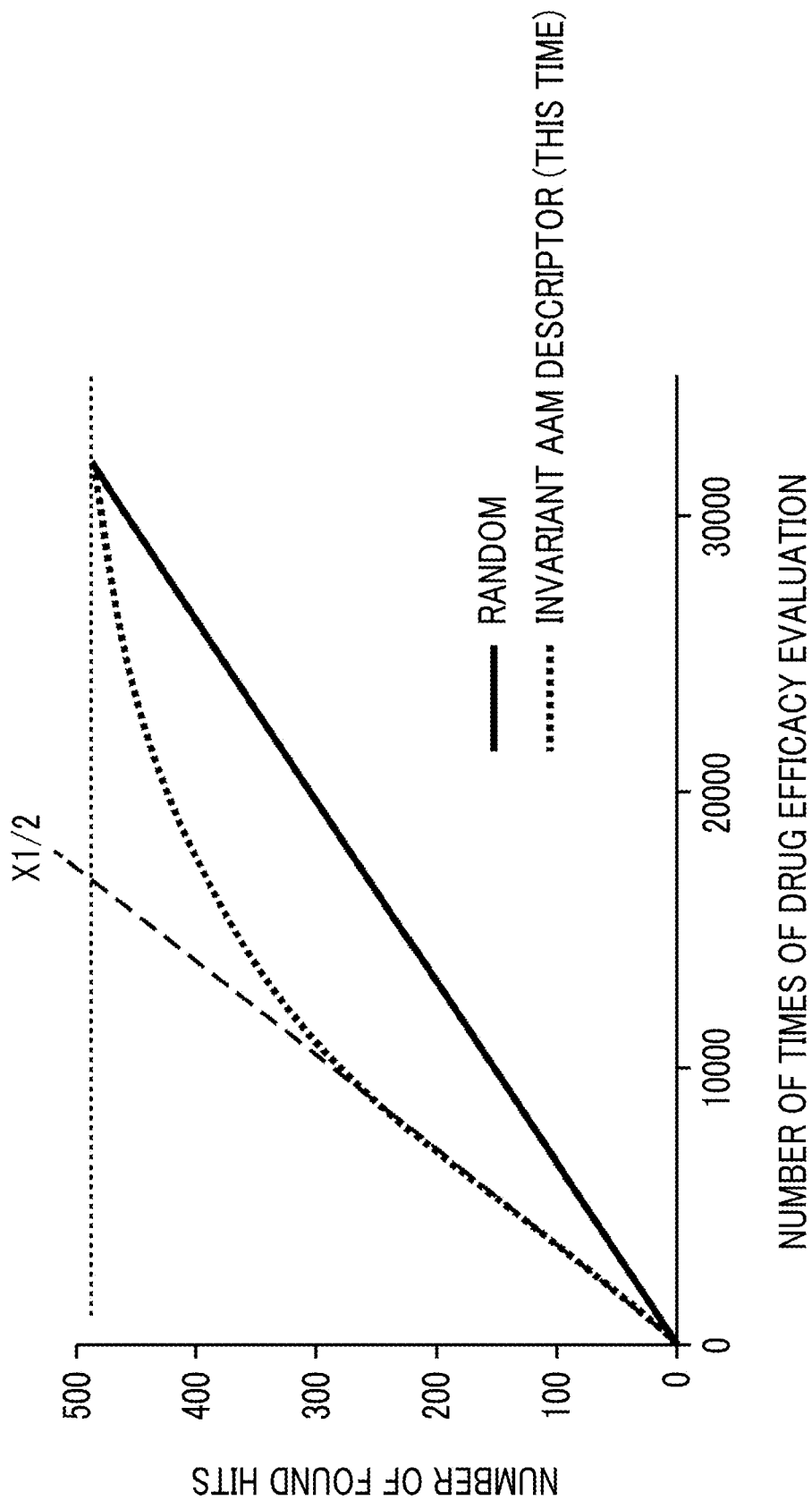
FIG. 15 is another graph showing the time of search a hit in a case where an invariant AAM descriptor is used.

FIG. 15 shows a simulation result of Importance Sampling for 32,464 compounds (having 483 hits) for a protein AA2AR, similar to the case of (part 1). The protein AA2AR is a membrane protein from which an X-ray crystal structure is difficult to obtain, but the hit search time is reduced to approximately one-half in a case of 50% search even with such a membrane protein.

According to the invariant AAM descriptor described above, since compounds having similar descriptors exhibit similar drug efficacies (binding to a target protein), the chemical properties of the target structure (a compound or a pocket structure) are accurately exhibited. According to the invariant AAM descriptor in which the three-dimensional AAM descriptor is converted into an invariant, the feature quantity is easily handled and the data capacity can be easily reduced while comparison (determination of the drug efficacy) of compounds based on the descriptor is accurately performed by performing conversion into an invariant using the three-dimensional AAM descriptor of two kinds of different amino acids. Further, according to the invariant AAM descriptor, hits are easily found, and the search can be sped up.

<Effects of Feature Quantity Calculating Method and Feature Quantity Calculating Program>

As described above, the screening device 10 according to the first embodiment is capable of calculating the feature quantity (the three-dimensional AAM descriptor or the invariant AAM descriptor) accurately showing the chemical property of the target structure using the feature quantity calculating method and the feature quantity calculating program according to the embodiment of the present invention.

<Extraction of Target Compound (Screening)>

Extraction of a target compound (pharmaceutical candidate compound) from a plurality of compounds using the above-described three-dimensional AAM descriptor and invariant AAM descriptor will be described. A target compound is extracted in a mode (first mode) in which the extraction is carried out based on the descriptor (the three-dimensional AAM descriptor or the invariant AAM descriptor) of the ligand or in a mode (second mode) in which the extraction is carried out based on the descriptor (the three-dimensional AAM descriptor or the invariant AAM descriptor) of the pocket structure of the target protein. The mode for extraction can be selected from the above-described modes according to the operation of the user via, the operation unit 400.

<Screening of Ligand Input>

Figure 16:
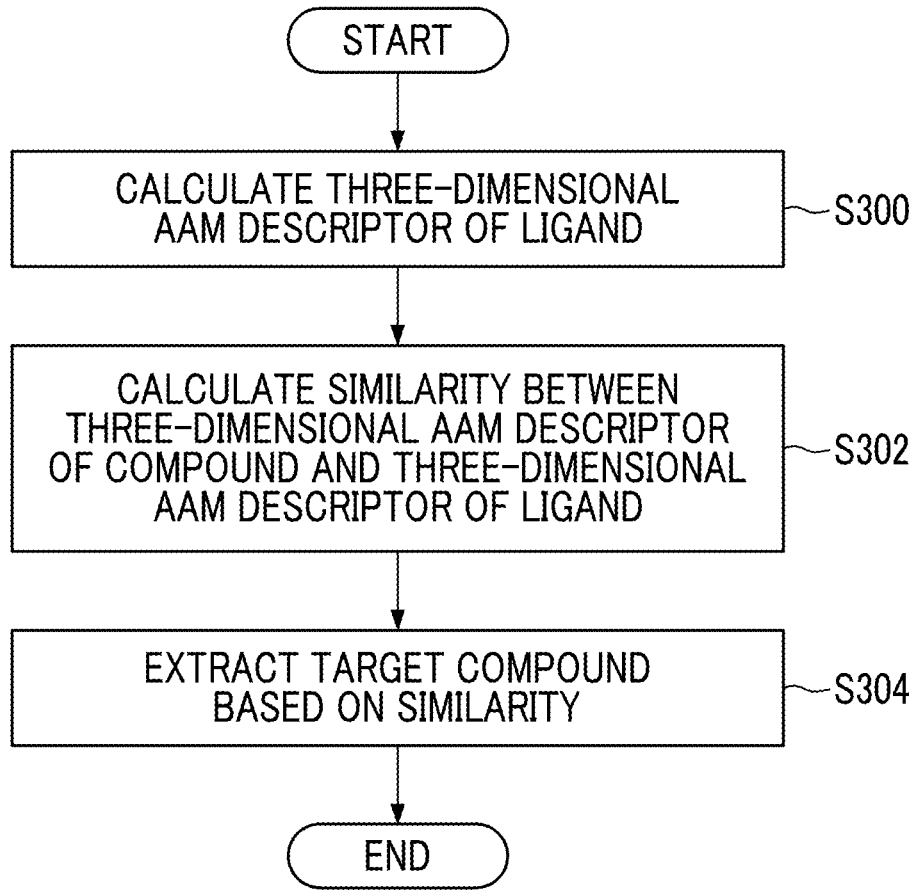
FIG. 16 is a flowchart showing a procedure for extracting a target compound based on the similarity between descriptors.

FIG. 16 is a flowchart showing a procedure for screening using a three-dimensional AAM descriptor of a ligand. After the start of the process, the feature quantity calculation unit 120 calculates a three-dimensional AAM descriptor of the ligand (Step S300: the feature quantity calculating step). Since the ligand is a compound whose binding to the target protein has been confirmed, the three-dimensional AAM descriptor in Step S300 can be calculated according to the procedure shown in the flowchart of FIG. 5.

As described above with reference to FIG. 4, in the screening device 10, the three-dimensional structure of the compound formed of a plurality of atoms and the three-dimensional AAM descriptor corresponding to the three-dimensional structure are stored in the storage unit 200 in association with each other for each of the plurality of compounds. The similarity calculation unit 130 calculates the similarity between the three-dimensional AAM descriptor of the compound and the three-dimensional AAM descriptor of the ligand calculated in Step S300 (Step S302: the similarity calculating step). After the calculation of the similarity, the compound extraction unit 140 extracts the target compound based on the similarity (Step S304: the target compound extracting step). As described above, in a case where three-dimensional AAM descriptors are similar, since similar drug efficacies (binding to the target protein) are exhibited, a compound having drug efficacy similar to that of the ligand (that is, a target compound serving as a pharmaceutical candidate) can be extracted by using the similarity of the three-dimensional AAM descriptor. Further, the extraction of the target compound based on the similarity (Step S304) can be specifically performed by "extracting a compound having a similarity greater than or equal to the threshold" or "extracting a compound in a descending order of the similarity".

FIG. 16 shows the procedure for screening using a three-dimensional AAM descriptor, but the screening using an invariant AAM descriptor can also be performed in the same procedure as described above. Specifically, the feature quantity calculation unit 120 calculates the invariant AAM descriptor (the invariant feature quantity) of the ligand according to the procedure of FIG. 5 and Equations (2) and (3), and the similarity calculation unit 130 calculates the similarity between the compound stored in the storage unit 200 and the invariant AAM descriptor. After the calculation of the similarity, the compound extraction unit 140 extracts the target compound based on the similarity. Specifically, the target compound can be extracted based on the similarity in the same manner as the extraction of the three-dimensional AAM descriptor.

FIGS. 17A and 17B are tables showing an example of a screening result of ligand input. FIG. 17A shows the result in a case of "extraction of a compound having a similarity greater than or equal to the threshold" using a three-dimensional AAM descriptor, and FIG. 17B shows the result in a case of "extraction of a compound in a descending order of the similarity" using an invariant AAM descriptor. Further, in FIG. 17A, the compound is extracted based on a three-dimensional AAM descriptor ($g_1(r)$) of the amino acid 1, but the compound may be extracted based on the three-dimensional AAM descriptor (for example, $g_2(r)$) of other amino acids (amino acids 2 to 20). In addition, the similarities (the similarity between the values of $g_1(r)$ and the similarity between the values of $g_2(r)$) of a plurality of three-dimensional AAM descriptors (for example, $g_1(r)$ and $g_2(r)$) of different amino acids are respectively calculated, and compounds may be extracted based on the results. The number of kinds of the three-dimensional AAM descriptors used for extraction of a compound may be one, but extraction of a compound based on the similarity can be accurately performed using a plurality of kinds of three-dimensional AAM descriptors. Further, in a case where a plurality of kinds of three-dimensional AAM descriptors are used, the combination of amino acids among the descriptors is not particularly limited (for example, a combination of $g_1(r)$ and $g_2(r)$ or a combination of $g_3(r)$ and $g_4(r)$ may be used).

Similarly, in FIG. 17B, a compound is extracted based on an invariant AAM descriptor ($F_{12}(s)$) of the amino acids 1 and 2, but the combination of amino acids used for calculation of the invariant AAM descriptor may vary (for example, $F_{34}(s)$ with amino acids 3 and 4). Further, a compound may be extracted based on a plurality of invariant AAM descriptors (for example, $F_{12}(s)$ and $F_{34}(s)$) with different combinations of amino acids (for example, the similarity between the values of $F_{12}(s)$ and the similarity between the values of $F_{34}(s)$ are used). The number of kinds of the invariant AAM descriptors used for extraction of a compound may be one, but extraction of a compound based on the similarity can be accurately performed using a plurality of kinds of invariant AAM descriptors. Further, in a case where a plurality of kinds of invariant AAM descriptors are used, the combination of amino acids among the descriptors is not particularly limited (for example, a combination of $F_{12}(s)$ and $F_{34}(s)$ or a combination of $F_{12}(s)$ and $F_{13}(s)$ may be used). The processing unit 100 (the feature quantity calculation unit 120, the similarity calculation unit 130, and the compound extraction unit 140) may determine which amino acid is to be used for calculation of the descriptor and the similarity according to the user's instruction via the operation unit 400, but the determination may be made by the processing unit 100 regardless of the user's instruction.

Further, the threshold of the similarity is set to 80% in FIG. 17A, and the number of times of extraction is set to 100 in FIG. 17B, but these values are merely examples. The threshold and the number of times of extraction can be set according to the conditions, for example, the accuracy of screening. The setting can be performed in response to a user input via the operation unit 400. Further, "a compound may be extracted in a descending order of the similarity" in a case where a three-dimensional AAM descriptor is used in contrast to FIGS. 17A and 17B, and "a compound having a similarity greater than or equal to the threshold may be extracted" in a case where an invariant AAM descriptor is used. The compound extraction unit 140 stores the extraction result as shown in FIGS. 17A and 17B in the storage unit 200 as the compound extraction result 260 (see FIG. 3).

<Screening of Target Protein Input>

Figure 18:
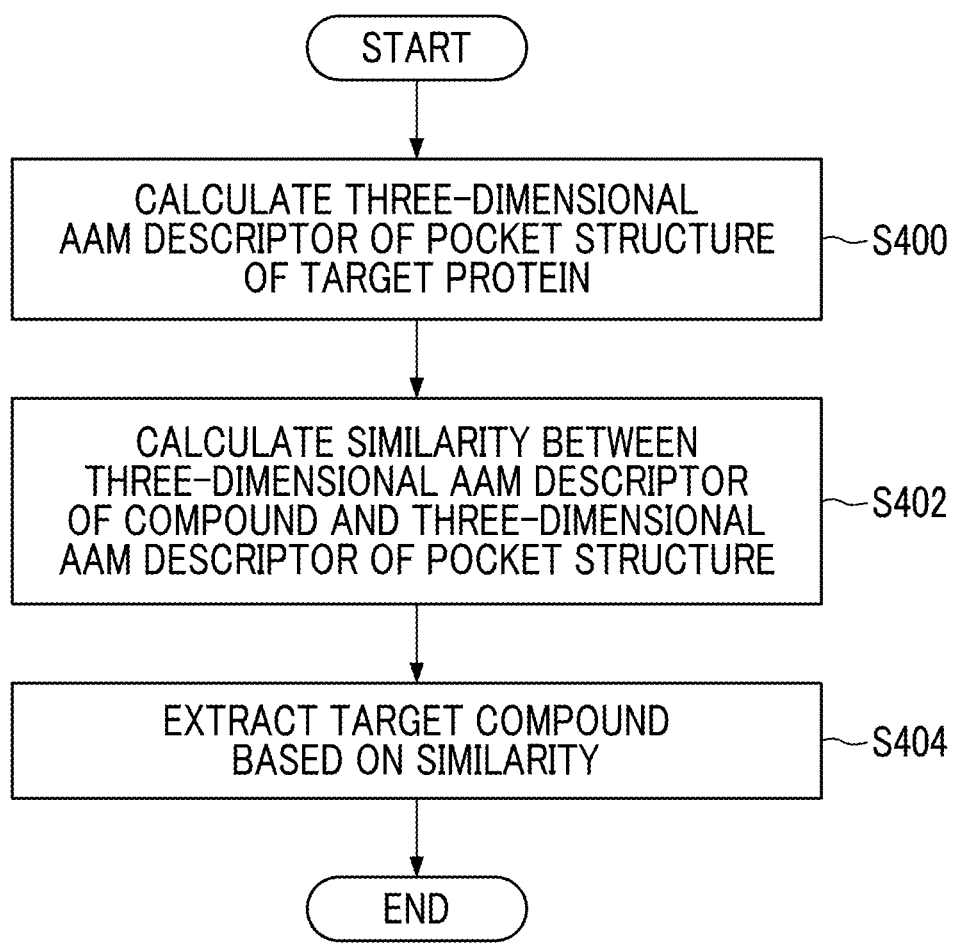
FIG. 18 is another flowchart showing a procedure for extracting a target compound based on the similarity between descriptors.

FIG. 18 is a flowchart showing a procedure for screening of a pocket structure of a target protein using a three-dimensional AAM descriptor. After the start of the process, the feature quantity calculation unit 120 calculates a three-dimensional AAM descriptor of the pocket structure of the target protein (Step S400: the feature quantity calculating step). The three-dimensional AAM descriptor in Step S400 can be calculated according to the procedure shown in the flowchart of FIG. 9. The similarity calculation unit 130 calculates the similarity between the three-dimensional AAM descriptor of the compound and the three-dimensional AAM descriptor of the pocket structure calculated in Step S400 (Step S402: the similarity calculating step). After the calculation of the similarity, the compound extraction unit 140 extracts the target compound based on the similarity (Step S404: the target compound extracting step). Similar to the case of the ligand input described above, the extraction of the target compound based on the similarity (Step S404) can be specifically performed by "extracting a compound having a similarity greater than or equal to the threshold" or "extracting a compound in a descending order of the similarity".

Even in a case of using the invariant AAM descriptor, a target compound can be extracted according to the same procedure as in the flowchart of FIG. 18.

FIGS. 19A and 19B are tables showing an example of a screening result of target protein input. FIG. 19A shows the result in a case of "extraction of a compound having a similarity greater than or equal to the threshold" using a three-dimensional AAM descriptor, and FIG. 19B shows the result in a case of "extraction of a compound in a descending order of the similarity" using an invariant AAM descriptor. The threshold of the similarity and the number of times of extraction can be set according to the conditions, for example, the accuracy of screening. The setting can be performed in response to a user input via the operation unit 400. Further, "a compound may be extracted in a descending order of the similarity" in a case where a three-dimensional AAM descriptor is used in contrast to FIGS. 19A and 19B, and "a compound having a similarity greater than or equal to the threshold may be extracted" in a case where an invariant AAM descriptor is used.

In a case of screening for the target protein input, the kind of amino acid may be changed in the same manner as in the case of screening for the ligand input (see FIGS. 17A and 17B and the description of these tables), or a plurality of descriptors of different amino acids (the three-dimensional AAM descriptor and the invariant AAM descriptor) may be used. The number of kinds of the descriptors used for extraction of a compound may be one, but extraction of a compound based on the similarity can be accurately performed using a plurality of kinds of descriptors. Further, in a case where a plurality of kinds of descriptors are used, the combination of amino acids among the descriptors is not particularly limited. The processing unit 100 (the feature quantity calculation unit 120, the similarity calculation unit 130, and the compound extraction unit 140) may determine which amino acid is to be used for calculation of the descriptor and the similarity according to the user's instruction via the operation unit 400, but the determination may be made by the processing unit 100 regardless of the user's instruction.

The compound extraction unit 140 stores the extraction result as shown in FIGS. 19A and 19B in the storage unit 200 as the compound extraction result 260 (see FIG. 3).

<Effect of Screening Device>

As described above, the screening device 10 according to the first embodiment is capable of efficient screening of a pharmaceutical candidate compound according to the screening method and the screening program according to the embodiment of the present invention using the feature quantity (the three-dimensional AAM descriptor or the invariant AAM descriptor) calculated by the feature quantity calculating method and the feature quantity calculating program according to the embodiment of the present invention.

Second Embodiment

Figure 20:
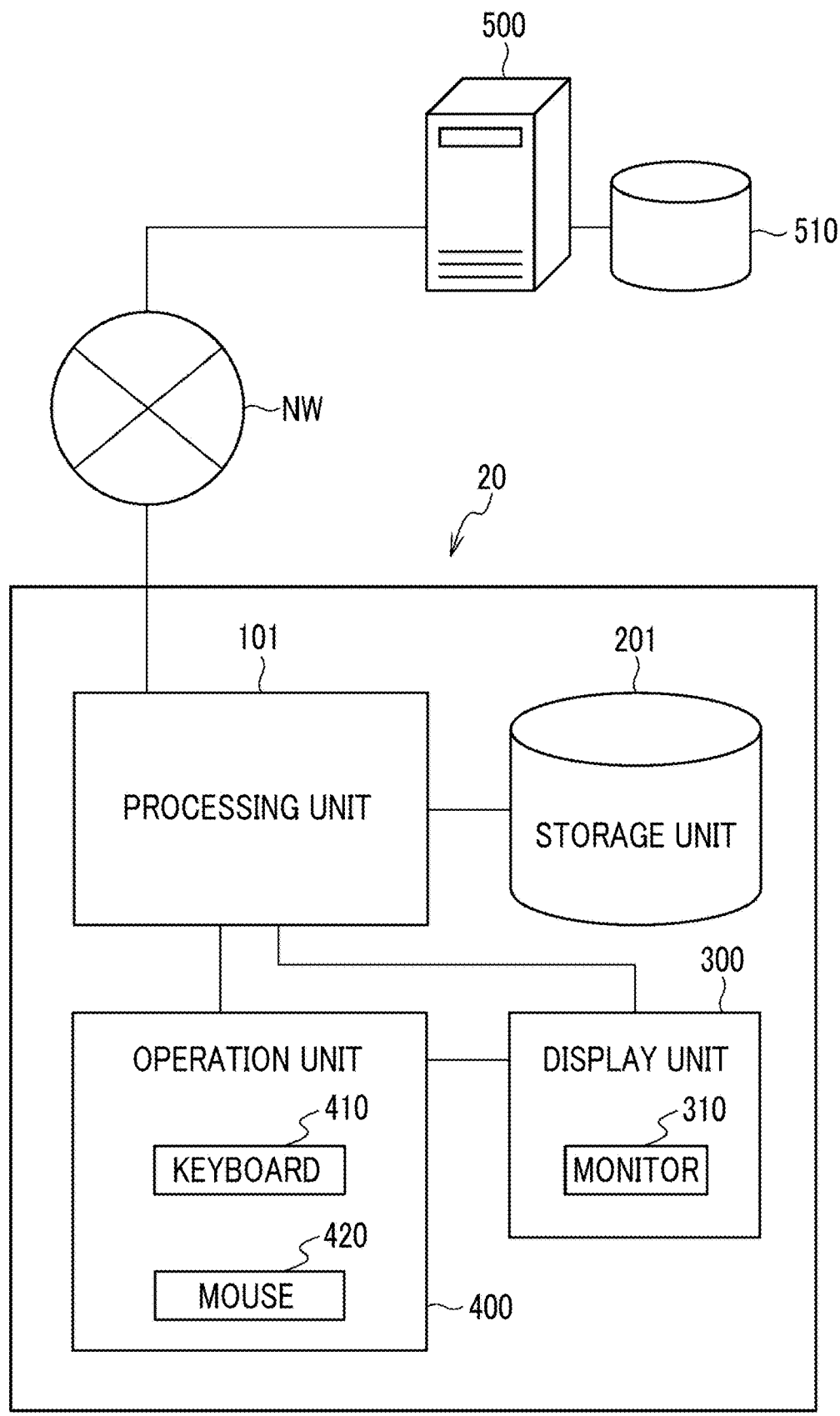
FIG. 20 is a block diagram showing a configuration of a compound creating device according to a second embodiment.

A compound creating device according to a second embodiment of the present invention will be described. FIG. 20 is a block diagram showing a configuration of a compound creating device 20 (a feature quantity calculating device or a compound creating device). Further, the same elements as those in the first embodiment are denoted by the same reference numerals, and detailed description thereof will not he provided.

Figure 21:
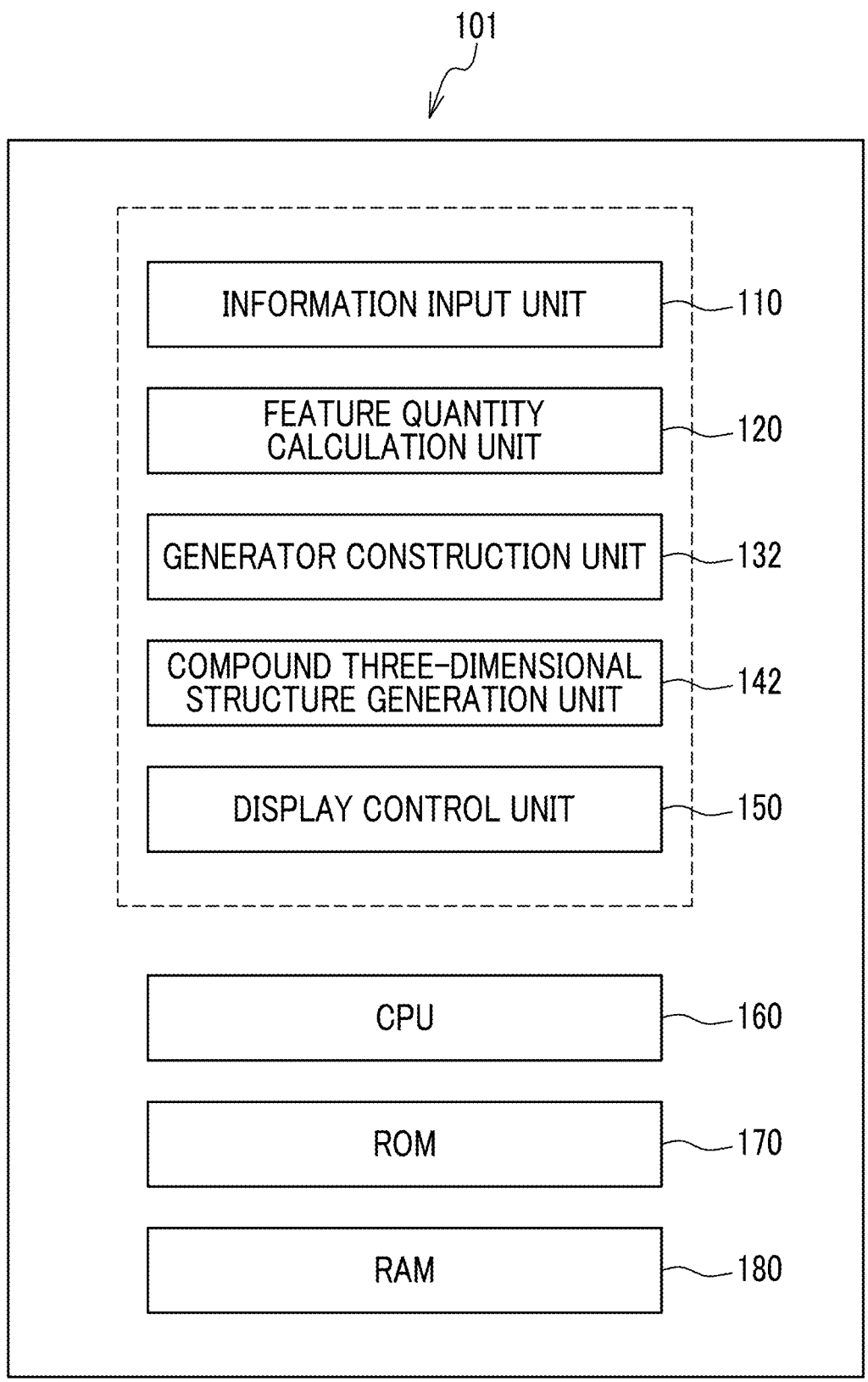
FIG. 21 is a diagram showing a configuration of a processing unit.

The compound creating device 20 includes a processing unit 101. The processing unit 101 is formed as shown in FIG. 21 and includes an information input unit 110, a feature quantity calculation unit 120 (feature quantity calculation unit), a generator construction unit 132 (generator construction unit), a compound three-dimensional structure generation unit 142 (compound three-dimensional structure generation unit), and a display control unit 150. The functions of the information input unit 110, the feature quantity calculation unit 120, and the display control unit 150 are respectively the same as the information input unit 110, the feature quantity calculation unit 120, and the display control unit 150 in the above-described screening device 10. The functions of these units can be realized using various processors in the same manner as described above in the section of the screening device 10.

Figure 22:
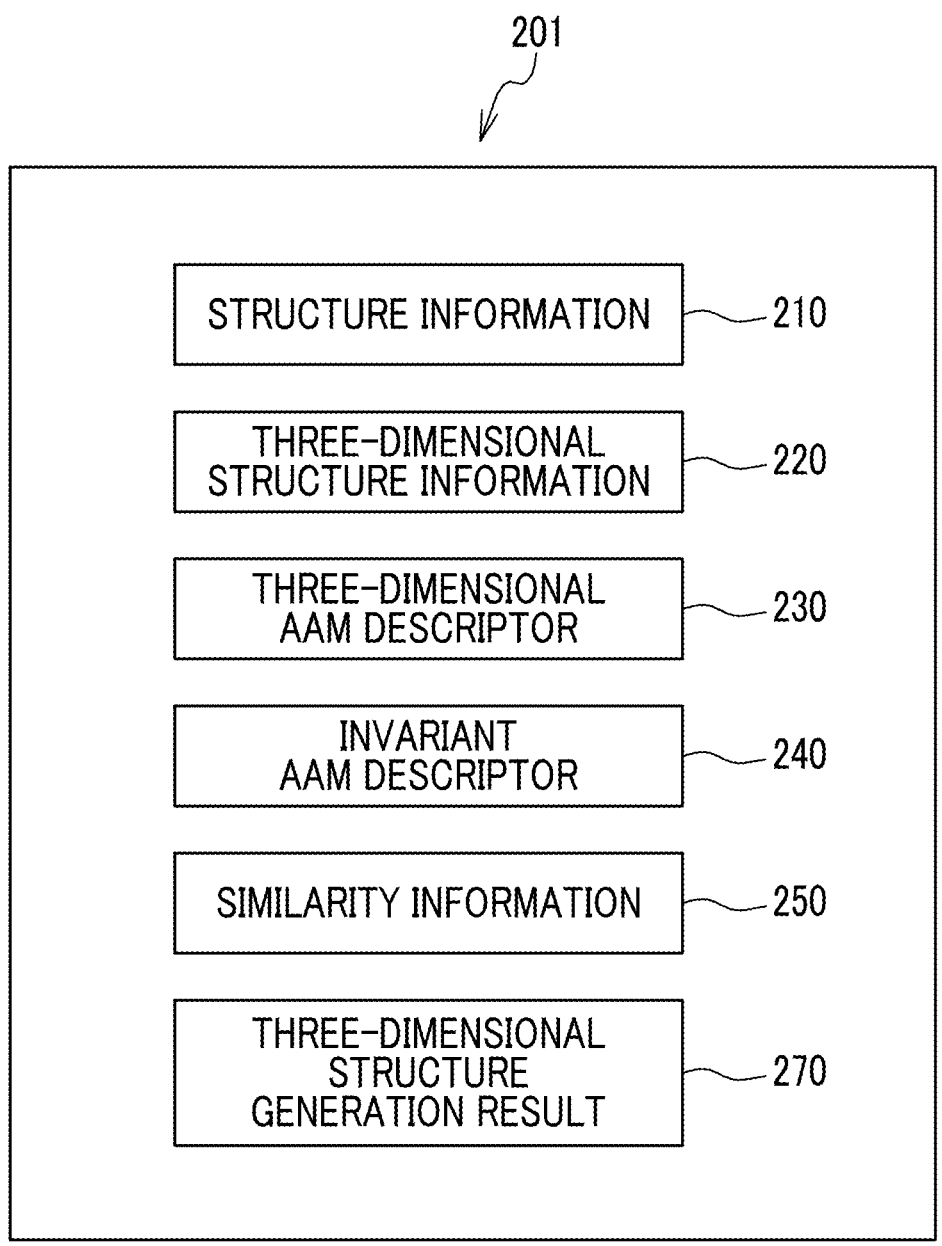
FIG. 22 is a diagram showing information stored in a storage unit.

FIG. 22 is a diagram showing information stored in the storage unit 201. The storage unit 201 stores a three-dimensional structure generation result 270 instead of the compound extraction result 260 in the screening device 10. The information stored in the storage unit 201 is stored in association as described above with reference to FIG. 4.

<Generation of Three-Dimensional Structure of Target Compound>

Generation of a three-dimensional structure of a target compound (pharmaceutical candidate compound) using the above-described three-dimensional AAM descriptor and invariant AAM descriptor will be described. Since search is not performed in the generation of a three-dimensional structure of a target compound using the compound creating device 20, the three-dimensional structure of the compound can be generated even in a case of "no solution was found as the result of screening search", and thus the three-dimensional structure of the pharmaceutical candidate compound can be efficiently created. A three-dimensional structure is generated in a mode in which the generation is carried out based on the descriptor (the three-dimensional AAM descriptor or the invariant AAM descriptor) of the ligand or in a mode in which the generation is carried out based on the descriptor (the three-dimensional AAM descriptor or the invariant AAM descriptor) of the pocket structure of the target protein. The mode for generation of a three-dimensional structure can be selected from the above-described modes according to the operation of the user via the operation unit 400.

<Generation of Three-Dimensional Structure in Case of Ligand Input>

Figure 23:
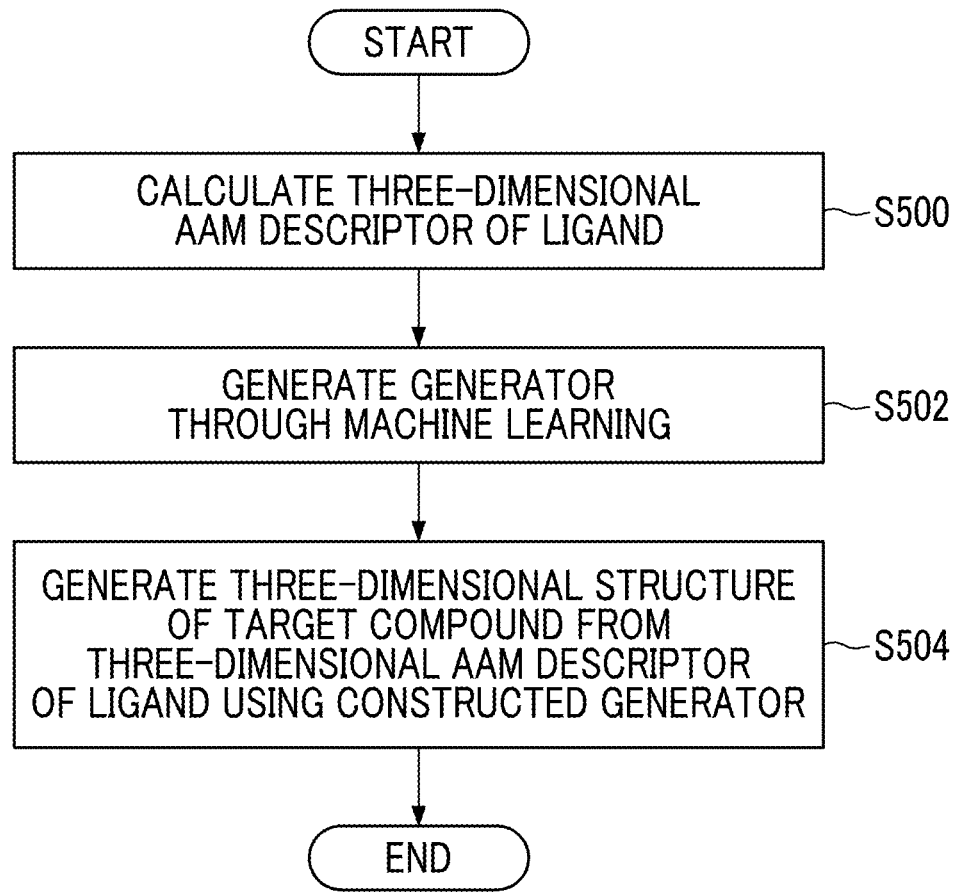
FIG. 23 is a flowchart showing a procedure for generating a three-dimensional structure in the case where a ligand is input.

FIG. 23 is a flowchart showing a procedure for generating a three-dimensional structure in a case of ligand input. After the start of the process, the feature quantity calculation unit 120 calculates a descriptor (a three-dimensional AAM descriptor) of the ligand (Step S500: the target structure designating step, the three-dimensional structure generating step, and the feature quantity calculating step). The process of Step S500 can be performed using the feature quantity calculating method and the feature quantity calculating program according to the embodiment of the present invention in the same manner as in the first embodiment (see FIGS. 5 to 8 and the description of these drawings).

In Step S502, the generator construction unit 132 constructs a generator through machine learning (a generator constructing step). Hereinafter, the process of Step S502 will be described with reference to FIG. 24. (Step 1) The feature quantity calculation unit 120 calculates three-dimensional AAM descriptors of a plurality of compounds and creates a pair (three-dimensional data) of a structural formula (a three-dimensionalized structural formula) and a three-dimensional AAM descriptor. (Step 2) The generator construction unit 132 constructs a generator through machine learning (deep learning) using a three-dimensional structure of a compound as teacher data and a three-dimensional AAM descriptor as an explanatory variable. The method of deep learning is not limited to a specific method, and a simple fully-coupled neural network or a convolutional neural network (CNN) may be employed. However, since the generation accuracy of the three-dimensional structure depends on the learning method to be used, it is preferable to select a learning method according to the condition for generating the three-dimensional structure and the condition such as the required accuracy. As a generator construction method, the methods described in additional notes 14 and 15 described below may be used.

After the completion of the processes of Steps 1 and 2 described above, the process returns to the flowchart of FIG. 23. The compound three-dimensional structure generation unit 142 generates a three-dimensional structure (three-dimensionalized structural formula) of the target compound (hit) from the three-dimensional AAM descriptor of the ligand using the constructed generator (Step S504: the compound three-dimensional structure generating step). In this manner, the three-dimensional structure of a compound having drug efficacy (binding to a target protein) similar to that of a ligand, that is, a pharmaceutical candidate compound can be obtained. Further, a plurality of three-dimensional structures that provide the same three-dimensional AAM descriptor may be present. The compound three-dimensional structure generation unit 142 stores the generated three-dimensional structure in the storage unit 201 in association with the three-dimensional AAM descriptor (the three-dimensional AAM descriptor 230) as the three-dimensional structure generation result 270 (see FIG. 22). The display control unit 150 may display the generated three-dimensional structure on the monitor 310 in response to the user's instruction via the operation unit 400.

Further, in the procedure described above, the number of kinds of amino acids used for calculation of the three-dimensional AAM descriptor for machine learning may be one or plural. However, the accuracy of the generated three-dimensional structure can be improved by calculating the three-dimensional AAM descriptor of a plurality of kinds of amino acids and providing the result for learning. Further, in a case where a plurality of three-dimensional AAM descriptors having different kinds of amino acids are used, the combination of amino acids among the descriptors is not particularly limited. The processing unit 100 (the feature quantity calculation unit 120, the similarity calculation unit 130, and the compound extraction unit 140) may determine which amino acid is to be used for calculation of the three-dimensional AAM descriptor and for provision for learning according to the user's instruction via the operation unit 400, but the determination may be made by the processing unit 100 regardless of the user's instruction.

<Example of Generation of Three-Dimensional Structure>

An example of a three-dimensional structure generated using a generator constructed through machine learning will be described. In this example, 1,800 compounds among the library compounds are learned according to the above-described method using a simple fully-coupled neural network, and the extent to which the three-dimensional structures of the remaining 200 compounds can be reproduced is examined. The results are shown in FIG. 25. in a case where the number of interlayers in the neural network is increased, the average cos similarity reaches 59%. FIGS. 26A and 26B are diagrams showing a three-dimensional structure (structural formula) and a correct structural formula (FIGS. 26A and 26B, respectively) generated from a three-dimensional AAM descriptor as an example showing such similarity.

<Relationship Between Features of Teacher Data and Generated Three-Dimensional Structure>

The three-dimensional structure generated according to the above-described procedure is affected by the features of the compound provided as teacher data. Therefore, by selecting the features of the compound to be provided as teacher data, a compound having a three-dimensional structure with different features can be generated. For example, a compound having drug efficacy similar to that of a ligand and having a three-dimensional structure that is easy to synthesize can be generated by providing, as teacher data, a three-dimensional AAM descriptor of a compound having a three-dimensional structure that is easy to synthesize. It is possible to select which compound to be provided for the three-dimensional AAM descriptor as the teacher data according to the features of the compound intended to be generated.

<Generation of Three-Dimensional Structure Using Invariant AAM Descriptor>

In FIGS. 23 to 26, the generation of the three-dimensional structure using the three-dimensional AAM descriptor has been described. Meanwhile, similarly to the case of using the three-dimensional AAM descriptor, the three-dimensional structure of the target compound can be generated through machine learning (deep learning) using the invariant AAM descriptor as teacher data and the three-dimensional structure (three-dimensionalized structural formula) as an explanatory variable even in a case of using the invariant AAM descriptor (invariant feature quantity).

<Generation of Three-Dimensional Structure in Case of Target Protein Input>

The compound creating device 20 is capable of generating a three-dimensional structure of a target compound by setting a target protein as an input, in addition to the generation of the three-dimensional structure by ligand input. Even in this case, similarly to the case of ligand input, generation of a three-dimensional structure can be performed using a three-dimensional AAM descriptor and generation of a three-dimensional structure can be performed using an invariant AAM descriptor.

Figure 27:
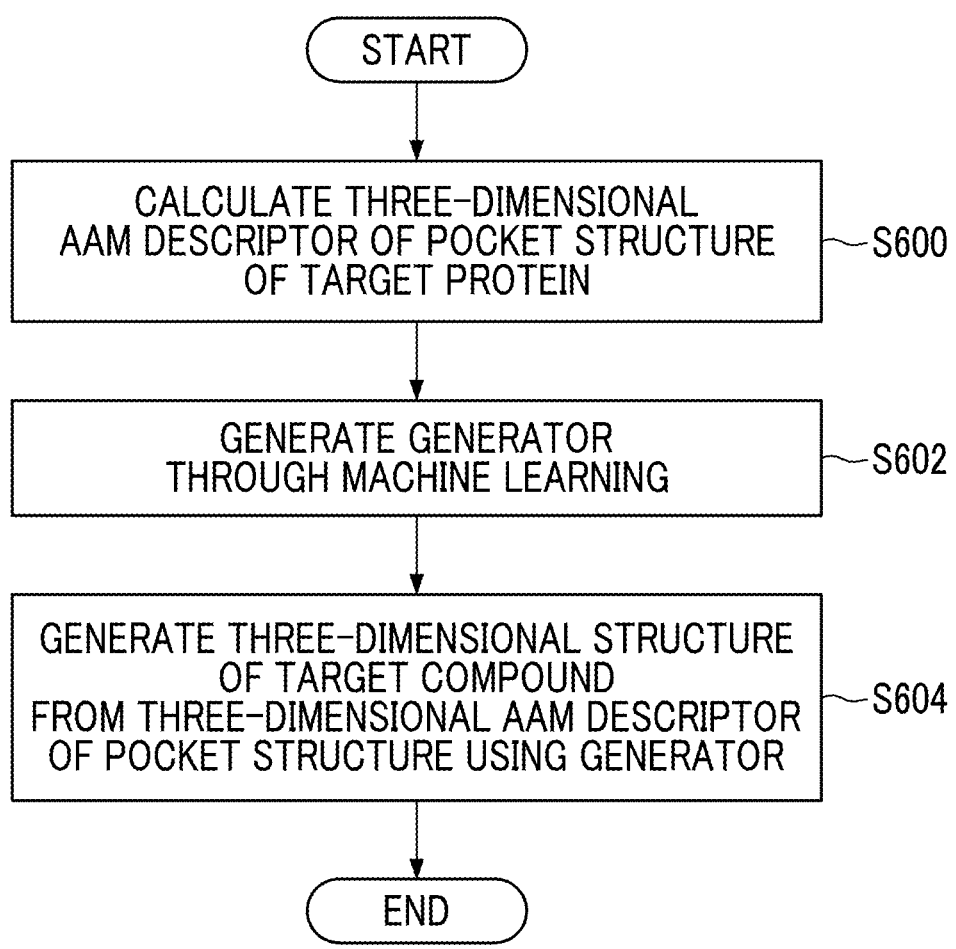
FIG. 27 is a flowchart showing a procedure for generating a three-dimensional structure in a case where a target protein is input.

FIG. 27 is a flowchart showing a procedure for generating a three-dimensional structure in a case of setting a target protein as an input (a three-dimensional AAM descriptor is set to be used). In a case where the process is started, the feature quantity calculation unit 120 calculates the three-dimensional AAM descriptor of the pocket structure of the target protein (Step S600: the target structure designating step, the three-dimensional structure generating step, and the feature quantity calculating step). The process of Step S600 can be performed using the feature quantity calculating method according to the embodiment of the present invention, similarly to the first embodiment (see FIGS. 9 and 10 and the description of these drawings).

In Step S602, the generator construction unit 132 constructs a generator through machine learning (deep learning) similar to the case of ligand input (the generator constructing step). The construction of the generator can be performed in the same manner as in Steps 1 and 2 described above. The compound three-dimensional structure generation unit 142 generates a three-dimensional structure (three-dimensionalized structural formula) of the target compound (hit) from the three-dimensional AAM descriptor of the pocket structure using the constructed generator (Step S604: the compound three-dimensional structure generating step). In this manner, the three-dimensional structure of a compound having drug efficacy (binding to a target protein) similar to that of the pocket structure, that is, a pharmaceutical candidate compound can be obtained. Further, a plurality of three-dimensional structures that provide the same three-dimensional AAM descriptor may be present. The compound three-dimensional structure generation unit 142 stores the generated three-dimensional structure in the storage unit 201 in association with the three-dimensional AAM descriptor (the three-dimensional AAM descriptor 230) as the three-dimensional structure generation result 270 (see FIG. 22). The display control unit 150 may display the generated three-dimensional structure on the monitor 310 in response to the user's instruction via the operation unit 400.

<Effects of Compound Creating Device>

As described above, the compound creating device 20 according to the second embodiment efficiently creates a three-dimensional structure of a pharmaceutical candidate compound according to the feature quantity calculating method and the compound creating program according to the embodiment of the present invention using the feature quantity (the three-dimensional AAM descriptor or the invariant AAM descriptor) calculated using the compound creating method and the feature quantity calculating program according to the embodiment of the present invention.

Third Embodiment

The first embodiment described above is an embodiment in which the calculation of the feature quantity and screening based on the calculation are performed, and the second embodiment is an embodiment in which the calculation of the feature quantity and creation of the three-dimensional structure of the target compound based on the calculation are performed. In addition to the calculation of the feature quantity, both the screening and the creation of a three-dimensional structure of the target compound may be performed. Therefore, a pharmaceutical candidate compound search device 30 (the feature quantity calculating device, the screening device, and the compound creating device; see FIG. 28) according to the third embodiment includes a processing unit 102 shown in FIG. 28 in place of the processing unit 100 of the screening device 10 shown in FIG. 1 or the processing unit 101 of the compound creating device 20 shown in FIG. 20. As shown in FIG. 29, the processing unit 102 includes a feature quantity calculation unit 120 (the feature quantity calculation unit and the invariant conversion unit), a similarity calculation unit 130 (the similarity calculation unit), a generator construction unit 132 (the generator construction unit), a compound extraction unit 140 (the compound extraction unit), and a compound three-dimensional structure generation unit 142 (the compound three-dimensional structure generation unit) and can perform calculation of a feature quantity, screening, and creation of a three-dimensional structure of a compound. In addition, the pharmaceutical candidate compound search device 30 stores information related to the above-described performance in the storage unit 202. Specifically, as shown in FIG. 30, information (see FIGS. 3 and 22) stored in the storage unit 200 and the storage unit 201 is stored in the storage unit 202 together.

Since other elements are the same as those of screening device 10 shown in FIG. 1 and the compound creating device 20 shown in FIG. 20, the elements are denoted by the same reference numerals and the detailed description thereof will not be provided.

With the above-described configuration, also in the pharmaceutical candidate compound search device 30 according to the third embodiment, the feature quantity accurately showing the chemical properties of the target structure is calculated, screening of a pharmaceutical candidate compound is efficiently performed, and a three-dimensional structure of the pharmaceutical candidate compound can be efficiently created, similarly to the screening device 10 and the compound creating device 20.

The embodiments of the present invention have been described above, but the present invention is not limited to the above-described embodiments, and various modifications can be made without departing from the spirit of the present invention as exemplified below.

<Target of Drug That Can be Treated>

In the present invention, deoxyribonucleic acid (DNA), ribonucleic acid (RNA), cell membranes, and polysaccharides can be treated in addition to proteins as the targets of drugs. However, in the first to third embodiments, it is necessary to change the amino acid to another one. Specifically, an amino acid is changed to a nucleic acid base in a case of DNA, an amino acid is changed to a nucleic acid base in a case of RNA, an amino acid is changed to a lipid molecule in a case of cell membranes, and an amino acid is changed to a monosaccharide molecule in a case of polysaccharides. In the description below, the reason why DNA, RNA, cell membranes, and polysaccharides can be treated with this change in the present invention will be described. Proteins, DNA, RNA, cell membranes, and polysaccharides are collectively referred to as biopolymers and are made up of unique building blocks. Specifically, the building block of proteins is an amino acid, the building block of DNA is a nucleic acid base, the building block of RNA is similarly a nucleic acid base, the building block of cell membranes is a lipid molecule, and the building block of polysaccharides is a monosaccharide molecule. Since DNA, RNA, cell membranes, and polysaccharides, which are biopolymers other than proteins also have pockets that are active sites similarly to the proteins, even in a case where a drug target (target biopolymer) is DNA, RNA, cell membranes and polysaccharides, the present invention can deal with this by changing amino acids to the building blocks of the targets in the first to third embodiments shown in the case of proteins. Further, water can be considered in a case of quantifying the degree of accumulation of amino acids, nucleic acid bases, lipid molecules, and monosaccharide molecules in the periphery of a compound or a pocket structure.

<Activities That Can be Treated>

In the present invention, in addition to the typical activity which is the "activity of a target biomolecule alone by a compound", the "activity of a cell, which is a composite formed of other biomolecules in addition to the target biomolecule by a compound" can also be treated.

(MODIFICATION EXAMPLE 1) FEATURE QUANTITY OF BIOPOLYMER OTHER THAN AMINO ACID AND USE THEREOF

<Target and Probe>

In a case of treating DNA, RNA, cell membranes, and polysaccharides, which are biopolymers (compounds) other than proteins as drug targets (target biopolymers), the probe used for calculation of the feature quantity is not an amino acid but a different substance (the building block of each target). Specifically, in a case where the targets are "DNA, RNA, cell membranes, and polysaccharides", the probes are respectively set as "one or more kinds of nucleic acid bases, one or more kinds of nucleic acid bases, one or more kinds of lipid molecules, and one or more kinds of monosaccharide molecules". Further, water and one or more kinds of ions may be considered during the quantification of the degree of accumulation using these as probes. Further, in a case where the targets are formed of a plurality of kinds of biopolymers among "DNA, RNA, cell membranes, and polysaccharides", the probe can also be set as one or more of "one or more kinds of nucleic acid bases, one or more kinds of lipid molecules, one or more kinds of monosaccharide molecules, water, and one or more kinds of ions" (the kind, the number, and the combination thereof may be optional according to the configurations of the targets) in accordance of the configurations of the targets. The ions constituting the probes may be monatomic ions or polyatomic ions. Further, all the probes are assumed to generate van der Waals forces.

<Calculation of Feature Quantity and Screening>

The configurations of devices for calculating the feature quantity (the feature quantity according to Modification Example 1) and performing screening (the feature quantity calculating device and the screening device) are the same as those in the first embodiment (see FIGS. 1 to 3). However, the descriptor according to Modification Example 1 is calculated and stored instead of the three-dimensional AAM descriptor 230 in FIG. 3, and the invariant feature quantity according to Modification Example 1 is calculated and stored instead of the invariant AAM descriptor 240. The procedures for calculation of the feature quantity and screening are the same as those in the first embodiment, and the feature quantity calculating method, the feature quantity calculating program, the screening method, and the screening program according to the embodiment of the present invention can be used. Specifically, the invariant feature quantity according to Modification Example 1 is calculated (see Equation (2)) by calculating the distribution function (see Equation (1)) using "one or more (the kind, the number, and the combination thereof may be optional) selected from one or more kinds of nucleic acid bases, one or more kinds of lipid molecules, one or more kinds of monosaccharide molecules, water, and one or more kinds of ions" instead of the "amino acid" as the probe in the calculation of the feature quantity (see FIG. 5) according to the first embodiment, calculating the feature quantity according to Modification Example 1 from the distribution function, and performing Fourier transform on the feature quantity according to Modification Example 1. Further, the invariant feature quantity according to Modification Example 1 may be calculated by angular integration of the correlation function (see Equations (3) and (4)) using the feature quantity of two different kinds of probes according to Modification Example 1 (the first probe formed of one or more selected from one or more kinds of nucleic acid bases, one or more kinds of lipid molecules, one or more kinds of monosaccharide molecules, water, and one or more kinds of ions and the second probe that is formed of one or more selected from one or more kinds of nucleic acid bases, one or more kinds of lipid molecules, one or more kinds of monosaccharide molecules, water, and one or more kinds of ions and different from the first probe).

In addition, the target compound can be extracted based on the similarity between the feature quantity of according to Modification Example 1 a plurality of compounds and the feature quantity according to Modification Example 1 of the binding compound using the feature quantity according to Modification Example 1 instead of the three-dimensional AAM descriptor in the first embodiment. A compound having a similarity greater than or equal to the threshold may be extracted, or a compound may be extracted in a descending order of the similarity.

<Calculation of Feature Quantity and Creation of Compound>

The configurations of devices for calculating a feature quantity (the feature quantity according to Modification Example 1) and creating a compound (the feature quantity calculating device and the compound creating device) are the same as those in the second embodiment (see FIGS. 20 to 22). However, the descriptor according to Modification Example 1 (the feature quantity according to Modification Example 1) is calculated and stored instead of the three-dimensional AAM descriptor 230 in FIG. 22, and the invariant feature quantity according to Modification Example 1 is calculated and stored instead of the invariant AAM descriptor 240. The procedures for calculation of the feature quantity and creation of a compound are the same as those in the second embodiment, and the feature quantity calculating method, the feature quantity calculating program, the compound creating method, and the compound creating program according to the embodiment of the present invention can be used. In Modification Example 1, a generator is constructed through machine learning (deep learning) using the three-dimensional structure of the compound as teacher data and the feature quantity according to Modification Example 1 as an explanatory variable, and the three-dimensional structure of the target biopolymer can be generated from the feature quantity according to Modification Example 1 of the binding compound that is a compound whose binding to the target biopolymer has been confirmed using the constructed generator. Further, similar to the first to third embodiments, a compound having a three-dimensional structure with different features can be generated by selecting features of a compound to be provided as teacher data.

In the same manner as in the first to third embodiments described above, since the drug efficacy of a compound (the binding force with respect to the target such as DNA) is locally exhibited as the result of an interaction between a compound and a nucleic acid base (probe), in a case where the degree of accumulation of nucleic acid bases and the like is similar between compounds, the compounds have similar binding forces with respect to the targets That is, the compounds with similar feature quantities according to Modification Example 1 exhibit similar drug efficacies. Therefore, in Modification Example 1, the chemical properties of the compound can be accurately exhibited by the feature quantity according to Modification Example 1. In addition, in a case where the feature quantities according to Modification Example 1 are similar between the target compound and the binding compound that is bound to the target biopolymer, the drug efficacies of both the binding compound and the target compound are similar. Therefore, according to Modification Example 1, a target compound having drug efficacy similar to that of the binding compound is extracted based on the feature quantity according to Modification Example 1 so that screening of a pharmaceutical candidate compound can be efficiently performed. Further, according to Modification Example 1, similarly to the above-described embodiments, a structural formula of a compound having a feature quantity similar to the feature quantity (the feature quantity according to Modification Example 1) of the binding compound (accordingly, the drug efficacies are similar) is generated without performing search, and thus the three-dimensional structure of the pharmaceutical candidate compound can be efficiently created.

Figure 28:
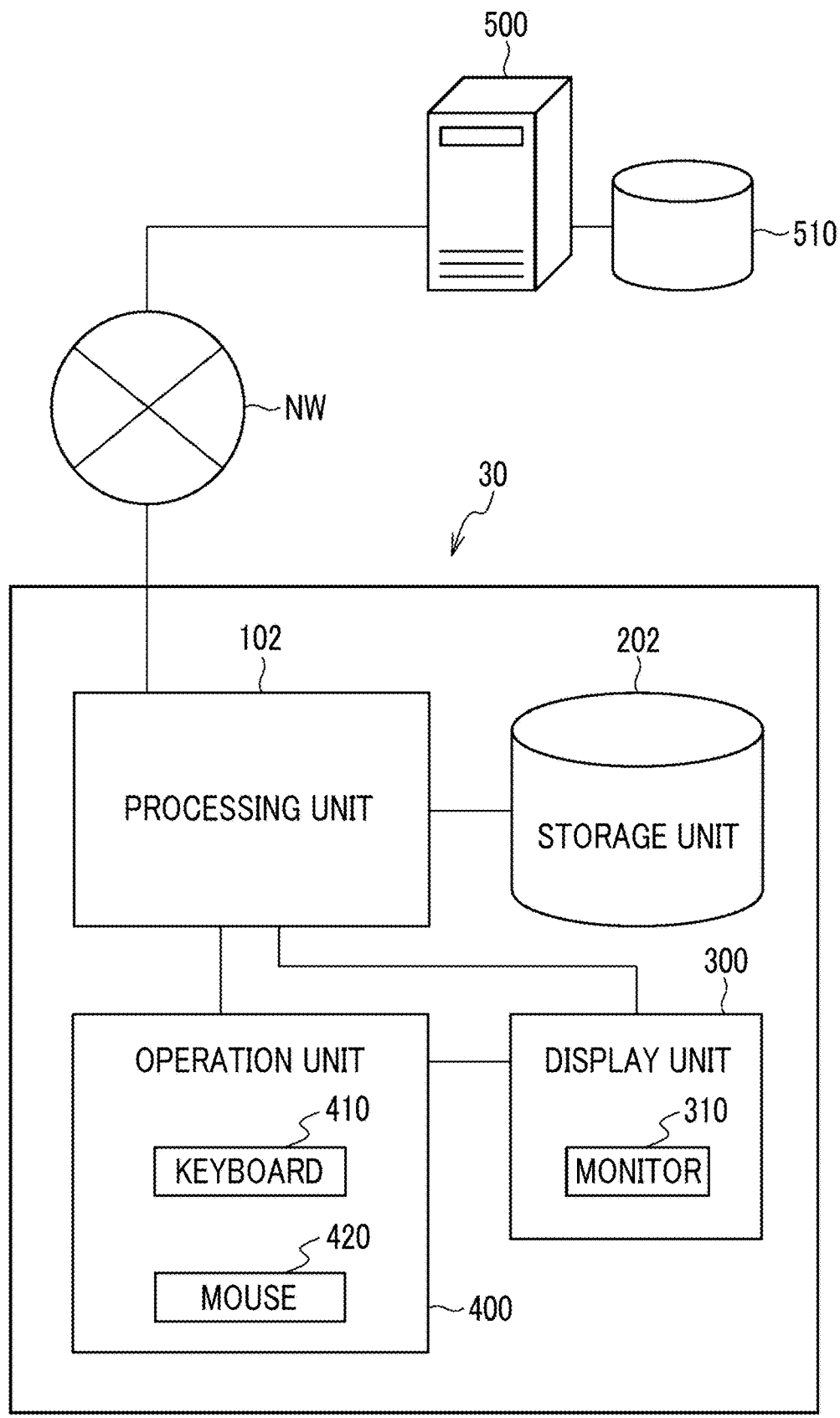
FIG. 28 is a block diagram showing a configuration of a pharmaceutical candidate compound search device according to a third embodiment.
Figure 29:
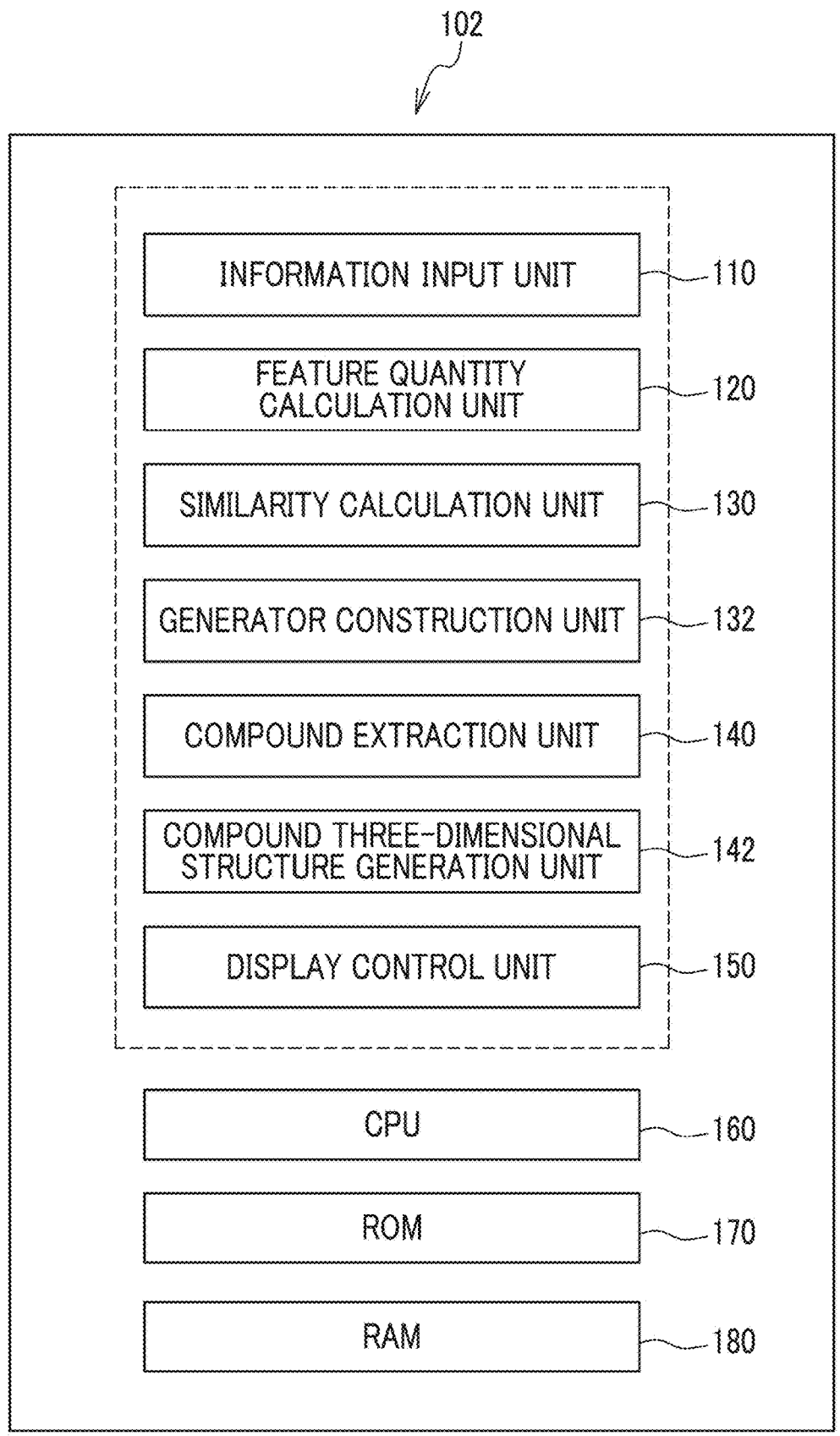
FIG. 29 is a diagram showing a configuration of a processing unit.
Figure 30:
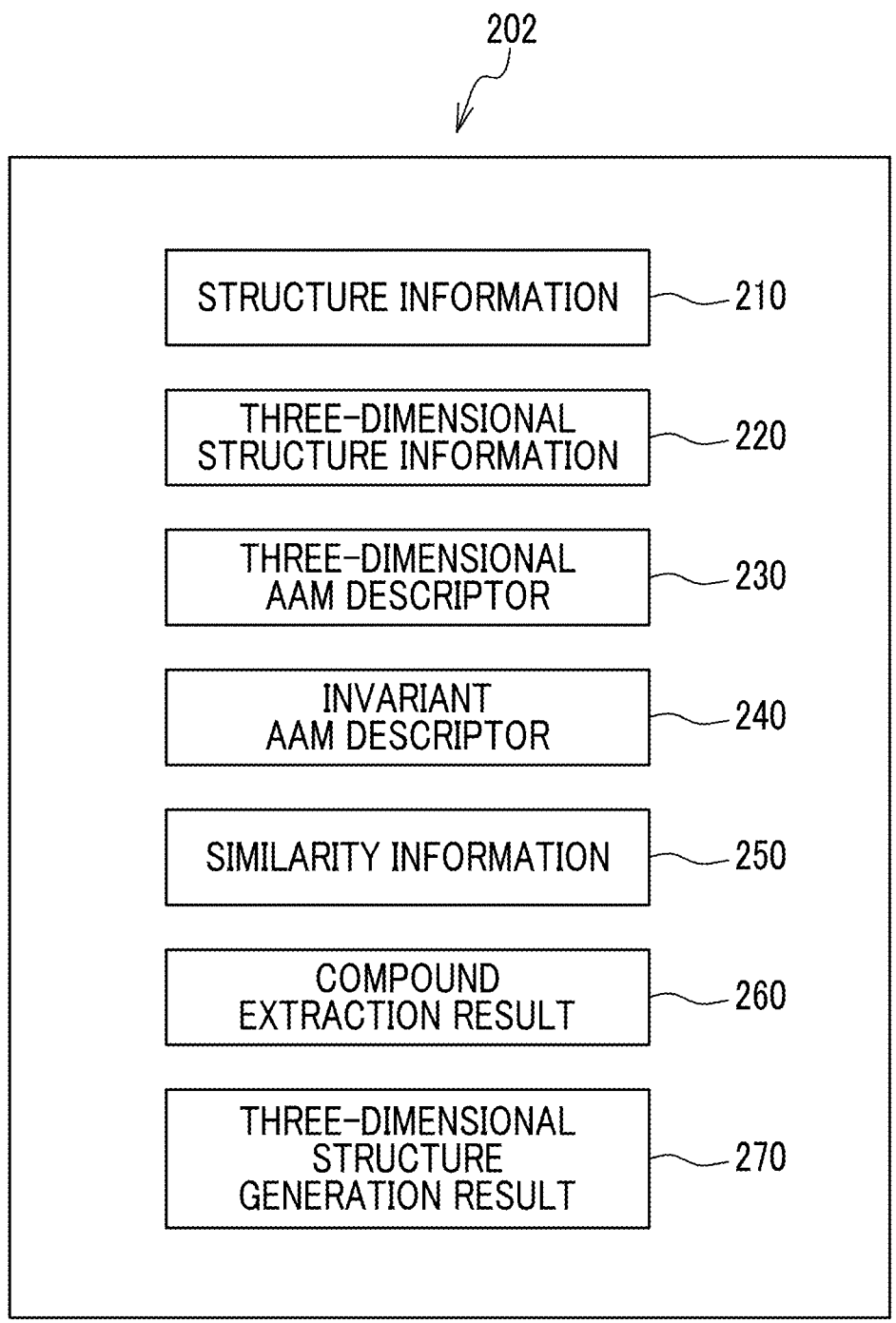
FIG. 30 is a diagram showing information stored in a storage unit.

In addition, in a case where the calculation of a feature quantity, the screening, and the creation of a compound are performed (corresponding to the third embodiment), the calculation, the screening, and the creation can be performed using the same configurations as in FIGS. 28 to 30.

(MODIFICATION EXAMPLE 2) FEATURE QUANTITY OF AMINO ACID AND OTHERS AND USE THEREOF

<Target and Probe>

In Modification Example 2, "composite of proteins and biopolymers other than the proteins (DNA, RNA, cell membranes, and polysaccharides)" are set as targets. Further, "one or more kinds of amino acids" (first probe) and "one or more selected from one or more kinds of nucleic acid bases, one or more kinds of lipid molecules, one or more kinds of monosaccharide molecules, water, and one or more kinds of ions" (second probe; the kind, the number, and the combination thereof may be optional) are set as probes. The configurations of the first and second probes (the kind, the number, and the combination thereof) can be set according to the configurations of the targets. The ions constituting the probes may be monatomic ions or polyatomic ions. Further, all the probes are assumed to generate van der Waals forces.

<Calculation of Feature Quantity and Screening>

The configurations of devices for calculating the feature quantity (the feature quantity according to Modification Example 2) and performing screening (the feature quantity calculating device and the screening device) are the same as those in the first embodiment (see FIGS. 1 to 3). However, a descriptor according to Modification Example 2 (the feature quantity according to Modification Example 2) is calculated and stored instead of the three-dimensional AAM descriptor 230 in FIG. 3, and an invariant feature quantity according to Modification Example 2 is calculated and stored instead of the invariant AAM descriptor 240. The procedures for calculation of the feature quantity and screening are the same as those in the first embodiment, and the feature quantity calculating method, the feature quantity calculating program, the screening method, and the screening program according to the embodiment of the present invention can be used. Specifically, the invariant feature quantity according to Modification Example 2 is calculated (see Equation (2)) by calculating the distribution function (see Equation (1)) using "one or more kinds of amino acids" (the first probe) and "one or more selected from one or more kinds of nucleic acid bases, one or more kinds of lipid molecules, water, one or more kinds of monosaccharide molecules, and one or more kinds of ions" (the second probe; the kind, the number, and the combination thereof may be optional) instead of the "amino acid" as the probe in the calculation of the feature quantity according to Modification Example 2 (see FIG. 5), calculating the feature quantity according to Modification Example 2 from the distribution function, and performing Fourier transform on the feature quantity according to Modification Example 2. Further, the invariant feature quantity according to Modification Example 2 may be calculated by angular integration of the correlation function (see Equations (3) and (4)) using the feature quantity according to Modification Example 2 of two kinds of probes in which at least one of "one or more kinds of amino acids" (first probe) or "one or more selected from one or more kinds of nucleic acid bases, one or more kinds of lipid molecules, one or more kinds of monosaccharide molecules, water, and one or more kinds of ions" (second probe; the kind, the number, and the combination thereof may be optional) is different.

In addition, the target compound can be extracted based on the similarity between the feature quantity according to Modification Example 2 of a plurality of compounds and the feature quantity according to Modification Example 2 of the binding compound using the feature quantity according to Modification Example 2 instead of the three-dimensional AAM descriptor in the first embodiment. A compound having a similarity greater than or equal to the threshold may be extracted, or a compound may be extracted in a descending order of the similarity.

<Calculation of Feature Quantity and Creation of Compound>

The configurations of devices for calculating a feature quantity (the feature quantity according to Modification Example 2) and creating a compound (the feature quantity calculating device and the compound creating device) are the same as those in the second embodiment (see FIGS. 20 to 22). However, the descriptor according to Modification Example 2 (the feature quantity according to Modification Example 2) is calculated and stored instead of the three-dimensional AAM descriptor 230 in FIG. 22, and the invariant feature quantity according to Modification Example 2 is calculated and stored instead of the invariant AAM descriptor 240. The procedures for calculation of the feature quantity and creation of a compound are the same as those in the second embodiment, and the feature quantity calculating method, the feature quantity calculating program, the compound creating method, and the compound creating program according to the embodiment of the present invention can be used. In Modification Example 2, a generator is constructed through machine learning (deep learning) using the three-dimensional structure of the compound as teacher data and the feature quantity according to Modification Example 2 as an explanatory variable, and the three-dimensional structure of the target biopolymer can be generated from the feature quantity according to Modification Example 2 of the binding compound that is a compound whose binding to the target biopolymer has been confirmed using the constructed generator. Further, similar to the first to third embodiments and Modification Example 1, a compound having a three-dimensional structure with different features can be generated by selecting features of a compound to be provided as teacher data.

In the same manner as in the first to third embodiments and Modification Example 1 described above, since the drug efficacy of a compound (the binding force with respect to the target) is locally exhibited as the result of an interaction between a compound and a probe, in a case where the degree of accumulation of probes is similar between compounds, the compounds have similar binding forces with respect to the targets. That is, the compounds with similar feature quantities according to Modification Example 2 exhibit similar drug efficacies. Therefore, in Modification Example 2, the chemical properties of the compound can be accurately exhibited by the feature quantity according to Modification Example 2. In addition, in a case where the feature quantities according to Modification Example 2 are similar between the target compound and the binding compound that is bound to the target biopolymer, the drug efficacies of both the binding compound and the target compound are similar. Therefore, according to Modification Example 2, a target compound having drug efficacy similar to that of the binding compound is extracted based on the feature quantity according to Modification Example 2 so that screening of a pharmaceutical candidate compound can be efficiently performed. Further, according to Modification Example 2, similarly to the above-described embodiments and Modification Example 1, a structural formula of a compound having a feature quantity similar to the feature quantity (the feature quantity according to Modification Example 2) of the binding compound (accordingly, the drug efficacies are similar) is generated without performing search, and thus the three-dimensional structure of the pharmaceutical candidate compound can be efficiently created.

In addition, in a case where the calculation of a feature quantity, the screening, and the creation of a compound are performed (corresponding to the third embodiment), the calculation, the screening, and the creation can be performed using the same configurations as in FIGS. 28 to 30.

(MODIFICATION EXAMPLE 3) FEATURE QUANTITY OF VIRTUAL POINT ELECTRIC CHARGE AND THE LIKE AND USE THEREOF

<Target and Probe>

In Modification Example 3, a biopolymer (compound) is used as the target, and "one or more selected from a first point electric charge having an electric charge of +1, a second point electric charge having an electric charge of −1, a third point electric charge having an electric charge of +0.1, a fourth point electric charge having an electric charge of −0.1, and a fifth point electric charge having an electric charge of 0 (the kind, the number, and the combination thereof may be optional)" (virtual point electric charges having a real electric charge and generating a van der Waals force) are used as the probes. These point electric charges are an example of the "single point".

<Calculation of Feature Quantity and Screening>

The configurations of devices for calculating the feature quantity (the feature quantity according to Modification Example 3; the second feature quantity and the second invariant feature quantity) and performing screening (the feature quantity calculating device and the screening device) are the same as those in the first embodiment (see FIGS. 1 to 3). However, a second descriptor (the second feature quantity) is calculated and stored instead of the three-dimensional AAM descriptor 230 in FIG. 3, and a second invariant feature quantity is calculated and stored instead of the invariant AAM descriptor 240. The procedures for calculation of the feature quantity and screening are the same as those in the first embodiment, and the feature quantity calculating method, the feature quantity calculating program, the screening method, and the screening program according to the embodiment of the present invention can be used. Specifically, the second invariant feature quantity is calculated (see Equation (2)) by calculating the distribution function (see Equation (1)) using "one or more selected from a first point electric charge having an electric charge of +1, a second point electric charge having an electric charge of −1, a third point electric charge having an electric charge of +0.1, a fourth point electric charge having an electric charge of −0.1, and a fifth point electric charge having an electric charge of 0 (the kind, the number, and the combination thereof may be optional)" instead of the "amino acid" as the probe in the calculation of the feature quantity according to the first embodiment (see FIG. 5), calculating the second feature quantity from the distribution function, and performing Fourier transform on the second feature quantity. Further, the second invariant feature quantity may be calculated by angular integration of the correlation function (see Equations (3) and (4)) using the second feature quantity of two different kinds of probes (the first probe formed of one or more selected from the first point electric charge, the second point electric charge, the third point electric charge, the fourth point electric charge, and the fifth point electric charge and the second probe that is formed of one or more selected from the first point electric charge, the second point electric charge, the third point electric charge, the fourth point electric charge, and the fifth point electric charge and different from the first probe).

In addition, the target compound can be extracted based on the similarity between the second feature quantity of a plurality of compounds and the second feature quantity of the binding compound using the second feature quantity instead of the three-dimensional AAM descriptor in the first embodiment. A compound having a similarity greater than or equal to the threshold may be extracted, or a compound may be extracted in a descending order of the similarity.

<Calculation of Feature Quantity and Creation of Compound>

The configurations of devices for calculating a feature quantity (the second feature quantity) and creating a compound (the feature quantity calculating device and the compound creating device) are the same as those in the second embodiment (see FIGS. 20 to 22). However, the second descriptor (the second feature quantity) is calculated and stored instead of the three-dimensional AAM descriptor 230 in FIG. 22, and the second invariant feature quantity is calculated and stored instead of the invariant AAM descriptor 240. The procedures for calculation of the feature quantity and creation of a compound are the same as those in the second embodiment, and the feature quantity calculating method, the feature quantity calculating program, the compound creating method, and the compound creating program according to the embodiment of the present invention can be used. In Modification Example 3, a generator is constructed through machine learning (deep learning) using the three-dimensional structure of the compound as teacher data and the second feature quantity as an explanatory variable, and the three-dimensional structure of the target biopolymer can be generated from the second feature quantity of the binding compound that is a compound whose binding to the target biopolymer has been confirmed using the constructed generator. Further, similar to the first to third embodiments and Modification Examples 1 and 2, a compound having a three-dimensional structure with different features can be generated by selecting features of a compound to be provided as teacher data.

In the same manner as in the first to third embodiments and Modification Examples 1 and 2 described above, since the drug efficacy of a compound (the binding force with respect to the target) is locally exhibited as the result of an interaction between a compound and a probe, in a case where the degree of accumulation of probes is similar between compounds, the compounds have similar binding forces with respect to the targets. That is, compounds having similar second feature quantities exhibit similar drug efficacies. Therefore, in Modification Example 3, the chemical properties of the compound can be accurately exhibited by the second feature quantity. In addition, in a case where the second feature quantities are similar between the target compound and the binding compound that is bound to the target biopolymer, the drug efficacies of both the binding compound and the target compound are similar. Therefore, according to Modification Example 3, a target compound having drug efficacy similar to that of the binding compound is extracted based on the second feature quantity so that screening of a pharmaceutical candidate compound can be efficiently performed. Further, according to Modification Example 3, similarly to the above-described first to third embodiments and Modification Examples 1 and 2, a structural formula of a compound having a feature quantity similar to the feature quantity (the second feature quantity) of the binding compound (accordingly, the drug efficacies are similar) is generated without performing search, and thus the three-dimensional structure of the pharmaceutical candidate compound can be efficiently created.

In addition, in a case where the calculation of a feature quantity, the screening, and the creation of a compound are performed (corresponding to the third embodiment), the calculation, the screening, and the creation can be performed using the same configurations as in FIGS. 28 to 30.

(MODIFICATION EXAMPLE 4) FEATURE QUANTITY OF AMINO ACID AND VIRTUAL POINT ELECTRIC CHARGE AND USE THEREOF

<Target and Probe>

In Modification Example 4, a biopolymer (compound) is used as the target, and "a first probe that is one or more kinds of amino acids and a second probe that is one or more selected from a first point electric charge having an electric charge of +1, a second point electric charge having an electric charge of −1, a third point electric charge having an electric charge of +0.1, a fourth point electric charge having an electric charge of −0.1, a dipole in which the first point electric charge and the second point electric charge are disposed to be separated from each other, and a fifth point electric charge having an electric charge of 0 (the kind, the number, and the combination thereof may be optional)" are used as the probes. The second probe may be formed of point electric charges (one or more of the first to fifth point electric charges) excluding the dipole. The first to fifth point electric charges are an example of the "single point".

<Calculation of Feature Quantity and Screening>

The configurations of devices for calculating the feature quantity (the feature quantity according to Modification Example 4) and performing screening (the feature quantity calculating device and the screening device) are the same as those in the first embodiment (see FIGS. 1 to 3). However, a descriptor according to Modification Example 4 (the feature quantity according to Modification Example 4) is calculated and stored instead of the three-dimensional AAM descriptor 230 in FIG. 3, and an invariant feature quantity according to Modification Example 4 is calculated and stored instead of the invariant AAM descriptor 240. The procedures for calculation of the feature quantity and screening are the same as those in the first embodiment, and the feature quantity calculating method, the feature quantity calculating program, the screening method, and the screening program according to the embodiment of the present invention can be used. Specifically, the invariant feature quantity according to Modification Example 4 is calculated (see Equation (2)) by calculating the distribution function (see Equation (1)) using "a first probe that is formed of one or more kinds of amino acids and a second probe that is formed of one or more selected from a first point electric charge having an electric charge of +1, a second point electric charge having an electric charge of −1, a third point electric charge having an electric charge of +0.1, a fourth point electric charge having an electric charge of −0.1, a dipole in which the first point electric charge and the second point electric charge are disposed to be separated from each other, and a fifth point electric charge having an electric charge of 0 (the kind, the number, and the combination thereof may be optional)" instead of the "amino acid" as the probe in the calculation of the feature quantity according to the first embodiment (see FIG. 5), calculating the feature quantity according Modification Example 4 from the distribution function, and performing Fourier transform on the feature quantity according Modification Example 4. The second probe may be formed of point electric charges (one or more of the first to fifth point electric charges) excluding the dipole. Further, the invariant feature quantity according Modification Example 4 may be calculated by angular integration of the correlation function (see Equations (3) and (4)) using the feature quantity according Modification Example 4 of two kinds of probes in which at least one of the first probe or the second probe is different.

In addition, the target compound can be extracted based on the similarity between the feature quantity according Modification Example 4 of a plurality of compounds and the feature quantity according Modification Example 4 of the binding compound using the feature quantity according Modification Example 4 instead of the three-dimensional AAM descriptor in the first embodiment. A compound having a similarity greater than or equal to the threshold may be extracted, or a compound may be extracted in a descending order of the similarity.

<Calculation of Feature Quantity and Creation of Compound>

The configurations of devices for calculating a feature quantity (the feature quantity according Modification Example 4) and creating a compound (the feature quantity calculating device and the compound creating device) are the same as those in the second embodiment (see FIGS. 20 to 22). However, the descriptor according to Modification Example 4 (the feature quantity according to Modification Example 4) is calculated and stored instead of the three-dimensional AAM descriptor 230 in FIG. 22, and the invariant feature quantity according to Modification Example 4 is calculated and stored instead of the invariant AAM descriptor 240. The procedures for calculation of the feature quantity and creation of a compound are the same as those in the second embodiment, and the feature quantity calculating method, the feature quantity calculating program, the compound creating method, and the compound creating program according to the embodiment of the present invention can be used. In Modification Example 4, a generator is constructed through machine learning (deep learning) using the three-dimensional structure of the compound as teacher data and the feature quantity according to Modification Example 4 as an explanatory variable, and the three-dimensional structure of the target biopolymer can be generated from the feature quantity according to Modification Example 4 of the binding compound that is a compound whose binding to the target biopolymer has been confirmed using the constructed generator. Further, similar to the first to third embodiments, a compound having a three-dimensional structure with different features can be generated by selecting features of a compound to be provided as teacher data.

In the same manner as in the first to third embodiments, since the drug efficacy of a compound (the binding force with respect to the target) is locally exhibited as the result of an interaction between a compound and a probe, in a case where the degree of accumulation of probes is similar between compounds, the compounds have similar binding forces with respect to the targets. That is, the compounds with similar feature quantities according to Modification Example 4 exhibit similar drug efficacies. Therefore, in Modification Example 4, the chemical properties of the compound can be accurately exhibited by the feature quantity according to Modification Example 4. In addition, in a case where the feature quantities according to Modification Example 4 are similar between the target compound and the binding compound that is bound to the target biopolymer, the drug efficacies of both the binding compound and the target compound are similar. Therefore, according to Modification Example 4, a target compound having drug efficacy similar to that of the binding compound is extracted based on the feature quantity according to Modification Example 4 so that screening of a pharmaceutical candidate compound can be efficiently performed. Further, according to Modification Example 4, similarly to the above-described embodiments, a structural formula of a compound having a feature quantity similar to the feature quantity (the feature quantity according to Modification Example 4) of the binding compound (accordingly, the drug efficacies are similar) is generated without performing search, and thus the three-dimensional structure of the pharmaceutical candidate compound can be efficiently created.

In addition, in a case where the calculation of a feature quantity, the screening, and the creation of a compound are performed (corresponding to the third embodiment), the calculation, the screening, and the creation can be performed using the same configurations as in FIGS. 28 to 30.

(MODIFICATION EXAMPLE 5) FEATURE QUANTITY OF NUCLEIC ACID BASE AND VIRTUAL POINT ELECTRIC CHARGE AND USE THEREOF

<Target and Probe>

In Modification Example 5, a biopolymer (compound) is used as the target, and a first probe "that is one or more selected from one or more kinds of nucleic acid bases, one or more kinds of lipid molecules, water, one or more kinds of monosaccharide molecules, and one or more kinds of ions (the kind, the number, and the combination thereof may be optional)" and a second probe "that is one or more selected from a first point electric charge having an electric charge of +1, a second point electric charge having an electric charge of −1, a third point electric charge having an electric charge of +0.1, a fourth point electric charge having an electric charge of −0.1, a dipole in which the first point electric charge and the second point electric charge are disposed to be separated from each other, and a fifth point electric charge having an electric charge of 0 (the kind, the number, and the combination thereof may be optional)" are used as the probes. The first probe may be formed of one or more kinds of monatomic ions, and the second probe may be formed of point electric charges (one or more of the first to fifth point electric charges). The "monatomic ions" and the "point electric charges" are an example of the "single point".

<Calculation of Feature Quantity and Screening>

The configurations of devices for calculating the feature quantity (the feature quantity according to Modification Example 5; the third feature quantity and the third invariant feature quantity) and performing screening (the feature quantity calculating device and the screening device) are the same as those in the first embodiment (see FIGS. 1 to 3). However, a third descriptor (third feature quantity) is calculated and stored instead of the three-dimensional AAM descriptor 230 in FIG. 3, and a third invariant feature quantity is calculated and stored instead of the invariant AAM descriptor 240. The procedures for calculation of the feature quantity and screening are the same as those in the first embodiment, and the feature quantity calculating method, the feature quantity calculating program, the screening method, and the screening program according to the embodiment of the present invention can be used. Specifically, the third invariant feature quantity is calculated (see Equation (2)) by calculating the distribution function (see Equation (1)) using the, first probe "that is formed of one or more selected from one or more kinds of nucleic acid bases, one or more kinds of lipid molecules, water, one or more kinds of monosaccharide molecules, and one or more kinds of ions (the kind, the number, and the combination thereof may be optional)" and the second probe "that is formed of one or more selected from a first point electric charge having an electric charge of +1, a second point electric charge having an electric charge of −1, a third point electric charge having an electric charge of +0.1, a fourth point electric charge having an electric charge of −0.1, a dipole in which the first point electric charge and the second point electric charge are disposed to be separated from each other, and a fifth point electric charge having an electric charge of 0 (the kind, the number, and the combination thereof may be optional)" instead of the "amino acid" as the probe in the calculation of the feature quantity according to the first embodiment (see FIG. 5), calculating the third feature quantity from the distribution function, and performing Fourier transform on the third feature quantity. Further, the third invariant feature quantity may be calculated by angular integration of the correlation function (see Equations (3) and (4)) using the third feature quantity of two kinds of probes in which at least one of the first probe or the second probe is different. As described above, the first probe may be formed of one or more kinds of monatomic ions, and the second probe may be formed of point electric charges (one or more of the first to fifth point electric charges). The "monatomic ions" and the "point electric charges" are an example of the "single point".

In addition, the target compound can be extracted based on the similarity between the third feature quantity of a plurality of compounds and the third feature quantity of the binding compound using the third feature quantity instead of the three-dimensional AAM descriptor in the first embodiment. A compound having a similarity greater than or equal to the threshold may be extracted, or a compound may be extracted in a descending order of the similarity.

<Calculation of Feature Quantity and Creation of Compound>

The configurations of devices for calculating a feature quantity (third feature quantity) and creating a compound (the feature quantity calculating device and the compound creating device) are the same as those in the second embodiment (see FIGS. 20 to 22). However, the third descriptor (third feature quantity) is calculated and stored instead of the three-dimensional AAM descriptor 230 in FIG. 22, and the third invariant feature quantity is calculated and stored instead of the invariant AAM descriptor 240. The procedures for calculation of the feature quantity and creation of a compound are the same as those in the second embodiment, and the feature quantity calculating method, the feature quantity calculating program, the compound creating method, and the compound creating program according to the embodiment of the present invention can be used. In Modification Example 5, a generator is constructed through machine learning (deep learning) using the three-dimensional structure of the compound as teacher data and the third feature quantity as an explanatory variable, and the three-dimensional structure of the target biopolymer can be generated from the third feature quantity of the binding compound that is a compound whose binding to the target biopolymer has been confirmed using the constructed generator. Further, similar to the first to third embodiments, a compound having a three-dimensional structure with different features can be generated by selecting features of a compound to be provided as teacher data.

In the same manner as in the first to third embodiments, since the drug efficacy of a compound (the binding force with respect to the target) is locally exhibited as the result of an interaction between a compound and a probe, in a case where the degree of accumulation of probes is similar between compounds, the compounds have similar binding forces with respect to the targets. That is, compounds having similar third feature quantities exhibit similar drug efficacies. Therefore, in Modification Example 5, the chemical properties of the compound can be accurately exhibited by the third feature quantity. In addition, in a case where the third feature quantities are similar between the target compound and the binding compound that is bound to the target biopolymer, the drug efficacies of both the binding compound and the target compound are similar. Therefore, according to Modification Example 5, a target compound having drug efficacy similar to that of the binding compound is extracted based on the third feature quantity so that screening of a pharmaceutical candidate compound can be efficiently performed. Further, according to Modification Example 5, similarly to the above-described embodiments, a structural formula of a compound having a feature quantity similar to the feature quantity (the third feature quantity) of the binding compound (accordingly, the drug efficacies are similar) is generated without performing search, and thus the three-dimensional structure of the pharmaceutical candidate compound can be efficiently created.

In addition, in a case where the calculation of a feature quantity, the screening, and the creation of a compound are performed (corresponding to the third embodiment), the calculation, the screening, and the creation can be performed using the same configurations as in FIGS. 28 to 30.

(MODIFICATION EXAMPLE 6) FEATURE QUANTITIES OF AMINO ACID, NUCLEIC ACID BASE, AND VIRTUAL POINT ELECTRIC CHARGE AND USE THEREOF

<Target and Probe>

In Modification Example 6, a biopolymer (compound) is used as the target, and a first probe "that is one or more kinds of amino acids", a second probe "that is one or more selected from one or more kinds of nucleic acid bases, one or more kinds of lipid molecules, water, one or more kinds of monosaccharide molecules, and one or more kinds of ions (the kind, the number, and the combination thereof may be optional)", and a third probe "that is one or more selected from a first point electric charge having an electric charge of +1, a second point electric charge having an electric charge of −1, a third point electric charge having an electric charge of +0.1, a fourth point electric charge having an electric charge of −0.1, a dipole in which the first point electric charge and the second point electric charge are disposed to be separated from each other, and a fifth point electric charge having an electric charge of 0 (the kind, the number, and the combination thereof may be optional)" are used as the probes. The second probe may be formed of one or more kinds of monatomic ions, and the third probe may be formed of one or more of the first to fifth point electric charges. The "monatomic ions" and the "point electric charges" are an example of the "single point".

<Calculation of Feature Quantity and Screening>

The configurations of devices for calculating the feature quantity (the feature quantity according to Modification Example 6) and performing screening (the feature quantity calculating device and the screening device) are the same as those in the first embodiment (see FIGS. 1 to 3). However, a descriptor according to Modification Example 6 (the feature quantity according Modification Example 6) is calculated and stored instead of the three-dimensional AAM descriptor 230 in FIG. 3, and an invariant feature quantity according to Modification Example 6 is calculated and stored instead of the invariant AAM descriptor 240. The procedures for calculation of the feature quantity and screening are the same as those in the first embodiment, and the feature quantity calculating method, the feature quantity calculating program, the screening method, and the screening program according to the embodiment of the present invention can be used. Specifically, the invariant feature quantity according to Modification Example 6 is calculated (see Equation (2)) by calculating the distribution function (see Equation (1)) using the first probe "that is formed of one or more kinds of amino acids", the second probe "that is formed of one or more selected from one or more kinds of nucleic acid bases, one or more kinds of lipid molecules, water, one or more kinds of monosaccharide molecules, and one or more kinds of ions (the kind, the number, and the combination thereof may be optional)", and a third probe "that is formed of one or more selected from a first point electric charge having an electric charge of +1, a second point electric charge having an electric charge of −1, a third point electric charge having an electric charge of +0.1, a fourth point electric charge having an electric charge of −0.1, a dipole in which the first point electric charge and the second point electric charge are disposed to be separated from each other, and a fifth point electric charge having an electric charge of 0 (the kind, the number, and the combination thereof may be optional)" instead of the "amino acid" as the probe in the calculation of the feature quantity according to the first embodiment (see FIG. 5), calculating the feature quantity according to Modification Example 6 from the distribution function, and performing Fourier transform on the feature quantity according to Modification Example 6. Further, the invariant feature quantity according to Modification Example 6 may be calculated by angular integration of the correlation function (see Equations (3) and (4)) using the feature quantity according to Modification Example 6 of two kinds of probes in which at least one of the first probe, the second probe, or the third probe is different. As described above, the second probe may be formed of one or more kinds of monatomic ions, and the third probe may be formed of one or more of the first to fifth point electric charges.

In addition, the target compound can be extracted based on the similarity between the feature quantity according to Modification Example 6 of a plurality of compounds and the feature quantity according to Modification Example 6 of the binding compound using the feature quantity according to Modification Example 6 instead of the three-dimensional AAM descriptor in the first embodiment. A compound having a similarity greater than or equal to the threshold may be extracted, or a compound may be extracted in a descending order of the similarity.

<Calculation of Feature Quantity and Creation of Compound>

The configurations of devices for calculating a feature quantity (the feature quantity according to Modification Example 6) and creating a compound (the feature quantity calculating device and the compound creating device) are the same as those in the second embodiment (see FIGS. 20 to 22). However, a descriptor according to Modification Example 6 (the feature quantity according to Modification Example 6) is calculated and stored instead of the three-dimensional AAM descriptor 230 in FIG. 22, and an invariant feature quantity according to Modification Example 6 is calculated and stored instead of the invariant AAM descriptor 240. The procedures for calculation of the feature quantity and creation of a compound are the same as those in the second embodiment, and the feature quantity calculating method, the feature quantity calculating program, the compound creating method, and the compound creating program according to the embodiment of the present invention can be used. In Modification Example 6, a generator is constructed through machine learning (deep learning) using the three-dimensional structure of the compound as teacher data and the feature quantity according to Modification Example 6 as an explanatory variable, and the three-dimensional structure of the target biopolymer can be generated from the feature quantity according to Modification Example 6 of the binding compound that is a compound whose binding to the target biopolymer has been confirmed using the constructed generator. Further, similar to the first to third embodiments, a compound having a three-dimensional structure with different features can be generated by selecting features of a compound to be provided as teacher data.

In the same manner as in the first to third embodiments, since the drug efficacy of a compound (the binding force with respect to the target) is locally exhibited as the result of an interaction between a compound and a probe, in a case where the degree of accumulation of probes is similar between compounds, the compounds have similar binding forces with respect to the targets. That is, the compounds with similar feature quantities according to Modification Example 6 exhibit similar drug efficacies. Therefore, in Modification Example 6, the chemical properties of the compound can be accurately exhibited by the feature quantity according to Modification Example 6. In addition, in a case where the feature quantities according to Modification Example 6 are similar between the target compound and the binding compound that is bound to the target biopolymer, the drug efficacies of both the binding compound and the target compound are similar. Therefore, according to Modification Example 6, a target compound having drug efficacy similar to that of the binding compound is extracted based on the feature quantity according to Modification Example 6 so that screening of a pharmaceutical candidate compound can be efficiently performed. Further, according to Modification Example 6, similarly to the above-described embodiments, a structural formula of a compound having a feature quantity similar to the feature quantity (the feature quantity according to Modification Example 6) of the binding compound (accordingly, the drug efficacies are similar) is generated without performing search, and thus the three-dimensional structure of the pharmaceutical candidate compound can be efficiently created.

In addition, in a case where the calculation of a feature quantity, the screening, and the creation of a compound are performed (corresponding to the third embodiment), the calculation, the screening, and the creation can be performed using the same configurations as in FIGS. 28 to 30.

(MODIFICATION EXAMPLE 7) FEATURE QUANTITIES OF MONATOMIC IONS AND USE THEREOF

<Target and Probe>

In Modification Example 7, a compound is used as the target, and "one or more kinds of monatomic ions" are used as probes. The monatomic ions are an example of the "single point".

<Calculation of Feature Quantity and Screening>

The configurations of devices for calculating the feature quantity (the feature quantity according to Modification Example 7; the first feature quantity and the first invariant feature quantity) and performing screening (the feature quantity calculating device and the screening device) are the same as those in the first embodiment (see FIGS. 1 to 3). However, the first descriptor (the first feature quantity) is calculated and stored instead of the three-dimensional AAM descriptor 230 in FIG. 3, and the first invariant feature quantity is calculated and stored instead of the invariant AAM descriptor 240. The procedures for calculation of the feature quantity and screening are the same as those in the first embodiment, and the feature quantity calculating method, the feature quantity calculating program, the screening method, and the screening program according to the embodiment of the present invention can be used. Specifically, the first invariant feature quantity is calculated (see Equation (2)) by calculating the distribution function (see Equation (1)) using "one or more kinds of monatomic ions (the kind, the number, and the combination thereof may be optional)" instead of the "amino acid" as the probe in the calculation of the feature quantity according to the first embodiment (see FIG. 5), calculating the first feature quantity from the distribution function, and performing Fourier transform on the first feature quantity. Further, the first invariant feature quantity may be calculated by angular integration of the correlation function (see Equations (3) and (4)) using the first feature quantity of two kinds of probes (the first probe formed of one or more kinds of monatomic ions and the second probe formed of one or more kinds of monatomic ions and different from the first probe) in which at least one of the first probe or the second probe is different.

<Comparison of Number of Hits Based on Each Feature Quantity>

Figure 31:
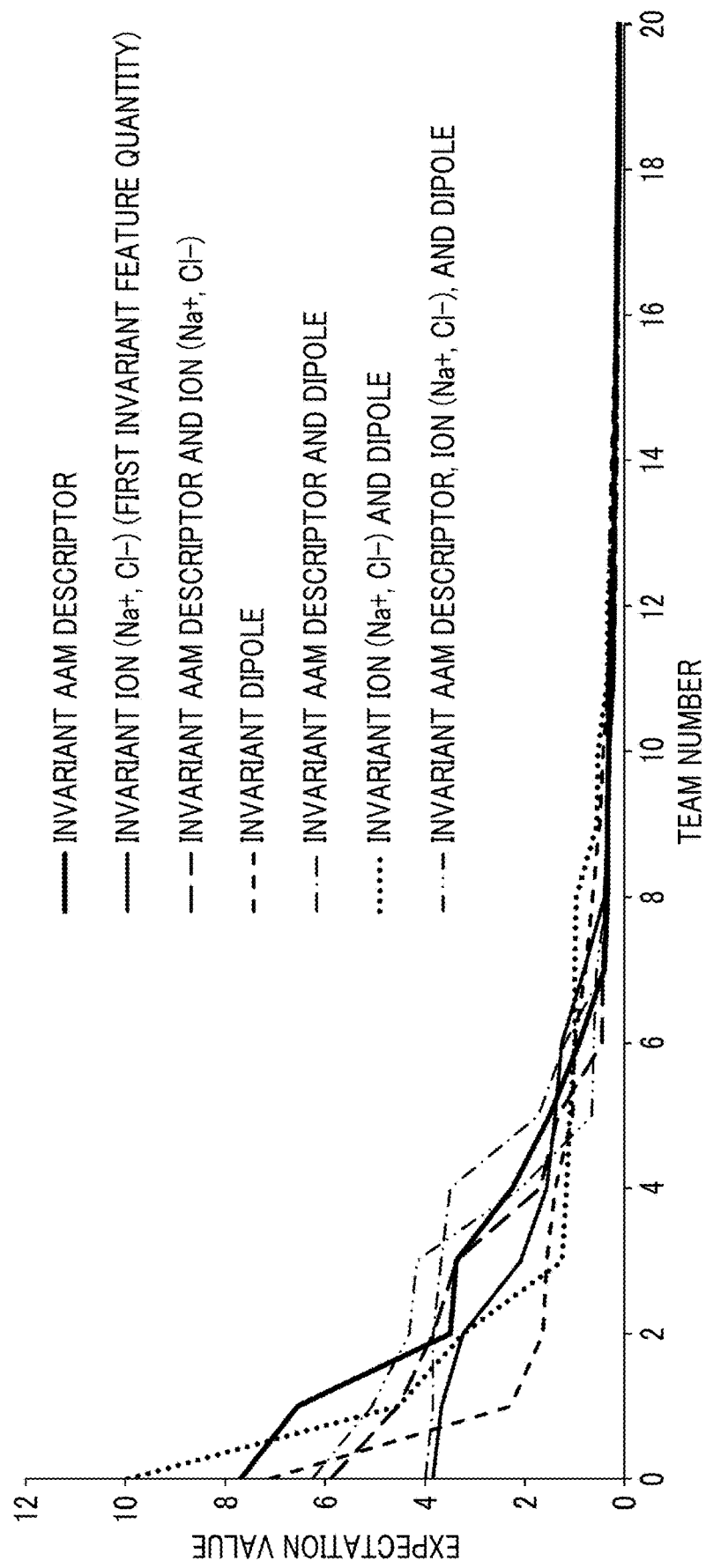
FIG. 31 is a diagram showing a comparison result of easiness of finding a hit.

FIG. 31 is a diagram showing an example of a result of comparative evaluation of the easiness of finding hits based on an invariant feature quantity (an invariant feature quantity using an amino acid as a probe and invariant feature quantities using those other than the amino acid as probes) using a compound as a target structure for the same system (protein ABL1) as in FIG. 13 described above. As shown in FIG. 31, although there is a difference in the effect (the expectation value of the number of hits) depending on the kind of descriptor (feature quantity), it can be seen that the expectation value is improved as compared with the random case (see FIG. 13). Further, FIG. 31 shows a result of clustering with (the number of teams=183), and thus the result (clustering with the number of teams=221) is different from the above-described result in a case where the number of hits for "AAM" is as shown in FIG. 13. As described above, even in a case where the invariant feature quantities using those other than the amino acid as probes are used, screening of a pharmaceutical candidate compound can be efficiently performed.

Additional Note

In addition to the aspects described above, the configurations described below are also included in the scope of the present invention. Further, the specific embodiments of the methods, devices, and programs described below are the same as those of the first to third embodiments.

(Additional Note 1)

In the feature quantity calculating device according to an additional note 1, in the ninth aspect, the target structure designation unit designates a compound as the target structure, the three-dimensional structure generation unit generates a three-dimensional structure of the compound formed of a plurality of atoms, the feature quantity calculation unit calculates the first feature quantity which is a feature quantity obtained by quantifying, in the three-dimensional space, the degree of accumulation of the probes in the periphery of the three-dimensional structure of the compound generated by the three-dimensional structure generation unit which is the degree of accumulation using one or more kinds of monatomic ions as the probes, and the invariant conversion unit calculates the first invariant feature quantity by converting the first feature quantity into an invariant with respect to rotation and translation of the compound. According to the configuration of the additional note 1, similarly to the second aspect described above, the feature quantity accurately showing the chemical properties of the compound can be calculated.

(Additional Note 2)

In the feature quantity calculating device according to an additional note 2, in the additional note 1, the feature quantity calculation unit calculates the first feature quantity of the first probe that is formed of the one or more kinds of monatomic ions and the second probe that is formed of the one or more kinds of monatomic ions and different from the first probe, and the invariant conversion unit calculates the first invariant feature quantity using the first feature quantity of the first probe and the first feature quantity of the second probe. According to the configuration of the additional note 2, similar to the third aspect described above, the comparison of compounds (determination of the drug efficacy) can be accurately performed based on the feature quantity (the first invariant feature quantity).

(Additional Note 3)

In the feature quantity calculating device according to an additional note 3, in the additional note 1, the target structure designation unit designates a compound as the target structure, the three-dimensional structure generation unit generates a three-dimensional structure of the compound formed of a plurality of atoms, the feature quantity calculation unit calculates the second feature quantity which is a feature quantity obtained by quantifying, in the three-dimensional space, the degree of accumulation of the probes in the periphery of the three-dimensional structure of the compound generated by the three-dimensional structure generation unit which is the degree of accumulation using one or more selected from a first point electric charge having an electric charge of +1, a second point electric charge having an electric charge of −1, a third point electric charge having an electric charge of +0.1, a fourth point electric charge having an electric charge of −0.1, and a fifth point electric charge having an electric charge of 0, as the probes, and the invariant conversion unit calculates the second invariant feature quantity by converting the second feature quantity into an invariant with respect to rotation and translation of the compound. According to the configuration of the additional note 3, similarly to the fourth aspect described above, the feature quantity accurately showing the chemical properties of the target structure can be calculated.

Figure 32:
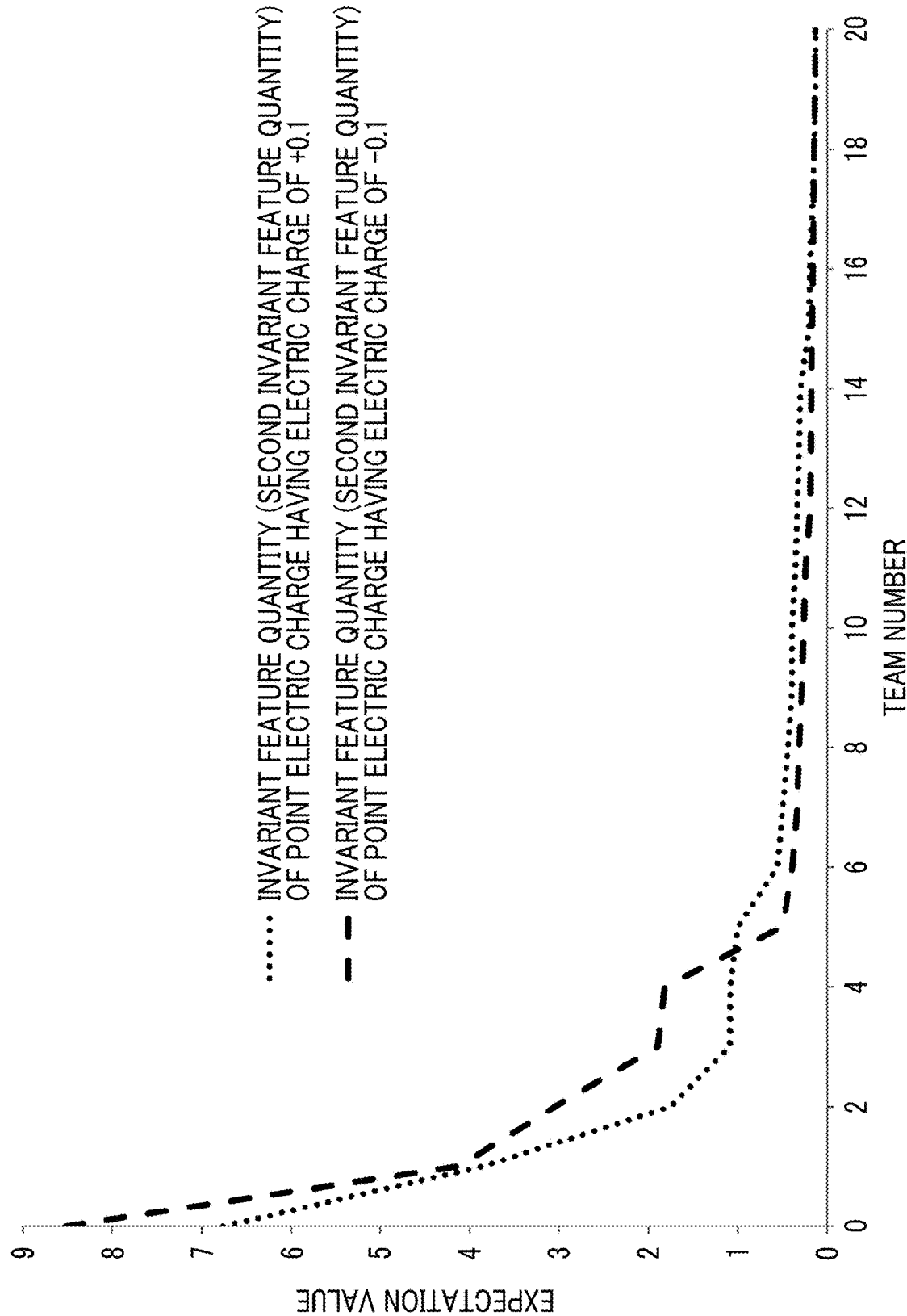
FIG. 32 is another diagram showing a comparison result of easiness of finding a hit.

FIG. 32 is a diagram showing an example of a result of comparative evaluation of the easiness of finding hits based on an invariant feature quantity using a compound as a target structure for the same system (protein ABL1) as in FIGS. 13 and 31 described above. Specifically, FIG. 32 shows the evaluation result of the invariant feature quantity (the second invariant feature quantity) using the point electric charge (the third point electric charge) having an electric charge of +0.1 as a probe and the invariant feature quantity (the second invariant feature quantity) using the point electric charge (the fourth point electric charge) having an electric charge of −0.1 as a probe. As shown in FIG. 32, although there is a difference in the effect (the expectation value of the number of hits) depending on the kind of descriptor (feature quantity), it can be seen that the expectation value is improved as compared with the random case (see FIG. 13). As described above, even in a case where an invariant feature quantity using a point electric charge as a probe is used, screening of a pharmaceutical candidate compound can be efficiently performed.

(Additional Note 4)

In the feature quantity calculating device according to an additional note 4, in the additional note 3, the feature quantity calculation unit calculates the second feature quantity of the first probe that is formed of one or more selected from the first point electric charge, the second point electric charge, the third point electric charge, the fourth point electric charge, and the fifth point electric charge and the second probe that is formed of one or more selected from the first point electric charge, the second point electric charge, the third point electric charge, the fourth point electric charge, and the fifth point electric charge and different from the first probe, and the invariant conversion unit calculates the second invariant feature quantity using the second feature quantity of the first probe and the second feature quantity of the second probe. According to the configuration of the additional note 4, similar to the fifth aspect described above, the comparison of compounds (determination of the drug efficacy) can be accurately performed based on the feature quantity (the second invariant feature quantity).

(Additional Note 5)

In the feature quantity calculating device according to an additional note 5, in the additional note 4, the target structure designation unit designates a compound as the target structure, the three-dimensional structure generation unit generates a three-dimensional structure of the compound formed of a plurality of atoms, the feature quantity calculation unit calculates the third feature quantity which is a feature quantity obtained by quantifying, in the three-dimensional space, the degree of accumulation of the probes in the periphery of the three-dimensional structure of the compound generated by the three-dimensional structure generation unit which is the degree of accumulation using the first probe that is formed of one or more kinds of monatomic ions and the second probe that is formed of one or more selected from a first point electric charge having an electric charge of +1, a second point electric charge having an electric charge of −1, a third point electric charge having an electric charge of +0.1, a fourth point electric charge having an electric charge of −0.1, and a fifth point electric charge having an electric charge of 0 as the probes, and the invariant conversion unit calculates the third invariant feature quantity using the third feature quantity of the first probe and the third feature quantity of the second probe.

(Additional Note 6)

In the feature quantity calculating device according to an additional note 6, in the additional note 5, the feature quantity calculation unit calculates the third feature quantity of two kinds of the probes in which at least one of the first probe or the second probe is different, and the invariant conversion unit calculates the third invariant feature quantity using the third feature quantity of two different kinds of the probes. According to the configuration of the additional note 6, similar to the seventh aspect described above, the comparison of compounds (determination of the drug efficacy) can be accurately performed based on the feature quantity (the third invariant feature quantity).

(Additional Note 7)

The feature quantity calculating method according to an additional note 7 is a feature quantity calculating method including a target structure designating step of designating a target structure formed of a plurality of unit structures having chemical properties, a three-dimensional structure generating step of generating a three-dimensional structure using the plurality of unit structures for the target structure, and a feature quantity calculating step of calculating a feature quantity obtained by quantifying, in a three-dimensional space, the degree of accumulation of one or more kinds of probes in the periphery of the three-dimensional structure, in which the probes include a first probe that is a single point having a real electric charge and generating a van der Waals force and a second probe in which a plurality of points having a real electric charge and generating a van der Waals force are disposed to be separated from each other. According to the configuration of the additional note 7, similarly to the first aspect described above, the feature quantity accurately showing the chemical properties of the target structure can be calculated.

(Additional Note 8)

In the feature quantity calculating method according to an additional note 8, in the additional note 7, the first probe is formed of one or more kinds of monatomic ions or one or more kinds of point electric charges (the first to fifth point electric charges described above), and the second probe is formed of one or more kinds of polyatomic ions or dipoles (dipoles in which the first point electric charge and the second point electric charge are disposed to be separated from each other). Further, a compound is designated as the target structure in the target structure designating step, a three-dimensional structure of the compound formed of a plurality of atoms is generated in the three-dimensional structure generating step, and the fourth feature quantity which is a feature quantity obtained by quantifying, in the three-dimensional space, the degree of accumulation of the first and second probes in the periphery of the three-dimensional structure of the compound generated in the three-dimensional structure generating step is calculated in the feature quantity calculating step.

(Additional Note 9)

The feature quantity calculating method according to an additional note 9, in the additional note 7 or 8, further includes an invariant conversion step of converting the fourth feature quantity into an invariant with respect to rotation and translation of the target structure to calculate the fourth invariant feature quantity. According to the configuration of the additional note 9, since the fourth feature quantity is converted into an invariant with respect to rotation and translation of the compound, the fourth feature quantity is easily handled and the data capacity can be reduced.

FIG. 33 is a diagram showing an example of a result of comparative evaluation of the easiness of finding hits based on the invariant feature quantity (the fourth invariant feature quantity) using a compound as a target structure for the same system (protein ABL1) as in FIGS. 13, 31, and 32 related to the additional notes 7 to 9. In this example, a combination of the first probe that is a single probe and the second probe that is a complex probe is used as probes. Specifically, a point electric charge (the first point electric charge) having an electric charge of +1 and a point electric charge (the second point electric charge) having an electric charge of −1 are used as the first probe, and a dipole formed of the first point charge and the second point electric charge is used as the second probe. As shown in FIG. 33, it can be seen that the expectation value is improved as compared with the random case as in FIG. 32 (see FIG. 13), As described above, even in a case where an invariant feature quantity using a single probe (the first probe) and a complex probe (the second probe) as the probes is used, screening of a pharmaceutical candidate compound can be efficiently performed.

(Additional Note 10)

A feature quantity calculating program according to an additional note 10 which causes a computer to execute the feature quantity calculating method according to any one of the additional notes 7 to 9.

(Additional Note 11)

The feature quantity calculating device according to an additional note 11 is a feature quantity calculating device including a target structure designation unit which designates a target structure formed of a plurality of unit structures having chemical properties; a three-dimensional structure generation unit which generates a three-dimensional structure using the plurality of unit structures for the target structure; and a feature quantity calculation unit which calculates a feature quantity obtained by quantifying, in a three-dimensional space, the degree of accumulation of one or more kinds of probes in the periphery of the three-dimensional structure, in which the probes include a first probe that is a single point having a real electric charge and generating a van der Waals force and a second probe in which a plurality of points having a real electric charge and generating a van der Waals force are disposed to be separated from each other. According to the configuration of the additional note 10, similarly to the first aspect, the feature quantity accurately showing the chemical properties of the target structure can be calculated.

(Additional Note 12)

In the additional note 11, the first probe is formed of a monatomic ion or a point electric charge (the first to fifth point electric charges described above), and the second probe is formed of a polyatomic ion or a dipole (a dipole in which the first point electric charge and the second point electric charge are disposed to be separated from each other). Further, the target structure designation unit designates a compound as the target structure, the three-dimensional structure generation unit generates a three-dimensional structure of the compound formed of a plurality of atoms, and the feature quantity calculation unit calculates the fourth feature quantity which is a feature quantity obtained by quantifying, in the three-dimensional space, the degree of accumulation of the first and second probes in the periphery of the three-dimensional structure of the compound generated by the three-dimensional structure generation unit.

(Additional Note 13)

The feature quantity calculating device according to an additional note 13, in the additional note 12, further includes an invariant conversion unit which converts the fourth feature quantity into an invariant with respect to rotation and translation of the target structure to calculate the fourth invariant feature quantity. According to the configuration of the additional note 13, since the feature quantity is converted into an invariant with respect to rotation and translation of the compound, the feature quantity is easily handled and the data capacity can be reduced.

(Additional Note 14)

A construction method according to an additional note 14 is a construction method for a generator (a method of generating a prediction model) that accepts a feature quantity of a compound (the feature quantity obtained by quantifying, in a three-dimensional space, the degree of accumulation of probes in the periphery of the compound or the feature quantity obtained by converting the feature quantity thereof into an invariant with respect to rotation and translation of the compound) and outputs information showing a three-dimensional structure of the compound, and includes a learning processing step of inputting a data set for learning to the generator in which the information showing the three-dimensional structure of the compound is used as teacher data and the feature quantity calculated by the feature quantity calculating method according to any one of the first to seventh aspects or the feature quantity calculating method according to any one of the additional notes 7 to 9 is used as an explanatory variable to perform learning through machine learning for each of a plurality of compounds. The generator (prediction model) may comprise a hierarchical network. The generator (prediction model) may accept a three-dimensional image as information related to the three-dimensional structure of the compound. The hierarchical network (an example of the generator) may include a convolution layer that performs a convolution operation using a three-dimensional filter to reduce the feature map (information obtained from the input layer) and a deconvolution layer that performs a deconvolution operation using a three-dimensional filter to enlarge the feature map. The hierarchical network may accept a three-dimensional image in which the kinds of atoms constituting a compound are expressed by a difference in color (for example, a combination of weighted red, green, and blue is used) in the learning processing step. The three-dimensional image may be accepted by being divided into a plurality of channels (for example, three channels of red, green, and blue) corresponding to different colors. Further, the hierarchical network may accept the three-dimensional image by dividing the image into a plurality of channels corresponding to different kinds of atoms in the learning processing step. The hierarchical network may be a convolutional neural network.

Figure 34A:
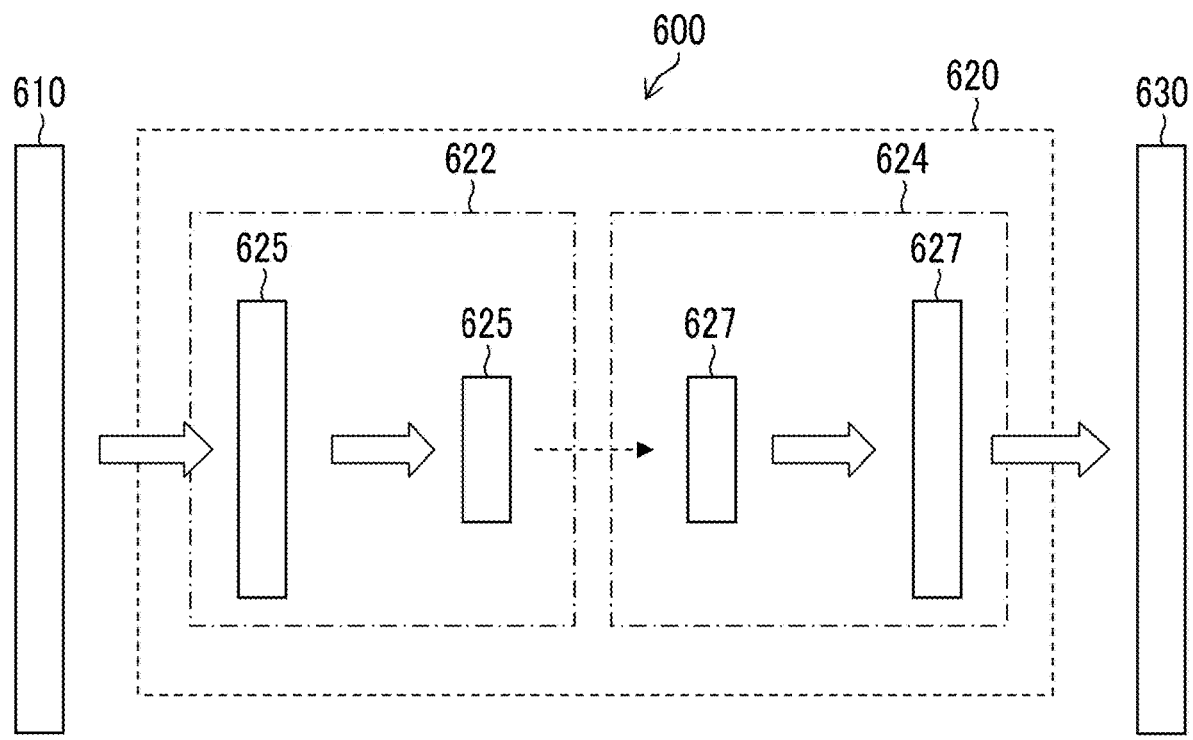
FIGS. 34A and 34B are views showing a configuration example of a hierarchical network.
Figure 34B:
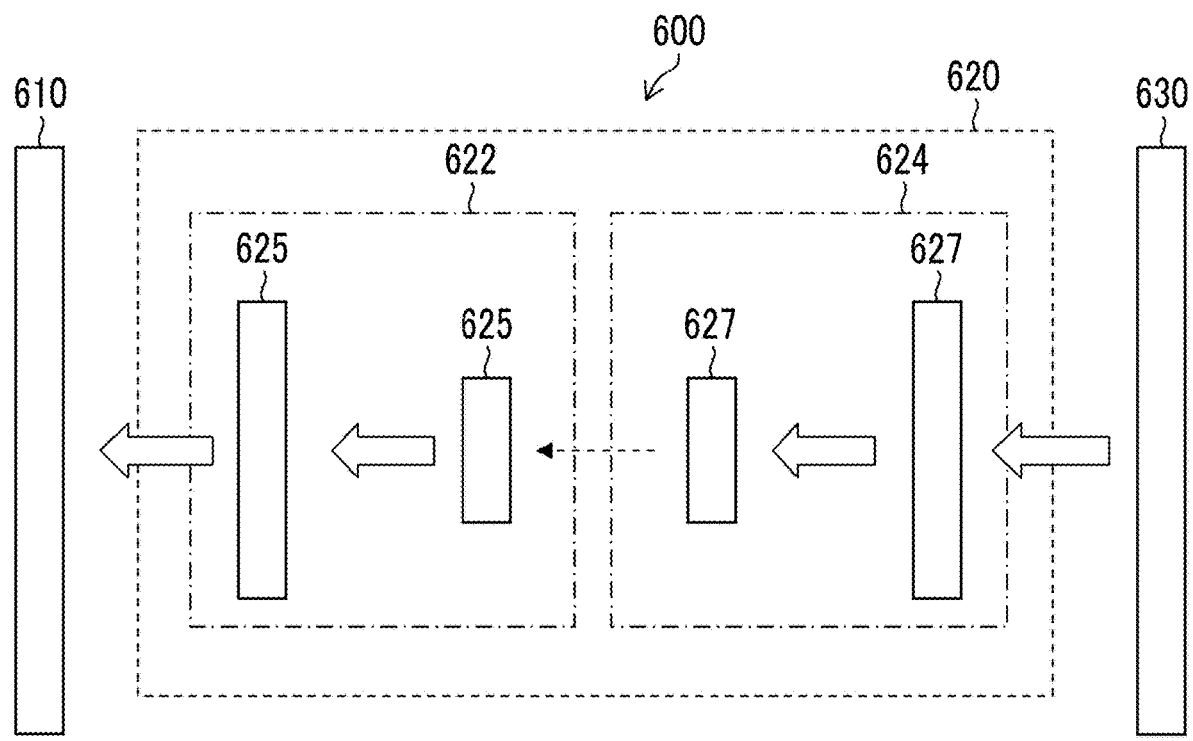

FIGS. 34A and 34B are views showing a configuration example of the hierarchical network according to the additional note 14. In FIG. 34A, a hierarchical network 600 is a convolutional neural network including an input layer 610, an interlayer 620, and an output layer 630. The interlayer 620 comprises a first interlayer 622 and a second interlayer 624. The first interlayer 622 includes a convolution layer that performs a convolution operation and a pooling layer that performs a pooling process (these two layers are collectively referred to as a layer 625), and lower-order feature extraction is performed in the layer close to an input side and higher-order feature extraction is performed as the layer approaches an output side. In a case of performing learning, the information is updated from the input layer 610 toward the output layer 630.

The second interlayer 624 includes a deconvolution layer that performs a deconvolution operation using a three-dimensional filter and a reverse pooling layer that performs a reverse pooling process (the two layers are collectively referred to as a layer 627 in FIG. 34A). The feature map is downscaled by the convolution operation and the pooling process in the first interlayer 622, and the feature map is upscaled by the deconvolution operation and the reverse pooling process in the second interlayer 624. The degree of downscaling and upscaling can be adjusted by changing the size of the three-dimensional filter, and as a result, three-dimensional information (the feature quantity obtained by quantifying the degree of accumulation of probes in the three-dimensional space in the periphery of the target structure) with the same size as that of the input three-dimensional image can be obtained. Further, the number and the combination of layers (the convolution layer, the pooling layer, the deconvolution layer, and the reverse pooling layer) in the first interlayer 622 and the second interlayer 624 are not particularly limited (the arrows indicated by dotted lines in FIGS. 34A and 34B indicate that the layers are not provided).

In a case where the hierarchical network 600 with the above-described configuration is used, it is preferable that a process (error back propagation) of comparing the result output by the output layer 630 with the correct answer of recognition (the feature quantity showing the degree of accumulation of probes) for an image set to calculate the loss (error) and updating the weight parameter in the interlayer 620 from the layer on the output side toward the layer on the input side such that the loss decreases is performed in the learning process. Further, the interlayer 620 may include a layer that performs batch normalization in addition to the convolution layer and the pooling layer and the deconvolution layer and the reverse pooling layer). The batch normalization process is a process of normalizing the distribution of data in a unit of mini-batch in a case of performing learning, and plays a role of quickly proceeding learning, reducing dependence on initial values, suppressing over-fitting, and the like.

In a case where the learning of the above-described hierarchical network 600 is completed, the feature quantity according to the present invention can be calculated by inputting the three-dimensional image (information showing the three-dimensional structure) of the compound. In this case, in a case where the three-dimensional structure information serving as actual data is input to the input layer 610 instead of the three-dimensional structure information serving as learning data, information related to the weight parameter of each layer is updated from the input layer 610 toward the output layer 630 (in the direction of the arrow in FIG. 34A), and the feature quantity is output from the output layer 630. Further, the three-dimensional structure of the compound can be created by reversing the input and the output (by inputting the feature quantity to the output layer 630 and outputting the three-dimensional image from the input layer 610). This relates to an aspect in which the hierarchical network 600 is used as a generator, a prediction model, and a learned model. In this case, in a case where the feature quantity is input to the output layer 630, the information is updated from the output layer 630 toward the input layer 610 (in the direction of the arrow in FIG. 34B), and the three-dimensional image showing the three-dimensional structure of the compound is output from the input layer 610.

(Additional Note 15)

A construction method according to an additional note 15 is a construction method for a generator (a method of generating a prediction model) that accepts a feature quantity of a compound and outputs information showing the structural formula of the compound, and includes a learning processing step of inputting a data set for learning to the generator in which the information showing the structural formula of the compound is used as teacher data and the feature quantity calculated by the feature quantity calculating method according to any one of the first to seventh aspects or the feature quantity calculated by the feature quantity calculating method according to any one of the additional notes 7 to 9 is used as an explanatory variable to perform learning through machine learning for each of a plurality of compounds. In the learning processing step, the generator can output the feature quantity obtained by accepting a descriptor formed from the structural formula (which can be expressed by a combination of characters, numbers, and symbols) and converting the degree of accumulation of probes into an invariant. The generator according to the additional note 15 can be formed by using a hierarchical network such as a neural network, and in this case, the generator may include an interlayer formed of fully connected layers. In the additional note 15, a descriptor that can be formed from the structural formula (for example, a Fingerprint descriptor) can be used as "information showing the structural formula".

Figure 35A:
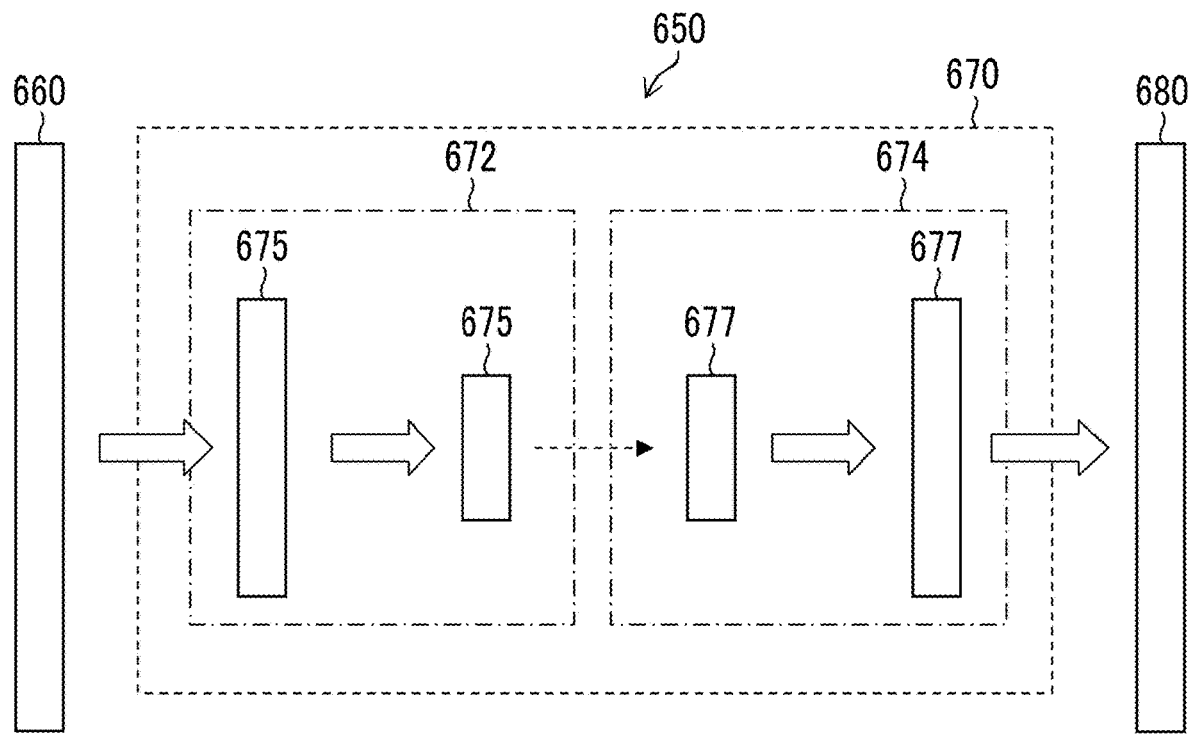
FIGS. 35A and 35B are views showing another configuration example of the hierarchical network.
Figure 35B:
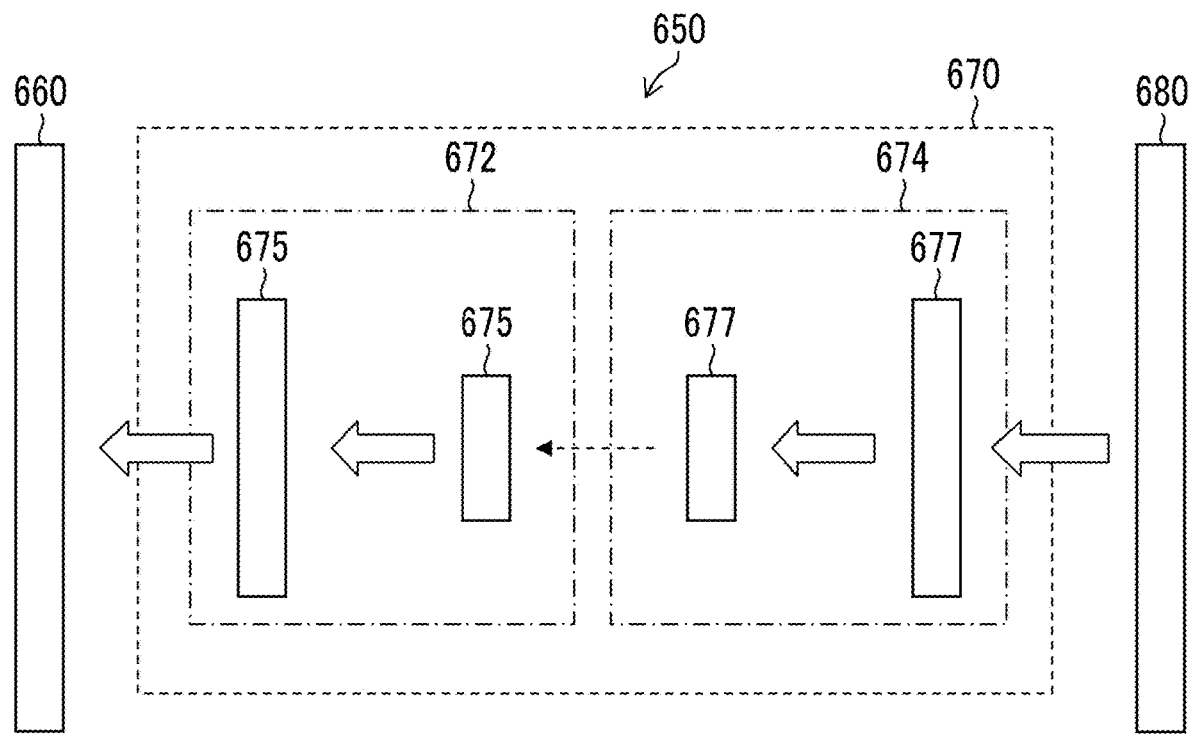

FIGS. 35A and 35B are views showing a configuration example of the hierarchical network according to the additional note 15. In FIG. 35A, a hierarchical network 650 includes an input layer 660, an interlayer 670, and an output layer 680. The interlayer 670 comprises a first interlayer 672 and a second interlayer 674 (each layer of the first interlayer 672 is referred to as a layer 675, and each layer of the second interlayer 674 is referred to as a layer 677). The hierarchical network 650 is a neural network in which the input layer 660, the interlayer 670, and the output layer 680 are fully connected to each other. The feature map is downscaled in the first interlayer 672, and the feature map is upscaled in the second interlayer 674. By adjusting the degree of downscaling and upscaling, a feature quantity (an invariant feature quantity) with the same size as that of the input information (descriptor) can be obtained. Further, the number and the combination of layers in the first interlayer 672 and the second interlayer 674 are not particularly limited (the arrows indicated by dotted lines in FIGS. 35A and 35B indicate that the layer are not provided).

In a case where the hierarchical network 650 with the above-described configuration is used, it is preferable that a process (error back propagation) of comparing the result output by the output layer 680 with the correct answer of the output (the invariant feature quantity) with respect to the input descriptor to calculate the loss (error) and updating the weight parameter in the interlayer 670 from the layer on the output side toward the layer on the input side such that the loss decreases is performed in the learning process.

In a case where the learning of the above-described hierarchical network 650 is completed, the feature quantity (the invariant feature quantity) according to the present invention can be calculated by inputting a descriptor of the compound (a descriptor that can be formed from the structural formula). In this case, in a case where a descriptor serving as actual data is input instead of a descriptor as learning data, the information related to the weight parameter and the like of each layer is updated from the input layer 660 toward the output layer 680 (in the direction of the arrow in FIG. 35A), and the invariant feature quantity is output from the output layer 680. Further, the information showing the three-dimensional structure of the compound can also be created by reversing the input and the output (by inputting the invariant feature quantity to the output layer 680 and outputting the descriptor from the input layer 660). This relates to an aspect in which the hierarchical network 650 is used as a generator, a prediction model, and a learned model. In this case, in a case where the invariant feature quantity is input to the output layer 680, the information is updated from the output layer 680 toward the input layer 660 (in the direction of the arrow in FIG. 35B), and the descriptor of the compound is output from the input layer 660.

(Additional Note 16)

An additional note 16 relates to a generator (a prediction model and a learned model) constructed by the construction method according to the additional note 14 or 15.

(Additional Note 17)

A feature quantity calculating method according to an additional note 17 is a feature quantity calculating method using the generator according to the additional note 16, and includes a feature quantity calculating step of inputting the information (for example, the three-dimensional image) showing the three-dimensional structure of a compound to the generator according to the additional note 16 to generate the feature quantity (the degree of accumulation of probes in the periphery of the compound).

(Additional Note 18)

A compound creating method according to an additional note 18 is a compound creating method using the generator according to the additional note 16, and includes a three-dimensional structure generating step of inputting the feature quantity calculated by the feature quantity calculating method according to any one of the first to seventh aspects or the feature quantity calculating method according to any one of the additional notes 7 to 9 to the generator corresponding to the calculation method for the feature quantity and generating information showing the three-dimensional structure of the compound (a three-dimensional structure, a three-dimensional image, a three-dimensional descriptor, and the like). The compound creating method according to the additional note 18 enables performance of the same process (creation of a compound) as the process of the compound creating method according to the fifteenth or sixteenth aspect or the compound creating method according to any one of the additional notes 11 to 13. The generator accepts the information showing the three-dimensional structure and outputs the feature quantity in the learning processing step, but the generator reverses the input and the output in a case where the creation of a compound is performed (the three-dimensional feature quantity or the invariant feature quantity is input to the output layer in the learning processing step, and the three-dimensional image or the descriptor is output from the input layer in the learning processing step). Further, in the compound creating method according to the additional note 18, it is preferable that the generator that inputs the feature quantity is a generator corresponding to the feature quantity calculating method in which the feature quantity is calculated. For example, in a case where the first feature quantity (or the first invariant feature quantity) is input to the generator, it is preferable that the generator is a generator formed by learning using the first feature quantity (or the first invariant feature quantity).

EXPLANATION OF REFERENCES

10: screening device
20: compound creating device
30: pharmaceutical candidate compound search device
100: processing unit
101: processing unit
102: processing unit
110: information input unit
120: feature quantity calculation unit
130: similarity calculation unit
132: generator construction unit
140: compound extraction unit 142: compound three-dimensional structure generation unit
150: display control unit
160: CPU
170: ROM
180: RAM
200: storage unit
201: storage unit
202: storage unit
210: structure information
220: three-dimensional structure information
230: three-dimensional AAM descriptor
240: invariant AAM descriptor
250: similarity information
260: Compound extraction result
270: three-dimensional structure generation result
300: display unit
310: monitor
400: operation unit
410: keyboard
420: mouse
500: external server
510: external database
600: hierarchical network
610: input layer
620: interlayer
622: first interlayer
624: second interlayer
625: layer
627: layer
630: output layer
650: hierarchical network
660: input layer
670: interlayer
672: first interlayer
674: second interlayer
675: layer
677: layer
680: output layer
A1: amino acid
A2: amino acid
A3: amino acid
AA2AR: protein
ABL1: protein
NW: network
PO: pocket
PS: pocket structure
S100 to S108: each step of feature quantity calculating method
S200 to S206: each step of feature quantity calculating method
S300 to S304: each step of target compound extracting method
S400 to S404: each step of target compound extracting method
S500 to S504: each step of three-dimensional structure creating method
S600 to S604: each step of three-dimensional structure creating method
TP: target protein

What is claimed is:

1. A feature quantity calculating method executed by a computer having a processor, the processor configured to perform the method comprising:

a target structure designating step of designating a target structure formed of a plurality of unit structures having chemical properties;

a three-dimensional structure generating step of generating a three-dimensional structure using the plurality of unit structures for the target structure;

a feature quantity calculating step of calculating a feature quantity obtained by quantifying, in a three-dimensional space, a degree of accumulation of one or more kinds of probes in a periphery of the three-dimensional structure; and an invariant conversion step of converting the feature quantity into an invariant with respect to rotation and translation of the target structure to calculate an invariant feature quantity, wherein the probe is a single point having a real electric charge and generating a van der Waals force, and wherein a compound is designated as the target structure in the target structure designating step, a three-dimensional structure of the compound formed of a plurality of atoms is generated in the three-dimensional structure generating step, a first feature quantity which is a feature quantity obtained by quantifying, in the three-dimensional space, the degree of accumulation of the probes in the periphery of the three-dimensional structure of the compound generated in the three-dimensional structure generating step which is the degree of accumulation using one or more kinds of monatomic ions as the probes is calculated in the feature quantity calculating step, and a first invariant feature quantity is calculated by converting the first feature quantity into an invariant with respect to rotation and translation of the compound in the invariant conversion step.

2. The feature quantity calculating method according to claim 1, wherein the first feature quantity of a first probe that is formed of the one or more kinds of monatomic ions and the first feature quantity of a second probe that is formed of the one or more kinds of monatomic ions and different from the first probe are calculated in the feature quantity calculating step, and the first invariant feature quantity is calculated using the first feature quantity of the first probe and the first feature quantity of the second probe in the invariant conversion step.

3. A non-temporary computer-readable recording medium which causes a computer to execute the feature quantity calculating method according to claim 1 in a case where a command stored in the recording medium is read by the computer.

4. A screening method executed by a computer having a processor, the processor configured to perform the method of extracting a target compound which is bound to a target biopolymer other than a protein from a plurality of compounds, the method comprising:

a storing step of storing a three-dimensional structure of a compound formed of a plurality of atoms and the first invariant feature quantity of the three-dimensional structure of the compound which is calculated using the feature quantity calculating method according to claim 1 in association with each other for each of the plurality of compounds;

a feature quantity calculating step of calculating the first invariant feature quantity of a binding compound that is a compound whose binding to the target biopolymer other than the protein has been confirmed;

a similarity calculating step of calculating a similarity between the first invariant feature quantity of the plurality of compounds and the first invariant feature quantity of the binding compound; and
a compound extracting step of extracting the target compound from the plurality of compounds based on the similarity.

5. A non-temporary computer-readable recording medium which causes a computer to execute the screening method according to claim 4 in a case where a command stored in the recording medium is read by the computer.

6. A screening device having a processor the processor configured to perform functionality of units, which extracts a target compound bound to a target biopolymer other than a protein from a plurality of compounds, the device comprising:
    a storage unit which stores a three-dimensional structure of a compound formed of a plurality of atoms and the first invariant feature quantity of the three-dimensional structure of the compound which is calculated using the feature quantity calculating method according to claim 1 in association with each other for each of the plurality of compounds;
    a feature quantity calculation unit which calculates the first invariant feature quantity of a binding compound that is a compound whose binding to the target biopolymer other than the protein has been confirmed;
    a similarity calculation unit which calculates a similarity between the first invariant feature quantity of the plurality of compounds and the first invariant feature quantity of the binding compound; and
    a compound extraction unit which extracts the target compound from the plurality of compounds based on the similarity.

7. A compound creating method executed by a computer having a processor, the processor configured to perform the method of creating a three-dimensional structure of a target compound that is bound to a target biopolymer other than a protein from a plurality of compounds, the method comprising:
    a storing step of storing a three-dimensional structure of a compound formed of a plurality of atoms and the first invariant feature quantity in association with each other for each of the plurality of compounds;
    a feature quantity calculating step of calculating the first invariant feature quantity of a binding compound that is a compound whose binding to the target biopolymer other than the protein has been confirmed using the feature quantity calculating method according to claim 1;
    a generator constructing step of constructing a generator through machine learning using the three-dimensional structure of the plurality of compounds as teacher data and the first invariant feature quantity as an explanatory variable; and
    a compound three-dimensional structure generating step of generating a three-dimensional structure of the target compound from the first invariant feature quantity of the binding compound using the generator.

8. A non-temporary computer-readable recording medium which causes a computer to execute the compound creating method according to claim 7 in a case where a command stored in the recording medium is read by the computer.

9. A compound creating device having a processor, the processor is configured to perform functionality of units, which creates a three-dimensional structure of a target compound that is bound to a target biopolymer other than a protein from a plurality of compounds, the device comprising:
    a storage unit which stores a three-dimensional structure of a compound formed of a plurality of atoms and a first invariant feature quantity in association with each other for each of the plurality of compounds;
    a feature quantity calculation unit which calculates the first invariant feature quantity of a binding compound that is a compound whose binding to the target biopolymer other than the protein has been confirmed using the feature quantity calculating method according to claim 1;
    a generator construction unit which constructs a generator through machine learning using the three-dimensional structure of the plurality of compounds as teacher data and the first invariant feature quantity as an explanatory variable; and
    a compound three-dimensional structure generation unit which generates a three-dimensional structure of the target compound from the first invariant feature quantity of the binding compound using the generator.

10. The feature quantity calculating method according to claim 1,
    wherein the processor is further configured to designate compounds, indicated by information obtained from an external server and/or an external database via a network, as the target structure.

11. The feature quantity calculating method according to claim 1,
    wherein the processor is configured to store the invariant feature quantity into a storage device in association with structure information of the target structure.

12. The feature quantity calculating method according to claim 1,
    wherein the processor is configured to cause a display device to display at least one of the calculated invariant feature quantity and the generated three-dimensional structure.

13. A feature quantity calculating method executed by a computer having a processor, the processor configured to perform the method comprising:
    a target structure designating step of designating a target structure formed of a plurality of unit structures having chemical properties;
    a three-dimensional structure generating step of generating a three-dimensional structure using the plurality of unit structures for the target structure;
    a feature quantity calculating step of calculating a feature quantity obtained by quantifying in a three-dimensional space, a degree of accumulation of one or more kinds of probes in a periphery of the three-dimensional structure; and
    an invariant conversion step of converting the feature quantity into an invariant with respect to rotation and translation of the target structure to calculate an invariant feature quantity,
    wherein the probe is a single point having a real electric charge and generating a van der Waals force,
    wherein a compound is designated as the target structure in the target structure designating step,
    a three-dimensional structure of the compound formed of a plurality of atoms is generated in the three-dimensional structure generating step,
    a second feature quantity which is a feature quantity obtained by quantifying, in the three-dimensional space, the degree of accumulation of the probes in the periphery of the three-dimensional structure of the compound generated in the three-dimensional structure generating step which is the degree of accumulation using one or more selected from a first point electric charge having an electric charge of +1, a second point electric charge having an electric charge of −1, a third point electric charge having an electric charge of +0.1, a fourth point electric charge having an electric charge of −0.1, and a fifth point electric charge having an electric charge of 0, as the probes is calculated in the feature quantity calculating step, and a second invariant feature quantity is calculated by converting the second feature quantity into an invariant with respect to rotation and translation of the compound in the invariant conversion step.

14. The feature quantity calculating method according to claim 13,
wherein the second feature quantity of a first probe that is formed of one or more selected from the first point electric charge, the second point electric charge, the third point electric charge, the fourth point electric charge, and the fifth point electric charge and the second feature quantity of a second probe that is formed of one or more selected from the first point electric charge, the second point electric charge, the third point electric charge, the fourth point electric charge, and the fifth point electric charge and different from the first probe are calculated in the feature quantity calculating step, and
the second invariant feature quantity is calculated using the second feature quantity of the first probe and the second feature quantity of the second probe in the invariant conversion step.

15. The feature quantity calculating method according to claim 14,
wherein a compound is designated as the target structure in the target structure designating step,
a three-dimensional structure of the compound formed of a plurality of atoms is generated in the three-dimensional structure generating step,
a third feature quantity which is a feature quantity obtained by quantifying, in the three-dimensional space, the degree of accumulation of the probes in the periphery of the three-dimensional structure of the compound generated in the three-dimensional structure generating step which is the degree of accumulation using the first probe that is formed of one or more kinds of monatomic ions and the second probe that is formed of one or more selected from the first point electric charge having an electric charge of +1, the second point electric charge having an electric charge of −1, the third point electric charge having an electric charge of +0.1, the fourth point electric charge having an electric charge of −0.1, and the fifth point electric charge having an electric charge of 0, as the probes is calculated in the feature quantity calculating step, and
a third invariant feature quantity is calculated using the third feature quantity of the first probe and the third feature quantity of the second probe in the invariant conversion step.

16. The feature quantity calculating method according to claim 15,
wherein the third feature quantity of two kinds of the probes in which at least one of the first probe or the second probe is different is calculated in the feature quantity calculating step, and
the third invariant feature quantity is calculated using the third feature quantity of the two kinds of the probes in the invariant conversion step.

17. A screening method executed by a computer having a processor, the processor configured to perform the method of extracting a target compound which is bound to a target biopolymer from a plurality of compounds, the method comprising:
a storing step of storing a three-dimensional structure of a compound formed of a plurality of atoms and the second invariant feature quantity of the three-dimensional structure of the compound which is calculated using the feature quantity calculating method according to claim 4 in association with each other for each of the plurality of compounds;
a feature quantity calculating step of calculating the second invariant feature quantity of a binding compound that is a compound whose binding to the target biopolymer has been confirmed;
a similarity calculating step of calculating a similarity between the second invariant feature quantity of the plurality of compounds and the second invariant feature quantity of the binding compound; and
a compound extracting step of extracting the target compound from the plurality of compounds based on the similarity.

18. A screening device having a processor, the processor configured to perform functionality of units, which extracts a target compound bound to a target biopolymer from a plurality of compounds, the device comprising:
a storage unit which stores a three-dimensional structure of a compound formed of a plurality of atoms and the second invariant feature quantity of the three-dimensional structure of the compound which is calculated using the feature quantity calculating method according to claim 13 in association with each other for each of the plurality of compounds;
a feature quantity calculation unit which calculates the second invariant feature quantity of a binding compound that is a compound whose binding to the target biopolymer has been confirmed;
a similarity calculation unit which calculates a similarity between the second invariant feature quantity of the plurality of compounds and the second invariant feature quantity of the binding compound; and
a compound extraction unit which extracts the target compound from the plurality of compounds based on the similarity.

19. A compound creating method executed by a computer having a processor. the processor configured to perform the method of creating a three-dimensional structure of a target compound that is bound to a target biopolymer from a plurality of compounds, the method comprising:
a storing step of storing a three-dimensional structure of a compound formed of a plurality of atoms and a second invariant feature quantity in association with each other for each of the plurality of compounds;
a feature quantity calculating step of calculating the second invariant feature quantity of a binding compound that is a compound whose binding to the target biopolymer has been confirmed using the feature quantity calculating method according to claim 13;
a generator constructing step of constructing a generator through machine learning using the three-dimensional structure of the plurality of compounds as teacher data and the second invariant feature quantity as an explanatory variable; and
a compound three-dimensional structure generating step of generating a three-dimensional structure of the target compound from the second invariant feature quantity of the binding compound using the generator.

20. A compound creating device having a processor, the processor configured to perform functionality of units which creates a three-dimensional structure of a target compound that is bound to a target biopolymer from a plurality of compounds, the device comprising:
- a storage unit which stores a three-dimensional structure of a compound formed of a plurality of atoms and a second invariant feature quantity in association with each other for each of the plurality of compounds;
- a feature quantity calculation unit which calculates the second invariant feature quantity of a binding compound that is a compound whose binding to the target biopolymer has been confirmed using the feature quantity calculating method according to claim 13;
- a generator construction unit which constructs a generator through machine learning using the three-dimensional structure of the plurality of compounds as teacher data and the second invariant feature quantity as an explanatory variable; and
- a compound three-dimensional structure generation unit which generates a three-dimensional structure of the target compound from the second invariant feature quantity of the binding compound using the generator.

21. A feature quantity calculating device having a processor, the processor configured to perform functionality of units, comprising:
- a target structure designation unit which designates a target structure formed of a plurality of unit structures having chemical properties;
- a three-dimensional structure generation unit which generates a three-dimensional structure using the plurality of unit structures for the target structure;
- a feature quantity calculation unit which calculates a feature quantity obtained by quantifying, in a three-dimensional space, a degree of accumulation of one or more kinds of probes in a periphery of the three-dimensional structure; and
- an invariant conversion unit which converts the feature quantity into an invariant with respect to rotation and translation of the target structure to calculate an invariant feature quantity,
- wherein the probe is a single point having a real electric charge and generating a van der Waals force, and
- wherein a compound is designated as the target structure in the target structure designating step
- a three-dimensional structure of the compound formed of a plurality of atoms is generated in the three-dimensional structure generating step,
- a first feature quantity which is a feature quantity obtained by quantifying, in the three-dimensional space, the degree of accumulation of the probes in the periphery of the three-dimensional structure of the compound generated in the three-dimensional structure generating step which is the degree of accumulation using one or more kinds of monatomic ions as the probes is calculated in the feature quantity calculating step, and
- a first invariant feature quantity is calculated by converting the first feature quantity into an invariant with respect to rotation and translation of the compound in the invariant conversion step.

22. The feature quantity calculating device according to claim 21,
wherein the processor is further configured to designate compounds, indicated by information obtained from an external server and/or an external database via a network, as the target structure.

23. The feature quantity calculating device according to claim 21,
wherein the processor is configured to store the invariant feature quantity into a storage device in association with structure information of the target structure.

24. The feature quantity calculating device according to claim 21,
wherein the processor is configured to cause a display device to display at least one of the calculated invariant feature quantity and the generated three-dimensional structure.

* * * * *